(12) United States Patent
Lee et al.

(10) Patent No.: US 9,899,600 B2
(45) Date of Patent: Feb. 20, 2018

(54) MULTICYCLIC AROMATIC COMPOUND AND ORGANIC LIGHT EMITTING DEVICE USING THE SAME

(71) Applicant: HEESUNG MATERIAL LTD., Yongin, Gyeonggi-Do (KR)

(72) Inventors: Do-Hyung Lee, Yongin (KR); Dong-Jun Kim, Osan (KR); Young-Seok No, Cheongwon-gun (KR); Hyundong Chun, Seoul (KR); Joo-Dong Lee, Seongnam (KR)

(73) Assignee: Heesung Material Ltd., Yongin (KR)

( * ) Notice: Subject to any disclaimer, the term of this patent is extended or adjusted under 35 U.S.C. 154(b) by 742 days.

(21) Appl. No.: 14/090,648

(22) Filed: Nov. 26, 2013

(65) Prior Publication Data

US 2014/0145169 A1 May 29, 2014

(30) Foreign Application Priority Data

Nov. 26, 2012 (KR) ........................ 10-2012-0134761

(51) Int. Cl.
| | | |
|---|---|---|
| H01L 51/00 | (2006.01) |
| C07C 211/54 | (2006.01) |
| C07D 263/57 | (2006.01) |
| C07D 209/08 | (2006.01) |
| C07D 277/66 | (2006.01) |
| C07D 209/86 | (2006.01) |
| C07C 13/62 | (2006.01) |
| C07C 13/66 | (2006.01) |
| C09K 11/06 | (2006.01) |
| H05B 33/14 | (2006.01) |
| C07F 7/08 | (2006.01) |
| C09B 57/00 | (2006.01) |
| C09B 1/00 | (2006.01) |

(52) U.S. Cl.
CPC .......... *H01L 51/0054* (2013.01); *C07C 13/62* (2013.01); *C07C 13/66* (2013.01); *C07C 211/54* (2013.01); *C07D 209/08* (2013.01); *C07D 209/86* (2013.01); *C07D 263/57* (2013.01); *C07D 277/66* (2013.01); *C07F 7/0818* (2013.01); *C09B 1/00* (2013.01); *C09B 57/00* (2013.01); *C09B 57/001* (2013.01); *C09B 57/008* (2013.01); *C09K 11/06* (2013.01); *H01L 51/0058* (2013.01); *H05B 33/14* (2013.01); *C07B 2200/05* (2013.01); *C07C 2602/08* (2017.05); *C07C 2603/18* (2017.05); *C07C 2603/20* (2017.05); *C07C 2603/24* (2017.05); *C07C 2603/26* (2017.05); *C07C 2603/28* (2017.05); *C07C 2603/40* (2017.05); *C07C 2603/50* (2017.05); *C07C 2603/54* (2017.05); *C09K 2211/1007* (2013.01); *C09K 2211/1011* (2013.01); *C09K 2211/1014* (2013.01); *C09K 2211/1029* (2013.01); *C09K 2211/1033* (2013.01)

(58) Field of Classification Search
CPC ..... C07F 7/0818; C07C 211/54; C07C 13/62; C07C 13/66; C07C 2603/20; C07C 2603/18; C07C 2603/26; C07C 2602/08; C07C 2603/28; C07C 2603/40; C07C 2603/50; C07C 2603/54; C07C 2603/24; C07D 263/57; C07D 209/08; C07D 277/66; C07D 209/86; C09K 11/06; C09K 2211/1007; C09K 2211/1011; C09K 2211/1029; C09K 2211/1033; C09K 2211/1014; H05B 33/14; H01L 51/0054; H01L 51/0058; C09B 57/00; C09B 57/001; C09B 57/008; C09B 1/00; C07B 2200/05
See application file for complete search history.

(56) References Cited

U.S. PATENT DOCUMENTS

| | | | |
|---|---|---|---|
| 2003/0020073 A1* | 1/2003 | Long ................... | H01L 27/3211 257/79 |
| 2004/0076853 A1 | 4/2004 | Jarikov | |
| 2004/0241491 A1* | 12/2004 | Hatwar ............... | H01L 51/0079 428/690 |
| 2009/0179551 A1 | 7/2009 | Kwon et al. | |
| 2009/0230854 A1 | 9/2009 | Kim et al. | |
| 2014/0197393 A1* | 7/2014 | Lee ..................... | H01L 51/0052 257/40 |

FOREIGN PATENT DOCUMENTS

| | | | |
|---|---|---|---|
| CN | 101313047 A | 11/2008 | |
| KR | 10-2007-0101430 A | 10/2007 | |
| KR | 10-2010-0048447 A | 5/2010 | |
| KR | 10-2010-0064712 A | 6/2010 | |
| KR | 10-2010-0118700 A | 11/2010 | |
| WO | WO 9858037 A1 * | 12/1998 | ............. C09K 11/06 |

(Continued)

OTHER PUBLICATIONS

Yang et al, Synthesis and Characterization of 5,10-Bis(2-thienyl)indeno[2,1-a]indene Derivatives: The First Examples of Conducting Polymers Containing a Rigid Bis(thienyl)butadiene Core, The Journal of Organic Chemistry, vol. 65, Issues 20, pp. 6739-7642 (2000).*

(Continued)

*Primary Examiner* — Alexander Kollias
(74) *Attorney, Agent, or Firm* — Birch, Stewart, Kolasch & Birch, LLP

(57) ABSTRACT

The present specification describes a multicyclic aromatic ring compound having a novel structure and an organic light emitting device using the same.

16 Claims, 2 Drawing Sheets

(56) References Cited

FOREIGN PATENT DOCUMENTS

| WO | WO 2010/050778 A1 | 5/2010 |
|---|---|---|
| WO | WO 2010/064871 A1 | 6/2010 |
| WO | WO 2010/126234 A1 | 11/2010 |

OTHER PUBLICATIONS

Hellwinkel et al, Carbanion-Induced Skeletal-Rearrangements: From the Dibenzo[a,e] cyclooctene to the Indeno[2,1-a]indene Framework, Angewandte Cemie, International Edition, vol. 23, Issue 9,pp. 705-706, Sep. 1984.*

M. Saito, Synthesis and Reacitons of Dibenzo[a,e]pentalenes, Symmetry, vol. 2, pp. 950-969, 2010.*

Gao et al, Efficient Deep-Blue Organic Light-Emitting Diodes: Arylamine-Substituted Oligofluorenes, Advanced Functional Materials, vol. 17, Issue 16, pp. 3194-3199, Nov. 2007.*

Zerubba et al, Versatile Synthesis of Pentalene Derivatives Via the Pd-catalyzed Homocoupling of Haloenynes, J. Am. Chem. Soc vol. 131, Issues 8, pp. 2796-2797 (2009).*

Zhao et al, Pd-Catalyzed Cascade Crossover Annulation of o-Alkynylarylhalides and Diarylacetylenes Leading to Dibenzo[a,e]pentalenes, J. Am. Chem. Soc. vol. 135, Issues 28, pp. 10222-10225, Published Jun. 11, 2013.*

Maekawa et al, C—H activation route to dibenzo[a,e]pentalenes: annulation of arylacetylenes promoted by PdCl2—AgOTf-o-chloranil, Chemical Science, vol. 4, Issue 6, pp. 2369-2373, Published Mar. 20, 2013.*

STN Search Report, p. 1, dated Aug. 2, 2017.*

Muller et al, Coordination Chemistry of Ethynes. II. Indenoindenes From Transition-metal Complexes of 1,2-bis(phenylethinyl)benzene, European Jounral of Organic Chemistry, vol. 723, Issue 1, pp. 76-82, Jun. 6, 1969.*

Abou-Hadeed, K. et al, "Product Class 24: Pentalenes, s-Indacenes, as-Indacenes, Azulenes, and Heptalenes, and Their Benzo Derivatives," Science of Synthesis, 2010, vol. 45b, pp. 1043-1057.

Babu, G. et al, "Facile Carbolithiathon of Bent Alkyne without Catalyst. Tandem Route to Dibenzo[b,f]pentalenes from Dibenzocyclooctadiyne," Chemistry Letters, 2008, vol. 37, No. 12, pp. 1296-1297.

Badrieh, Y. et al, "Some Unusual Reactions of 1,2-Bis(phenylethynyl)benzene with Sulfur, Carbon Monoxide and Alkyl Acetylenedicarboxylates," Chem. Ber., Mar. 1, 1992, vol. 125, No. 3, pp. 667-674.

Baidossi, W. et al, "Selective Transformations of Phenylated Diynes to Polycyclic Compounds by the RhCl3- and PtCl4-Aliquat 336 Ion Pair Catalysts," Tetrahedron, Jun. 10, 1996, vol. 52, No. 24, pp. 8349-8364.

Ballester, M. et al, "Perchlorotolane. A new synthesis and its thermal dimerization," Tetrahedron Letters, Jan. 1, 1980, vol. 21, No. 29, pp. 2845-2848.

Chase, D.T. et al, "Electron-Accepting 6,12-Diethynylindeno [1,2-b]fluorenes: Synthesis, Crystal Structures, and Photophysical Properties," Angew. Chem. Int. Ed., Nov. 18, 2011, vol. 50, No. 47, pp. 11103-11106.

Chinese Office Action for Appl. No. 201310612060.4 dated Mar. 25, 2015 (w/ English translation).

European Search Report for Appl. No. 13194341.7 dated Apr. 29, 2014.

Gerson. F. et al, "Radical Ions of Conjugated Polycyclic Hydrocarbons Containing Two Phenalenyl Pi-systems," Helvetica Chimica Acta, Jun. 20, 1984, vol. 67, No. 4, pp. 934-938.

Hashmi, A. S. K. et al, "Gold-Catalyzed Synthesis of Dibenzopentalenes—Evidence for Gold Vinylidenes," Advanced Synthesis & Catalysts, Mar. 23, 2012, vol. 354, No. 4, pp. 555-562.

Japanese Office Action for Appl. No. 2013-244199 dated Mar. 3, 2015 (w/ English translation).

Kawase, T. et al, "Dinaphthopentalenes: Pentalene Derivatives for Organic Thin-Film Transistors," Angew. Chem. Int. Ed., Oct. 11, 2010, vol. 49, No. 42, pp. 7728-7732.

Korean Office Action for Appl. No. 10-2013-0144941 dated May 18, 2015 (w/ English translation).

Levi, Z.U. et al, "Synthesis and Electronic Properties of Extended, Fused-Ring Aromatic Systems Containing Multiple Pentalene Units," J.Am. Chem. Soc., Aug. 18, 2010, vol. 132, No. 32, pp. 11012-11014.

Nakasuji, K. et al, "Design and Synthesis of a Highly Amphoteric Condensed Hydrocarbon with the Highest Reduction Potential: Pentaleno[1,2,3-cd:4,5,6-c'd']diphenalene," J.Am. Chem., Jul. 1, 1983, vol. 105, No. 15, pp. 5136-5137.

Taiwanese Office Action for Appl. No. 102142956 dated Nov. 18, 2014 (w/ English translation).

Yang, J. et al, "Synthesis and Characterization of 5,10-Bis(2-thienyl)indeno[2,1-alpha]indene Derivatives: The First Examples of Conducting Polymers Containing a Rigid Bis(thienyl)butadiene Core," J. Org. Chem., Oct. 1, 2000, vol. 65, No. 20, pp. 6739-6742.

Zhang, H. et al, "Intramolecular Reductive Double Cyclization of o,o'-Bis(arylcarbonyl)-diphenylacetylenes: Synthesis of Ladder Pi-Conjugated Skeletons," Organic Letters, 2009, vol. 11, No. 14, pp. 3076-3079.

* cited by examiner

[Figure 1]
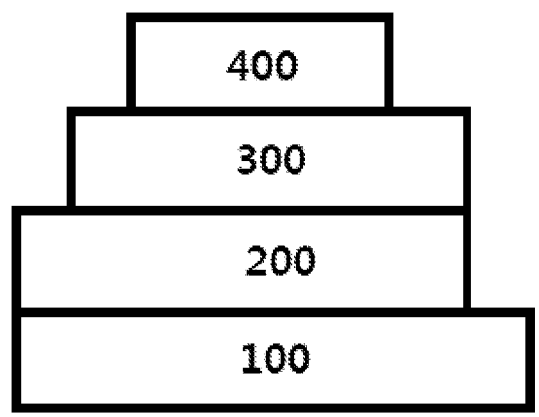
[Figure 2]
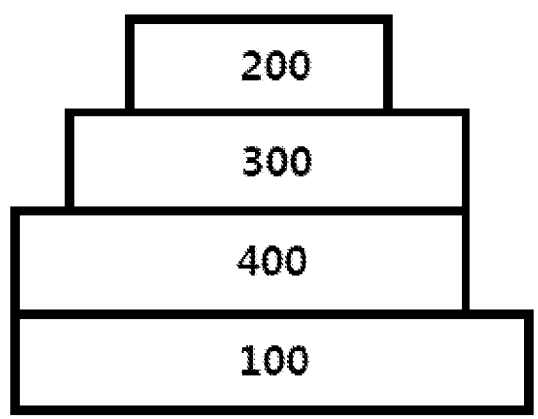

[Figure 3]
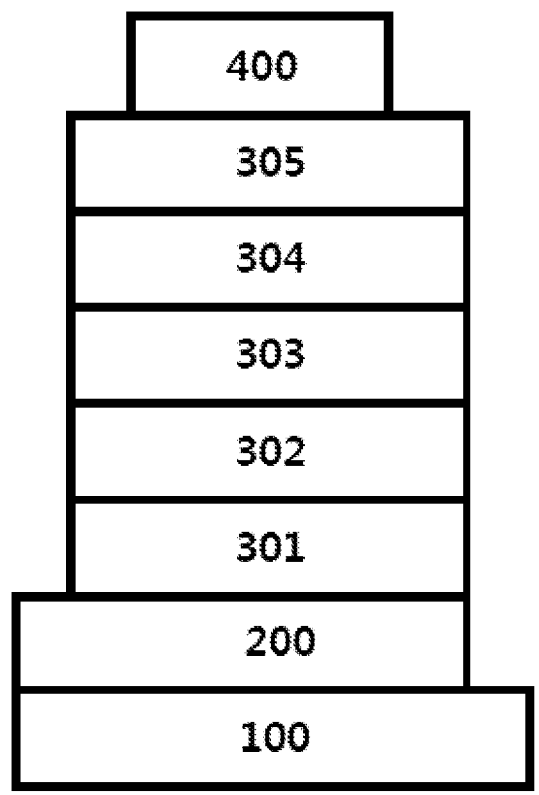

MULTICYCLIC AROMATIC COMPOUND AND ORGANIC LIGHT EMITTING DEVICE USING THE SAME

FIELD OF THE INVENTION

The present invention relates to a novel multicyclic aromatic compound and an organic light emitting device using the same.

BACKGROUND OF THE INVENTION

An electroluminescent device is one type of self-luminescent-type display devices, and has advantages in that it has a wide viewing angle, an excellent contrast, and quick response time.

An organic light emitting device has a structure in which an organic thin film is disposed between two electrodes. When voltage is applied to an organic light emitting device having such a structure, light emits by electrons and holes injected from the two electrodes being dissipated after the electrons and holes make a pair by bonding in the organic thin film. The organic thin film may be formed as a monolayer or a multilayer as necessary.

Materials of an organic thin film may have a light emitting function when necessary. For example, as the material of an organic thin film, compounds capable of forming a light emitting layer alone may be used, or compounds capable of performing as a host or a dopant of a host-dopant-based light emitting layer may also be used. In addition to these, compounds capable of performing hole injection, hole transfer, electron blocking, hole blocking, electron transfer, electron injection, or the like, may also be used as the material of an organic thin film.

There have been continuous demands for the development of organic thin film materials in order to improve the performance, life span or efficiency of an organic light emitting device.

For example, CBP has been mostly widely known so far as a host material of a phosphorescent light emitting body, and an organic light emitting device in which a hole blocking layer such as BCP and BAlq is applied, and an organic light emitting device in which BAlq derivatives are used as a host are well known.

However, existing materials have advantages in the aspect of light emitting properties, but have disadvantages such that the materials change when going through a high-temperature deposition process under vacuum due to a low glass transition temperature and very low thermal stability. In an organic light emitting device, power efficiency=(n/voltage)× current efficiency, therefore, power efficiency is inversely proportional to voltage, and power efficiency needs to be high in order to have low power consumption of the organic light emitting device. In fact, an organic light emitting device that uses a phosphorescent light emitting material has quite high current efficiency (cd/A) compared to an organic light emitting device that uses a fluorescent light emitting material, however, when existing materials such as CBP or BAlq are used as the host of a phosphorescent light emitting material, there are no huge advantages in terms of power efficiency (lm/w) since driving voltage is high compared to that of an organic light emitting device using a fluorescent material. In addition, the life span of an organic light emitting device is not at all satisfactory, therefore, there have been demands for the development of host materials that are more stable and show more excellent performances.

SUMMARY OF THE INVENTION

The present invention provides a novel multicyclic aromatic compound and an organic light emitting device using the same.

The present invention provides a compound of the following Chemical Formula 1:

[Chemical Formula 1]

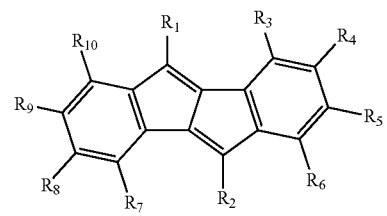

In Chemical Formula 1, $R_1$ and $R_2$ are each independently hydrogen; halogen; substituted or unsubstituted $C_1$-$C_{30}$ alkyl; substituted or unsubstituted $C_6$-$C_{30}$ aryl; substituted or unsubstituted $C_6$-$C_{30}$ aryl in which one or more of substituted or unsubstituted $C_3$-$C_{30}$ cycloalkyl, substituted or unsubstituted $C_3$-$C_{30}$ heteroaryl and substituted or unsubstituted 5-membered to 7-membered heterocycloalkyl are fused; substituted or unsubstituted $C_3$-$C_{30}$ heteroaryl; substituted or unsubstituted $C_3$-$C_{30}$ heteroaryl in which one or more of substituted or unsubstituted $C_3$-$C_{30}$ cycloalkyl, a substituted or unsubstituted $C_6$-$C_{30}$ aromatic ring and substituted or unsubstituted 5-membered to 7-membered heterocycloalkyl are fused; substituted or unsubstituted 5-membered to 7-membered heterocycloalkyl; substituted or unsubstituted 5-membered to 7-membered heterocycloalkyl in which one or more of substituted or unsubstituted $C_3$-$C_{30}$ heterocycloalkyl, a substituted or unsubstituted $C_6$-$C_{30}$ aromatic ring and substituted or unsubstituted $C_3$-$C_{30}$ heteroaryl are fused; substituted or unsubstituted $C_3$-$C_{30}$ cycloalkyl; substituted or unsubstituted $C_3$-$C_{30}$ cycloalkyl in which one or more of substituted or unsubstituted $C_3$-$C_{30}$ heterocycloalkyl, a substituted or unsubstituted $C_6$-$C_{30}$ aromatic ring and substituted or unsubstituted $C_3$-$C_{30}$ heteroaryl are fused; cyano; —$NR_{11}R_{12}$; —$SiR_{13}R_{14}R_{15}$; —$OR_{16}$; —$SR_{17}$; substituted or unsubstituted ($C_6$-$C_{30}$)ar($C_1$-$C_{30}$)alkyl; substituted or unsubstituted alkylamino; $C_3$-$C_{30}$ heteroaryl in which —$SiR_{18}R_{19}R_{20}$ is substituted; substituted or unsubstituted $C_6$-$C_{30}$ arylamino; substituted or unsubstituted $C_2$-$C_{30}$ alkenyl; substituted or unsubstituted $C_2$-$C_{30}$ alkynyl; carboxyl; nitro or hydroxy; or may form a monocyclic or multicyclic aliphatic ring, or a monocyclic or multicyclic aromatic ring, by being linked to an adjacent substituent through $C_3$-$C_{30}$ alkylene or $C_3$-$C_{30}$ alkenylene that does or does not include a fused ring;

$R_{11}$ to $R_{20}$ are each independently hydrogen; substituted or unsubstituted alkyl; substituted or unsubstituted $C_6$-$C_{30}$ aryl; or substituted or unsubstituted $C_3$-$C_{30}$ heteroaryl, or may form a monocyclic or multicyclic aliphatic ring, or a monocyclic or multicyclic aromatic ring, by being linked to an adjacent substituent through $C_3$-$C_{30}$ alkylene or $C_3$-$C_{30}$ alkenylene that does or does not include a fused ring;

the heterocycloalkyl and heteroaryl include one or more heteroatoms selected from N, O, S and Si;

$R_3$ to $R_{10}$ are each independently hydrogen or a monovalent organic substituent, $R_3$ and $R_4$, $R_4$ and $R_5$, $R_5$ and $R_6$, $R_7$ and $R_8$, $R_8$ and $R_9$ or $R_9$ and $R_{10}$ may form a monocyclic or multicyclic aliphatic ring, or a monocyclic or multicyclic aromatic ring, by being linked through $C_3$-$C_{30}$ alkylene or $C_3$-$C_{30}$ alkenylene that does or does not include a fused ring.

The present invention also provides an organic light emitting device that includes a first electrode, a second electrode, and one or more organic material layers provided between the first electrode and the second electrode, wherein one or more layers of the organic material layers include the compound of Chemical Formula 1.

According to one embodiment, the organic material layer that includes the compound of Chemical Formula 1 is a light emitting layer.

According to another embodiment, the organic material layer that includes the compound of Chemical Formula 1 further includes a light emitting dopant.

According to still another embodiment, the organic material layer that includes the compound of Chemical Formula 1 further includes a phosphorescent dopant.

ADVANTAGEOUS EFFECTS

A Compound according to the present invention may be used as the material of an organic material layer of an organic light emitting device. The compound may be used as a hole injection material, a hole transfer material, a light emitting material, an electron transfer material, an electron injection material or the like in an organic light emitting device. In particular, the compound may be used as a light emitting material of an organic light emitting device. In addition, the compound may be used as a host material, particularly, a phosphorescent host material of the light emitting layer of an organic light emitting device.

When the compound according to the present invention is used as a light emitting material, there are advantages in that the material has excellent light emitting efficiency compared to existing materials, long life span of a device can be expected due to excellent life span properties of the material, and an organic light emitting device having improved power consumption can be manufactured by inducing the enhancement of power efficiency. In addition, the compound can accomplish appropriate color coordinates. Therefore, by using the compound according to the present invention, an organic light emitting device having high efficiency and long life span can be provided.

BRIEF DESCRIPTION OF THE DRAWINGS

FIGS. 1 to 3 illustrate the laminating order of electrodes and organic material layers of an organic light emitting device according to embodiments of the present invention.

DETAILED DESCRIPTION OF THE EMBODIMENTS

Hereinafter, the present invention will be described in detail.

A compound according to the present invention may be represented by Chemical Formula 1. The compound according to the present invention may be used as the material of an organic material layer of an organic light emitting device depending on the structural and physical properties of a core structure. Specifically, Chemical Formula 1 has dibenzopentalene as the core structure. Dibenzopentalene is an antiaromatic molecule having a pentalene skeleton. According to a Hückel rule, all the carbon molecules within the skeleton share π electrons, and the molecule having 4n number of π electrons has 'antiaromaticity', and in this structure, reactivity improves due to the mobility improvement of the π electrons within the structure having a covalent bonding. In addition, the molecule can have aromaticity with excellent stability due to easy modification to a divalent anion form. Furthermore, the molecule having pentalene as a skeleton has high stability disregard of its antiaromaticity, therefore, the molecule is useful in preparing transition metal complexes having a sandwich form, and is useful as the material of an organic semiconductor or a dye having high oxidation/reduction potential as a π electron conjugation molecule having a trapezoid form. In this respect, the core structure of Chemical Formula 1 is different from the structure of dihydropentalene at the position of π electrons as shown below.

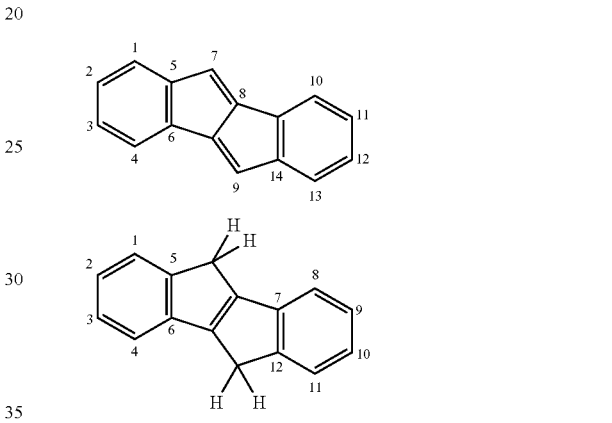

In "substituted or unsubstituted" of $R_1$ to $R_{10}$, substituted means being each independently further substituted with one or more selected from the group consisting of deuterium, halogen, $C_1$-$C_{30}$ alkyl in which halogen is substituted or unsubstituted, $C_6$-$C_{30}$ aryl, $C_3$-$C_{30}$ heteroaryl in which $C_6$-$C_{30}$ aryl is substituted or unsubstituted, 5-membered to 7-membered heterocycloalkyl, 5-membered to 7-membered heterocycloalkyl in which one or more aromatic rings are fused, $C_3$-$C_{30}$ cycloalkyl, $C_3$-$C_{30}$ cycloalkyl in which one or more aromatic rings are fused, tri($C_1$-$C_{30}$)alkylsilyl, di($C_1$-$C_{30}$)alkyl($C_6$-$C_{30}$)arylsilyl, tri($C_6$-$C_{30}$)arylsilyl, $C_2$-$C_{30}$ alkenyl, $C_2$-$C_{30}$ alkynyl, cyano, carbazolyl, —$NR_{31}R_{32}$, —$SiR_{33}R_{34}R_{35}$, —$OR_{36}$, $SR_{37}$, ($C_6$-$C_{30}$)ar($C_1$-$C_{30}$)alkyl, ($C_1$-$C_{30}$)alkyl($C_6$-$C_{30}$)aryl, alkyloxy, alkylthio, $C_6$-$C_{30}$ aryloxy, $C_6$-$C_{30}$ arylthio, carboxyl, nitro or hydroxy, and $R_{31}$ to $R_{37}$ are each independently hydrogen, $C_1$-$C_{30}$ alkyl, $C_6$-$C_{30}$ aryl or $C_3$-$C_{30}$ heteroaryl, or may form a monocyclic or multicyclic aliphatic ring, or a monocyclic or multicyclic aromatic ring, by being linked to an adjacent substituent through $C_3$-$C_{30}$ alkylene or $C_3$-$C_{30}$ alkenylene that does or does not include a fused ring.

The substituent including "alkyl", "alkoxy" and additional "alkyl" parts, which is described in the present specification, includes all linear or branched forms.

In the present specification, cycloalkyl includes monocyclic or multicyclic having 3 to 30 carbon atoms, and specifically, includes all substituted or unsubstituted adamantyl, or substituted or unsubstituted $C_7$-$C_{30}$ bicycloalkyl. Herein, multicyclic means a group in which cycloalkyl is directly bonded to or condensed with other ring groups. Herein, the other ring groups may be cycloalkyl, but may also be other types of ring groups, for example, heterocycloalkyl, an aromatic ring, heteroaryl or the like. The number of cycloalkyl carbon atoms may be 3 to 30, specifically 3 to 20, and more specifically 5 to 12.

In the present specification, heterocycloalkyl includes S, O or N as a heteroatom, includes monocyclic or multicyclic having 2 to 30 carbon atoms, and may be further substituted with other substituents. Herein multicyclic means a group in which heterocycloalkyl is directly bonded to or condensed with other ring groups. Herein, the other ring groups may be heterocycloalkyl, but may also be other types of ring groups, for example, cycloalkyl, an aromatic ring, heteroaryl or the like. The number of heterocycloalkyl carbon atoms may be 2 to 30, specifically 2 to 20, and more specifically 3 to 12.

In the present specification, aryl is an organic radical derived from aromatic hydrocarbon by removing one hydrogen, and includes a single or fused ring including a 4-membered to 7-membered ring and more preferably a 5-membered or 6-membered ring, and also includes a structure in which one or more aryl are bonded through chemical bonding. Specific examples of the aryl include phenyl, naphthyl, biphenyl, anthryl, indenyl, fluorenyl, phenanthryl, triphenylenyl, pyrenyl, perylenyl, chrysenyl, naphthacenyl, fluoranthenyl, or the like, but are not limited thereto.

In the present specification, heteroaryl means an aryl group in which 1 to 4 heteroatoms selected from N, O and S are included as an aromatic ring skeleton atoms, and the rest of the aromatic ring skeleton atoms is carbon, and includes 5- to 6-membered monocyclic heteroaryl or multicyclic heteroaryl condensed with one or more benzene rings, and may be partially saturated. In addition, the heteroaryl in the present specification also includes a structure in which one or more heteroaryl are bonded through chemical bonding. The heteroaryl group includes a divalent aryl group in which the heteroatom within the ring is oxidized or becomes 4-membered, and for example, an N-oxide or quaternary salt is formed. Specific examples of the heteroaryl includes moonocyclic heteroaryl such as furyl, thienyl, pyrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl or pyridazinyl, multicyclic heteroaryl such as benzofuryl, benzothienyl, isobenzofuryl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinolizinyl, quinoxalinyl, carbazolyl, phenanthridinyl or benzodioxolyl, a corresponding N-oxide thereof such as pyridyl N-oxide or quinolyl N-oxide, a quaternary salt thereof, or the like, but are not limited thereto.

In addition, a "$C_1$-$C_{30}$ alkyl" group described in the present specification includes $C_1$-$C_{20}$ alkyl or $C_1$-$C_{10}$ alkyl, a "$C_6$-$C_{30}$ aryl" group includes $C_6$-$C_{20}$ aryl or $C_6$-$C_{12}$ aryl. A "$C_3$-$C_{30}$ heteroaryl" group includes $C_3$-$C_{20}$ heteroaryl or $C_3$-$C_{12}$ heteroaryl, a "$C_3$-$C_{30}$ cycloalkyl" group includes $C_3$-$C_{20}$ cycloalkyl or $C_3$-$C_7$ cycloalkyl. A "$C_2$-$C_{30}$ alkenyl or alkynyl" group includes $C_2$-$C_{20}$ alkenyl or alkynyl, or $C_2$-$C_{10}$ alkenyl or alkynyl.

In the present specification, halogen includes F, Cl, Br and I.

According to one embodiment of the present invention, $R_1$ to $R^{10}$ are each independently hydrogen, halogen, substituted or unsubstituted $C_1$-$C_{30}$ alkyl, substituted or unsubstituted $C_6$-$C_{30}$ aryl, substituted or unsubstituted $C_6$-$C_{30}$ aryl in which one or more of substituted or unsubstituted $C_3$-$C_{30}$ cycloalkyls are fused, substituted or unsubstituted $C_3$-$C_{30}$ heteroaryl, substituted or unsubstituted 5-membered to 7-membered heterocycloalkyl, 5-membered to 7-membered heterocycloalkyl in which one or more substituted or unsubstituted aromatic rings are fused, substituted or unsubstituted $C_3$-$C_{30}$ cycloalkyl, $C_3$-$C_{30}$ cycloalkyl in which one or more substituted or unsubstituted aromatic rings are fused, cyano, —$NR_{11}R_{12}$, —$SiR_{13}R_{14}R_{15}$, —$OR_{16}$, —$SR_{17}$, substituted or unsubstituted $(C_6$-$C_{30})$ar$(C_1$-$C_{30})$alkyl, substituted or unsubstituted alkylamino, $C_3$-$C_{30}$ heteroaryl in which —$SiR_{18}R_{19}R_{20}$ is substituted, substituted or unsubstituted $C_6$-$C_{30}$ arylamino, substituted or unsubstituted $C_2$-$C_{30}$ alkenyl, substituted or unsubstituted $C_2$-$C_{30}$ alkynyl, carboxyl, nitro or hydroxy, or may form a monocyclic or multicyclic aliphatic ring, or a monocyclic or multicyclic aromatic ring, by being linked to an adjacent substituent through $C_3$-$C_{30}$ alkylene or $C_3$-$C_{30}$ alkenylene that does or does not include a fused ring;

$R_{11}$ to $R_{20}$ are each independently substituted or unsubstituted $C_1$-$C_{30}$ alkyl, substituted or unsubstituted $C_6$-$C_{30}$ aryl or substituted or unsubstituted $C_3$-$C_{30}$ heteroaryl, or may form a monocyclic or multicyclic aliphatic ring, or a monocyclic or multicyclic aromatic ring, by being linked to an adjacent substituent through $(C_3$-$C_{30})$alkylene or $(C_3$-$C_{30})$alkenylene that does or does not include a fused ring;
the heterocycloalkyl and heteroaryl include one or more heteroatoms selected from N, O, S and Si.

According to one embodiment of the present invention, $R_1$ to $R_{10}$ are each independently selected from hydrogen, halogen, alkyl such as methyl, ethyl, propyl, butyl, pentyl, hexyl, ethylhexyl, heptyl or octyl, aryl such as phenyl, naphthyl, fluorenyl, biphenyl, phenanthryl, terphenyl, pyrenyl, perylenyl, spirobifluorenyl, fluoranthenyl, chrysenyl or triphenylenyl, aryl in which one or more cycloalkyl are fused, such as 1,2-dihydroacenaphthyl, heteroaryl such as dibenzothiophenyl, dibenzofuryl, carbazolyl, pyridyl, furyl, thienyl, quinolyl, triazinyl, pyrimidinyl, pyridazinyl, quinoxalinyl or phenanthrolinyl, heterocycloalkyl in which one or more aromatic rings are fused, such as benzopyrrolidino, benzopiperidino, dibenzomorpholino or dibenzoazepino, or amino in which aryl such as phenyl, naphthyl, fluorenyl, biphenyl, phenanthryl, terphenyl, pyrenyl, perylenyl, spirobifluorenyl, fluoranthenyl, chrysenyl or triphenylenyl, or heteroaryl such as dibenzothiophenyl, dibenzofuryl, carbazolyl, pyridyl, furyl, thienyl, quinolyl, triazinyl, pyrimidinyl, pyridazinyl, quinoxalinyl, phenanthrolinyl is substituted, aryloxy such as biphenyloxy, arylthio such as biphenylthio, aralkyl such as biphenylmethyl or triphenylmethyl, carboxyl, nitro or hydroxy, but $R_1$ to $R_{10}$ are not limited thereto, and may be further substituted as in Chemical Formula 1.

According to one embodiment of the present invention, $R_1$ and $R_2$ are each independently halogen; substituted or unsubstituted $C_1$-$C_{30}$ alkyl; substituted or unsubstituted $C_6$-$C_{30}$ aryl; substituted or unsubstituted $C_6$-$C_{30}$ aryl in which one or more of substituted or unsubstituted $C_3$-$C_{30}$ cycloalkyl, substituted or unsubstituted $C_3$-$C_{30}$ heteroaryl and substituted or unsubstituted 5-membered to 7-membered heterocycloalkyl are fused; substituted or unsubstituted $C_3$-$C_{30}$ heteroaryl; substituted or unsubstituted $C_3$-$C_{30}$ heteroaryl in which one or more of substituted or unsubstituted $C_3$-$C_{30}$ cycloalkyl, a substituted or unsubstituted $C_6$-$C_{30}$ aromatic ring and substituted or unsubstituted 5-membered to 7-membered heterocycloalkyl are fused; substituted or unsubstituted 5-membered to 7-membered heterocycloalkyl; substituted or unsubstituted 5-membered to 7-membered heterocycloalkyl in which one or more of substituted or unsubstituted $C_3$-$C_{30}$ heterocycloalkyl, a substituted or unsubstituted $C_6$-$C_{30}$ aromatic ring and substituted or unsubstituted $C_3$-$C_{30}$ heteroaryl are fused; substituted or unsubstituted $C_3$-$C_{30}$ cycloalkyl; substituted or unsubstituted $C_3$-$C_{30}$ cycloalkyl in which one or more of substituted or unsubstituted $C_3$-$C_{30}$ heterocycloalkyl, a substituted or unsubstituted $C_6$-$C_{30}$ aromatic ring and substituted or unsubstituted $C_3$-$C_{30}$ heteroaryl are fused; cyano; —$NR_{11}R_{12}$; —$OR_{16}$; —$SR_{17}$; substituted or unsubstituted ($C_6$-$C_{30}$)ar($C_1$-$C_{30}$)alkyl; substituted or unsubstituted alkylamino; $C_3$-$C_{30}$ heteroaryl in which —$SiR_{18}R_{19}R_{20}$ is substituted; substituted or unsubstituted $C_6$-$C_{30}$ arylamino; substituted or unsubstituted $C_2$-$C_{30}$ alkenyl; substituted or unsubstituted $C_2$-$C_{30}$ alkynyl; carboxyl; nitro or hydroxy; or may form a monocyclic or multicyclic aliphatic ring, or a monocyclic or multicyclic aromatic ring, by being linked to an adjacent substituent through $C_3$-$C_{30}$ alkylene or $C_3$-$C_{30}$ alkenylene that does or does not include a fused ring.

According to one embodiment of the present invention, at least one of $R_1$ and $R_2$ has seven or more carbons in ring members.

According to one embodiment of the present invention, at least one of $R_1$ and $R_2$ includes two or more rings.

According to one embodiment of the present invention, $R_1$ and $R_2$ are different from each other.

According to one embodiment of the present invention, at least one of $R_1$ and $R_2$ is $C_1$-$C_{30}$ alkyl.

According to one embodiment of the present invention, $R_1$ and $R_2$ may be selected from hydrogen, alkyl, phenyl, naphthyl, anthracenyl, phenanthrenyl, pyrenyl, phenyl- or alkyl-substituted fluorenyl, phenyl-substituted or unsubstituted carbazolyl, naphthyl-substituted phenyl, biphenyl, indenyl, acenaphthylenyl, fluoranthenyl, phenyl-substituted naphthyl, indolyl, benzoxazolyl, benzothiazolyl and arylamine-substituted phenyl.

According to one embodiment of the present invention, $R_1$ and $R_2$ may be selected from alkyl, naphthyl, anthracenyl, phenanthrenyl, pyrenyl, phenyl- or alkyl-substituted fluorenyl, phenyl-substituted or unsubstituted carbazolyl, naphthyl-substituted phenyl, biphenyl, indenyl, acenaphthylenyl, fluoranthenyl, phenyl-substituted naphthyl, indolyl, benzoxazolyl, benzothiazolyl and arylamine-substituted phenyl.

In Chemical Formula 1, $R_3$ to $R_{10}$ are each independently hydrogen; or a monovalent organic substituent. As specific examples, $R_3$ to $R_{10}$ are each independently hydrogen; halogen; substituted or unsubstituted $C_1$-$C_{30}$ alkyl; substituted or unsubstituted $C_6$-$C_{30}$ aryl; substituted or unsubstituted $C_6$-$C_{30}$ aryl in which one or more of substituted or unsubstituted $C_3$-$C_{30}$ cycloalkyl, substituted or unsubstituted $C_3$-$C_{30}$ heteroaryl and substituted or unsubstituted 5-membered to 7-membered heterocycloalkyl are fused; substituted or unsubstituted $C_3$-$C_{30}$ heteroaryl; substituted or unsubstituted $C_3$-$C_{30}$ heteroaryl in which one or more of substituted or unsubstituted $C_3$-$C_{30}$ cycloalkyl, a substituted or unsubstituted $C_6$-$C_{30}$ aromatic ring and substituted or unsubstituted 5-membered to 7-membered heterocycloalkyl are fused; substituted or unsubstituted 5-membered to 7-membered heterocycloalkyl; substituted or unsubstituted 5-membered to 7-membered heterocycloalkyl in which one or more of substituted or unsubstituted $C_3$-$C_{30}$ heterocycloalkyl, a substituted or unsubstituted $C_6$-$C_{30}$ aromatic ring and substituted or unsubstituted $C_3$-$C_{30}$ heteroaryl are fused; substituted or unsubstituted $C_3$-$C_{30}$ cycloalkyl; substituted or unsubstituted $C_3$-$C_{30}$ cycloalkyl in which one or more of substituted or unsubstituted $C_3$-$C_{30}$ heterocycloalkyl, a substituted or unsubstituted $C_6$-$C_{30}$ aromatic ring and substituted or unsubstituted $C_3$-$C_{30}$ heteroaryl are fused; cyano; —$NR_{11}R_{12}$; —$SiR_{13}R_{14}R_{15}$; —$OR_{16}$; —$SR_{17}$; substituted or unsubstituted ($C_6$-$C_{30}$)ar($C_1$-$C_{30}$)alkyl; substituted or unsubstituted $C_1$-$C_{30}$ alkylamino; $C_3$-$C_{30}$ heteroaryl in which —$SiR_{18}R_{19}R_{20}$ is substituted; substituted or unsubstituted $C_6$-$C_{30}$ arylamino; substituted or unsubstituted $C_2$-$C_{30}$ alkenyl; substituted or unsubstituted $C_2$-$C_{30}$ alkynyl; carboxyl; nitro or hydroxy; or may form a monocyclic or multicyclic aliphatic ring, or a monocyclic or multicyclic aromatic ring, by being linked to an adjacent substituent through $C_3$-$C_{30}$ alkylene or $C_3$-$C_{30}$ alkenylene that does or does not include a fused ring.

According to one embodiment of the present invention, $R_3$ to $R_{10}$ are each independently hydrogen; substituted or unsubstituted alkyl; substituted or unsubstituted $C_6$-$C_{30}$ aryl; or may form a monocyclic or multicyclic aliphatic ring, or a monocyclic or multicyclic aromatic ring, by being linked to an adjacent substituent through $C_3$-$C_{30}$ alkylene or $C_3$-$C_{30}$ alkenylene that does or does not include a fused ring.

According to one embodiment of the present invention, $R_3$ to $R_{10}$ are each independently hydrogen; methyl or phenyl, or may form a phenyl group with an adjacent substituent.

According to one embodiment of the present invention, $R_5$ and $R_9$ are each independently hydrogen; methyl or phenyl, or form a phenyl group with an adjacent substituent, and $R_3$, $R_4$, $R_6$, $R_7$, $R_8$ and $R_{10}$ are hydrogen.

According to one embodiment of the present invention, $R_4$, $R_5$, $R_8$ and $R_9$ are each independently hydrogen; methyl or phenyl, or form a phenyl group with an adjacent substituent, and $R_3$, $R_6$, $R_7$ and $R_{10}$ are hydrogen.

According to one embodiment of the present invention, Chemical Formula 1 may be represented by any one of Chemical Formulae 2 to 9.

[Chemical Formula 2]

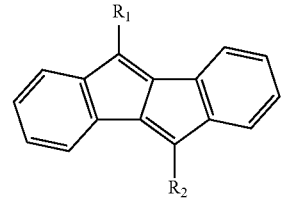

[Chemical Formula 3]

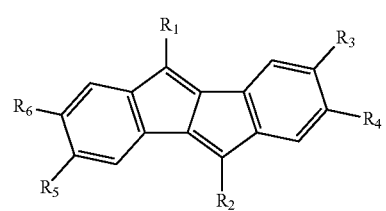

[Chemical Formula 4]

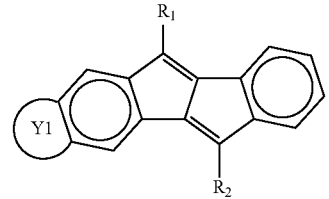

-continued

[Chemical Formula 5]

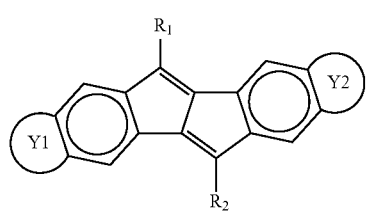

[Chemical Formula 6]

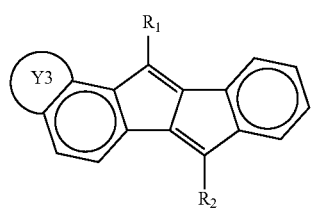

[Chemical Formula 7]

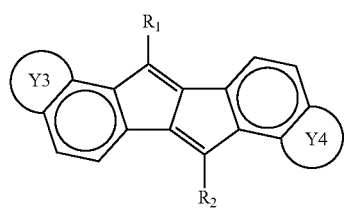

[Chemical Formula 8]

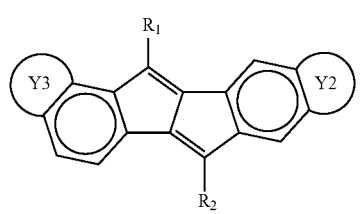

[Chemical Formula 9]

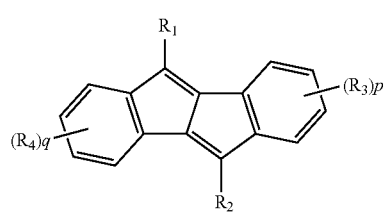

In Chemical Formulae 2 to 9, $R_1$, $R_2$, $R_3$ and $R_4$ are the same as those defined in claim 1, p and q each independently represent an integer of 1 to 4, Y1 to Y4 represent one of substituted or unsubstituted $C_3$-$C_{30}$ cycloalkyl, substituted or unsubstituted $C_3$-$C_{30}$ heteroaryl, substituted or unsubstituted 5-membered to 7-membered heterocycloalkyl and substituted or unsubstituted $C_6$-$C_{30}$ aryl, or a ring in which two or more of these rings are fused.

According to one embodiment, Chemical Formula 1 may be illustrated by the following structural formulae, however, the scope of the present invention is not limited thereto.

1

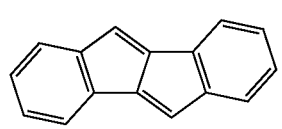

-continued

2

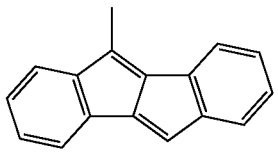

3

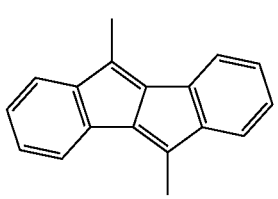

4

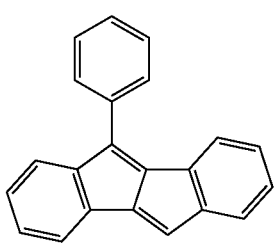

5

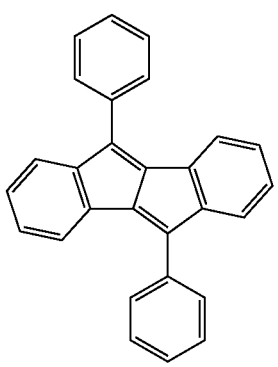

6

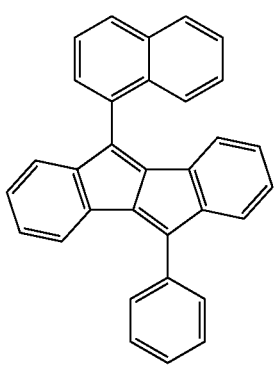

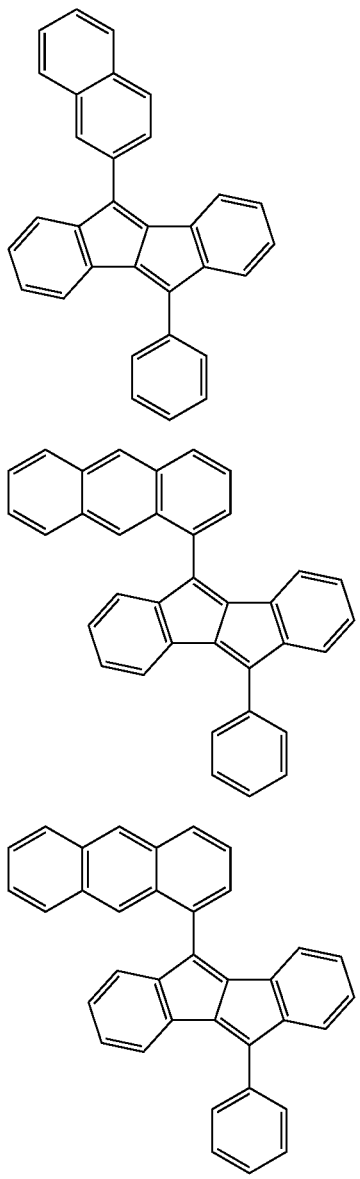
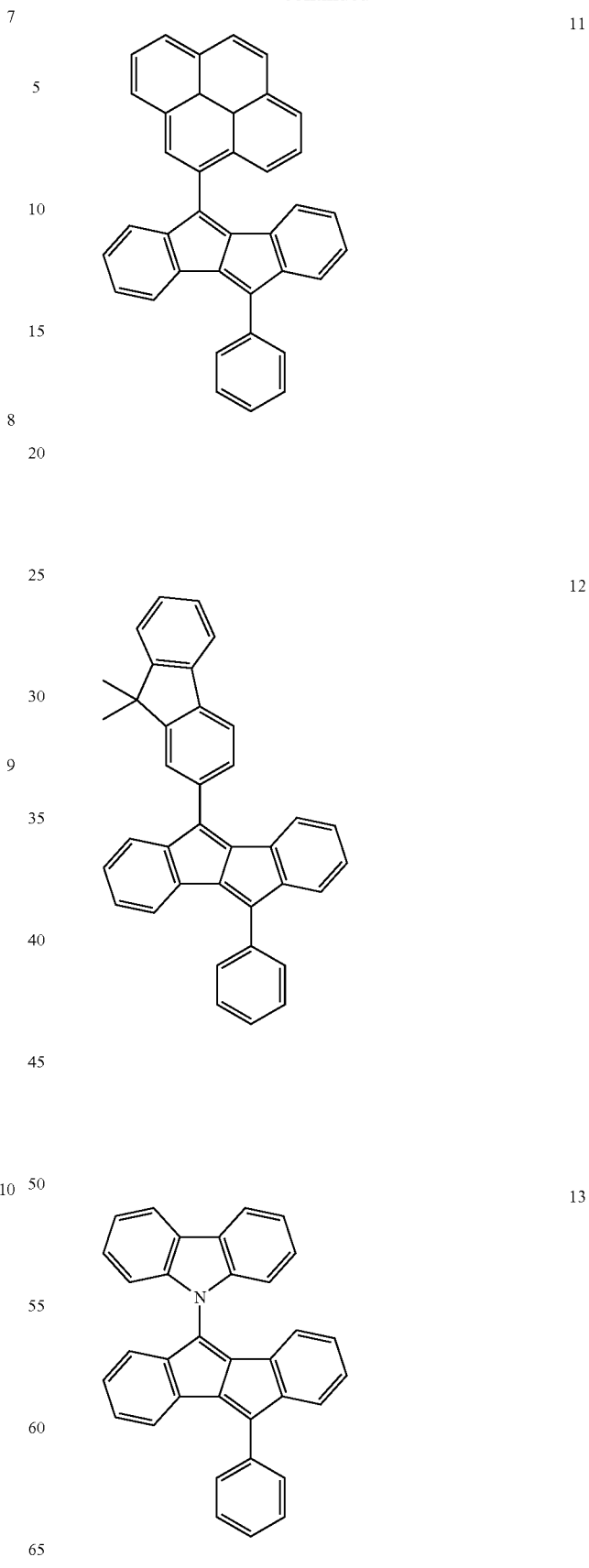

14
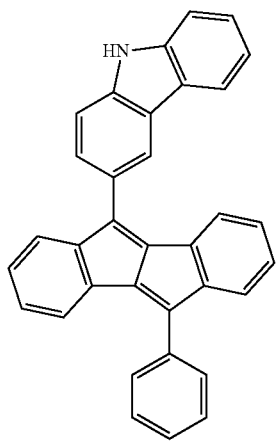
15
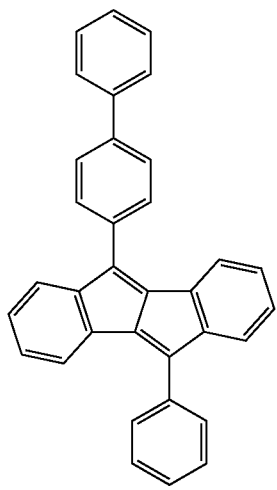
16
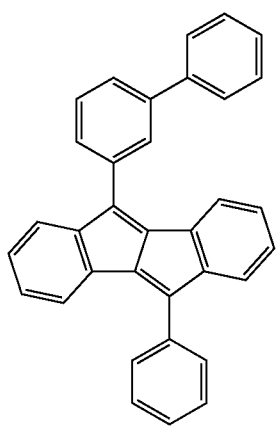
17
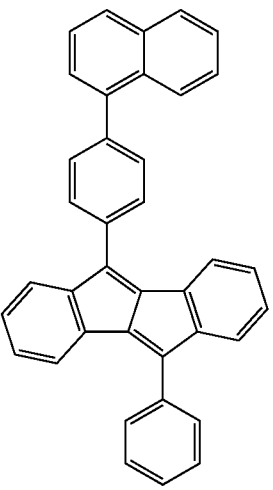
18
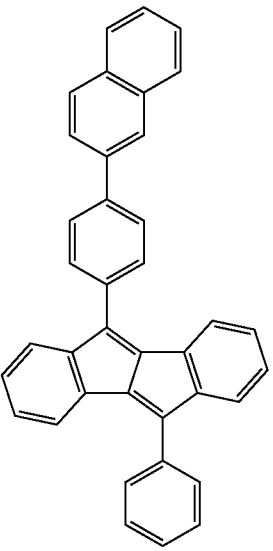
19
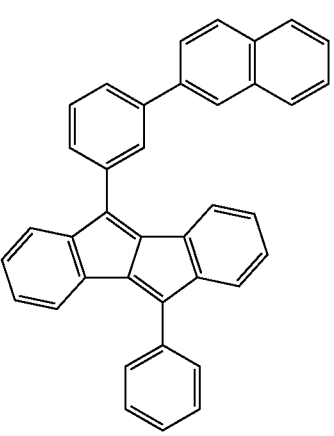

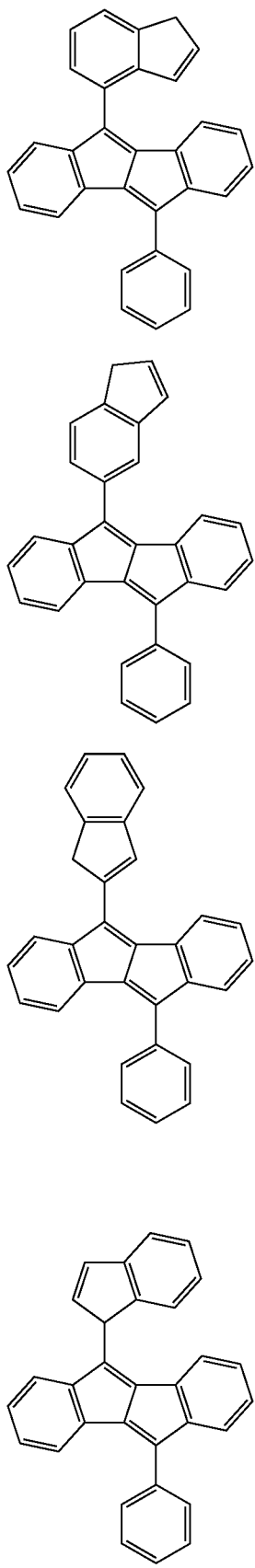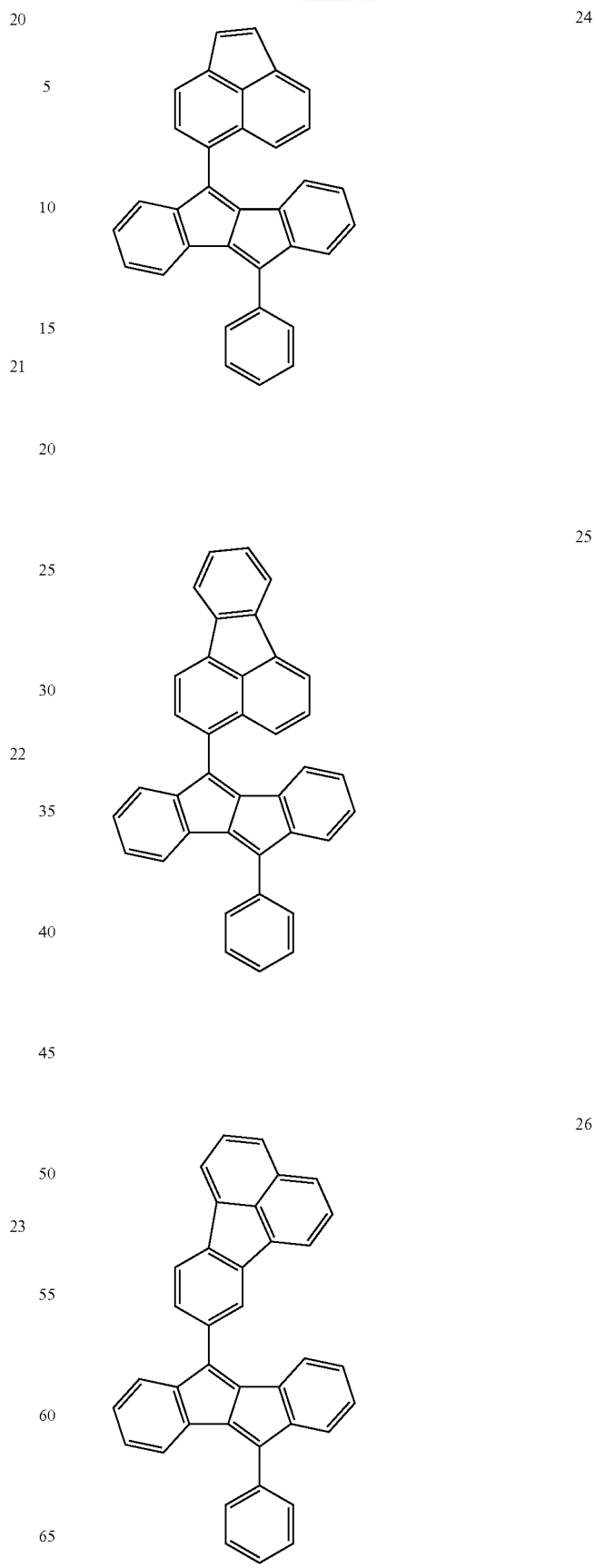

27
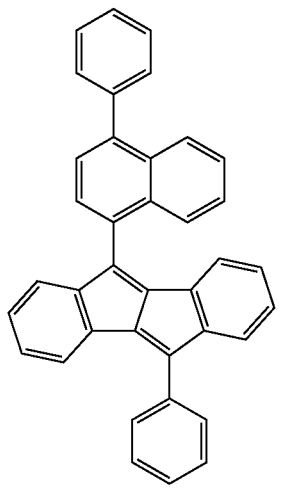
28
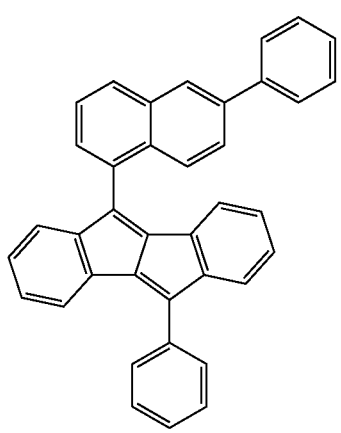
29
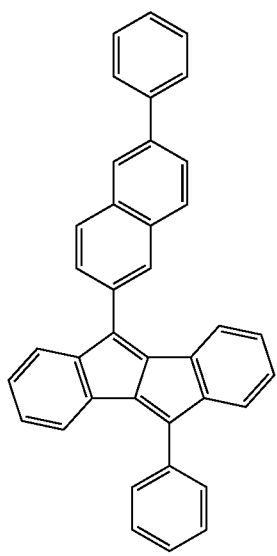
30
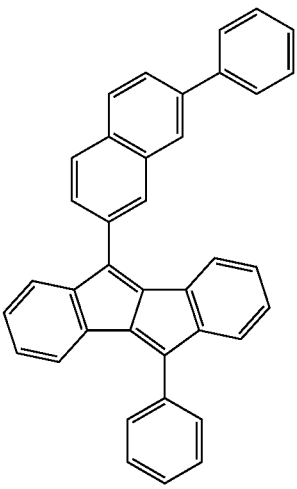
31
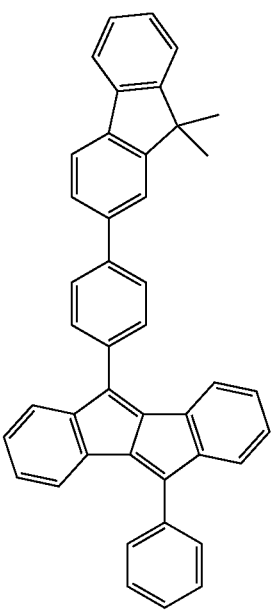
32
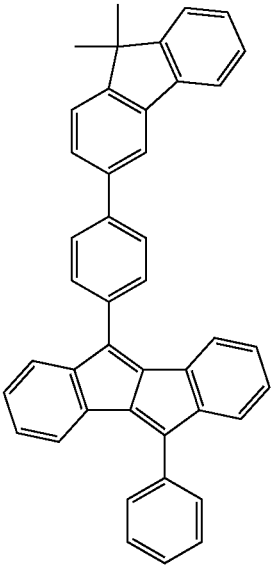

33
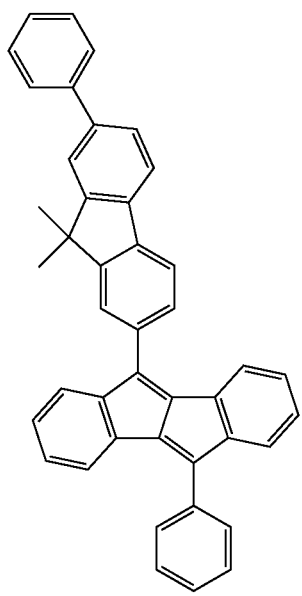
34
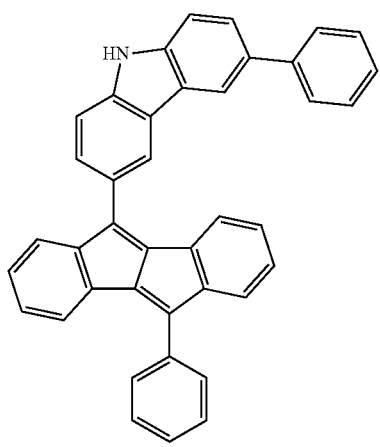
35
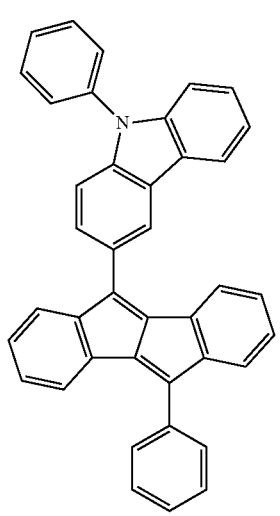
36
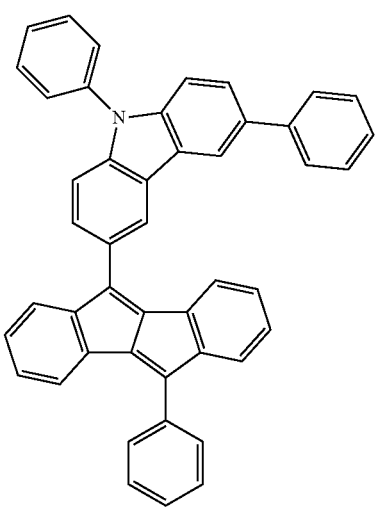
37
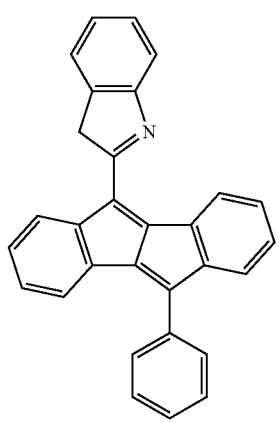
38
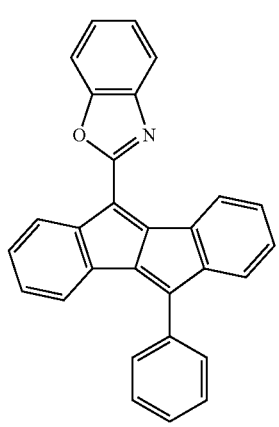

39
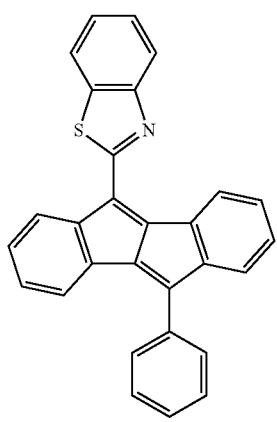
40
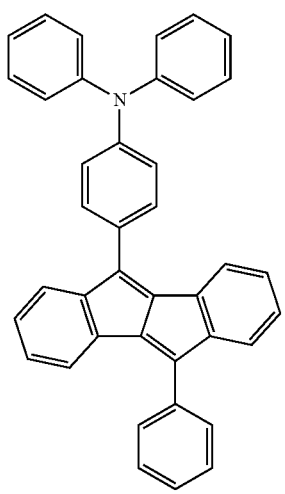
41
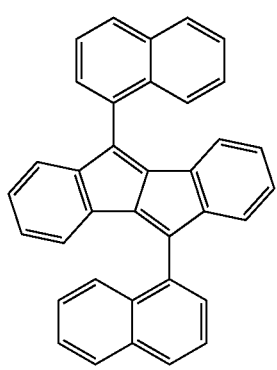
42
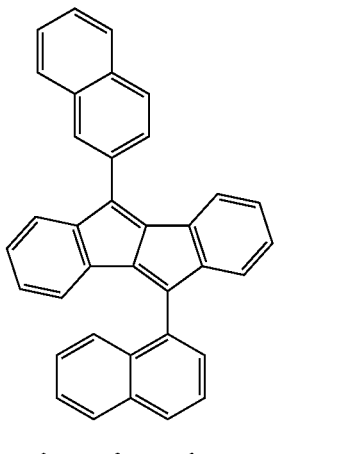
43
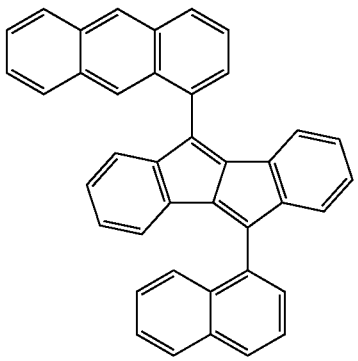
44
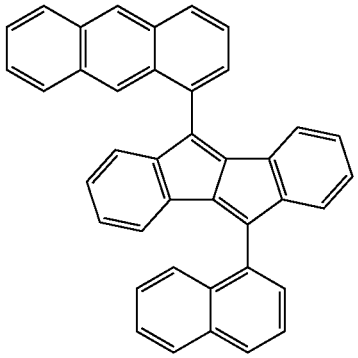
45
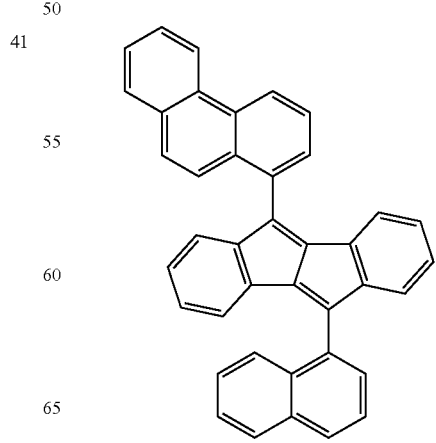

46
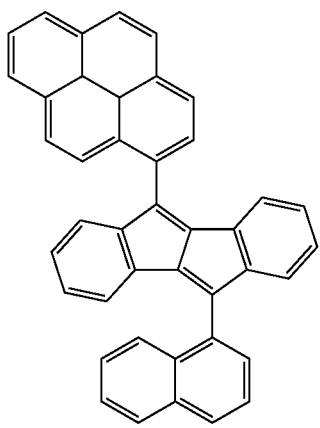
49
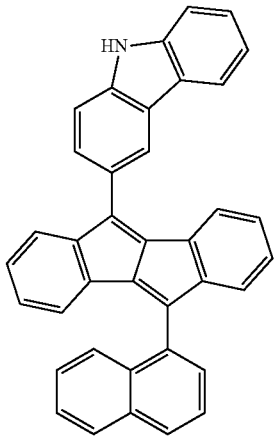
47
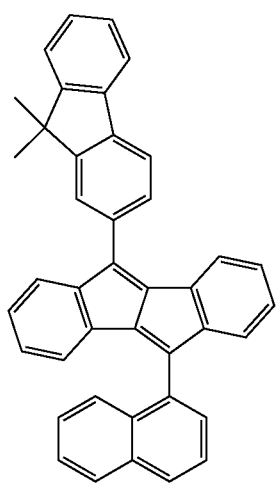
50
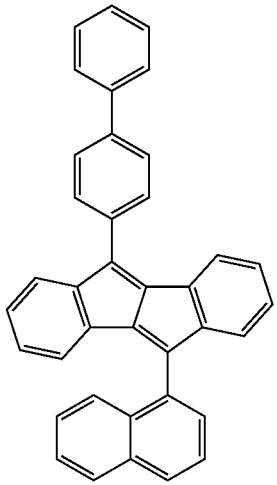
48
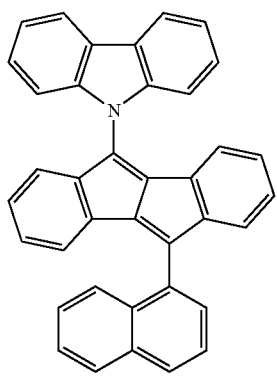
51
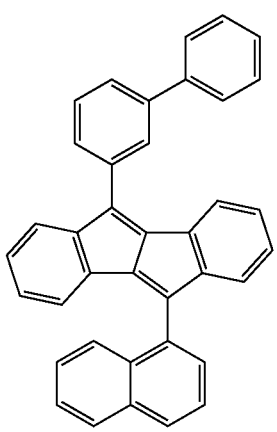

52
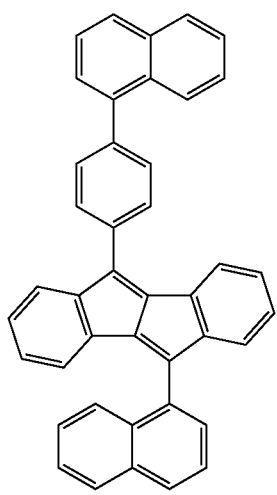
53
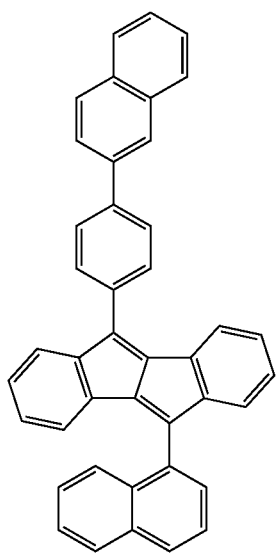
54
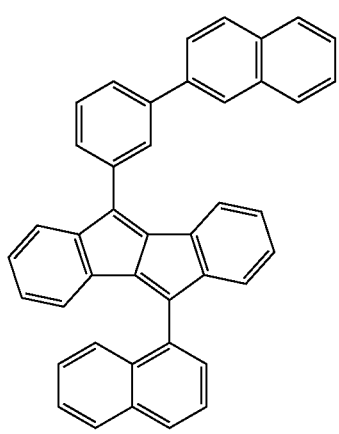
55
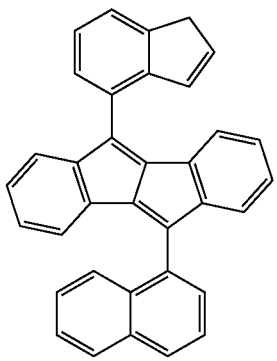
56
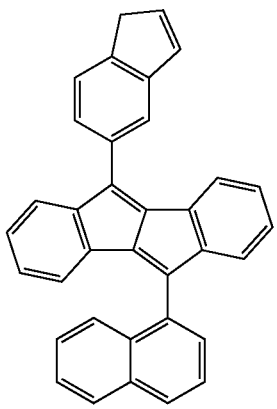
57
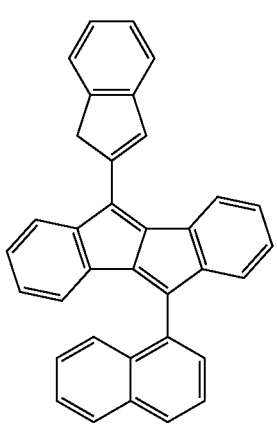
58
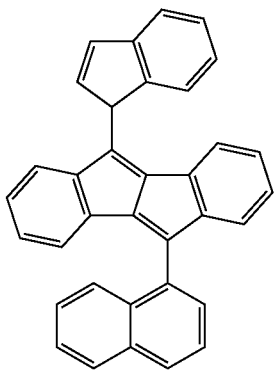

59
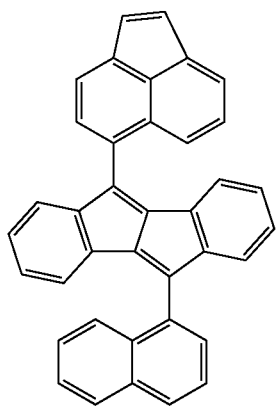
60
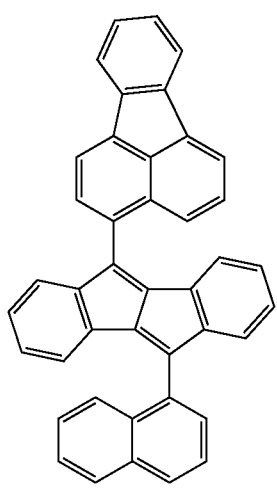
61
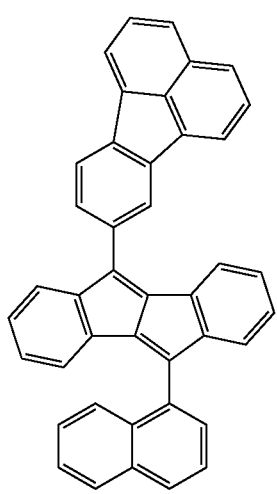
62
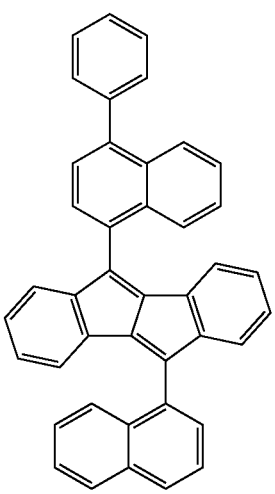
63
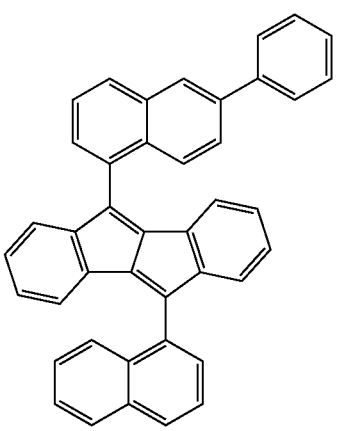
64
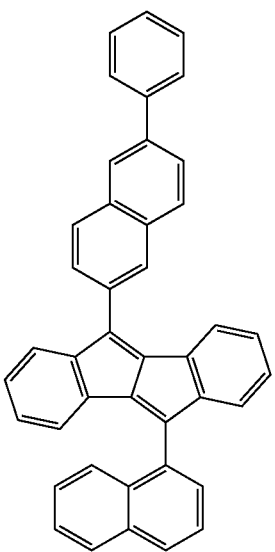

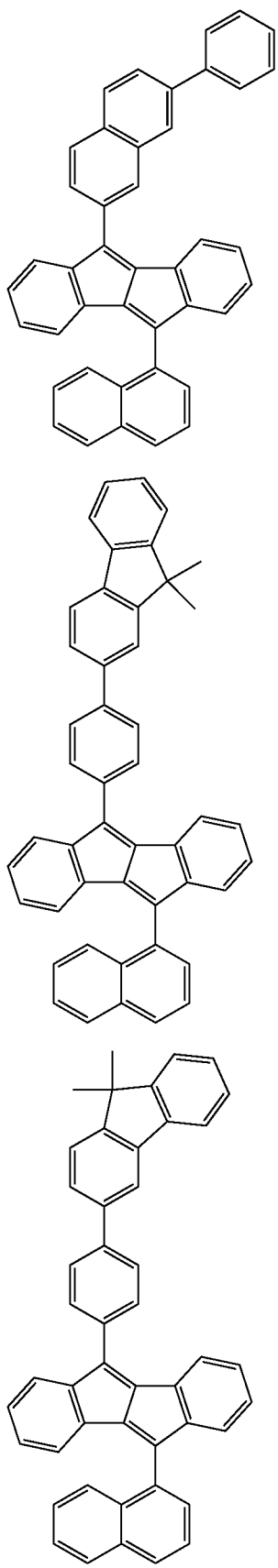
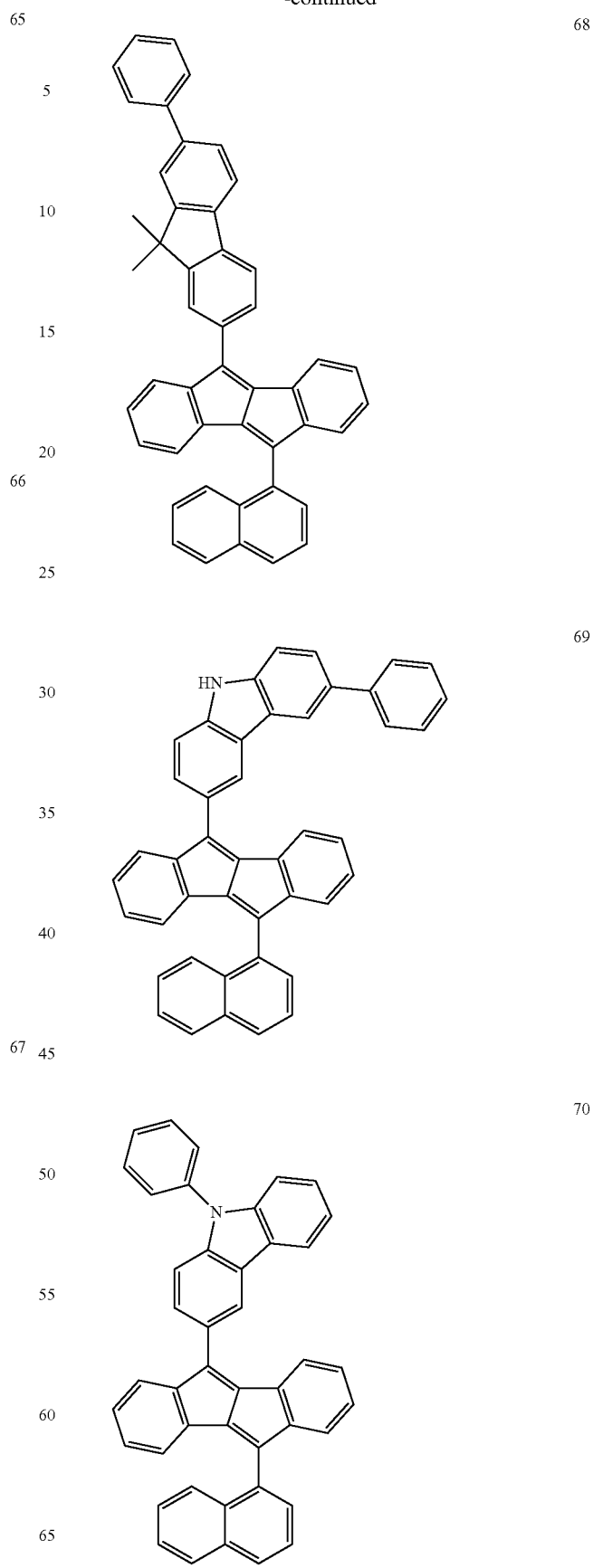

71
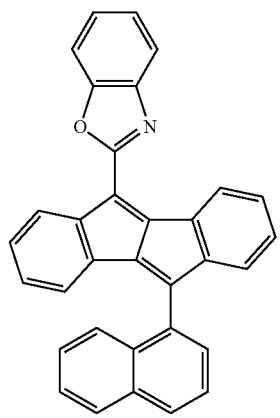
72
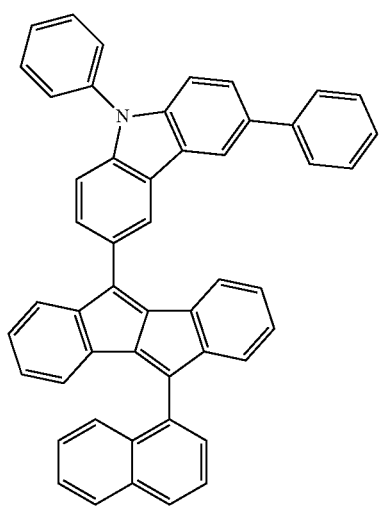
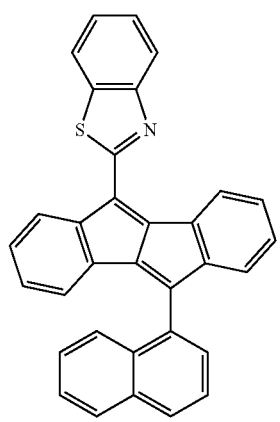
73
74
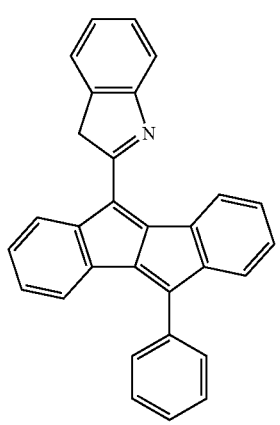
75
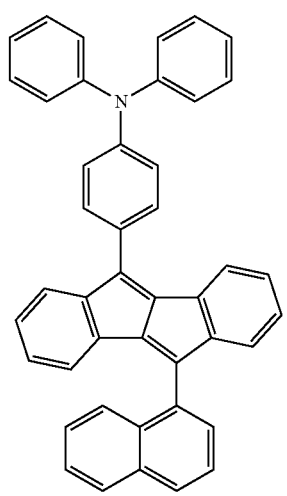
76
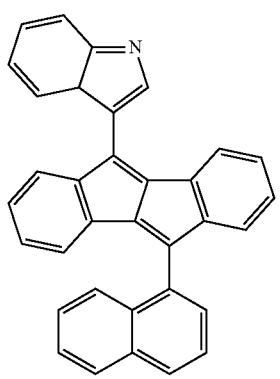

-continued
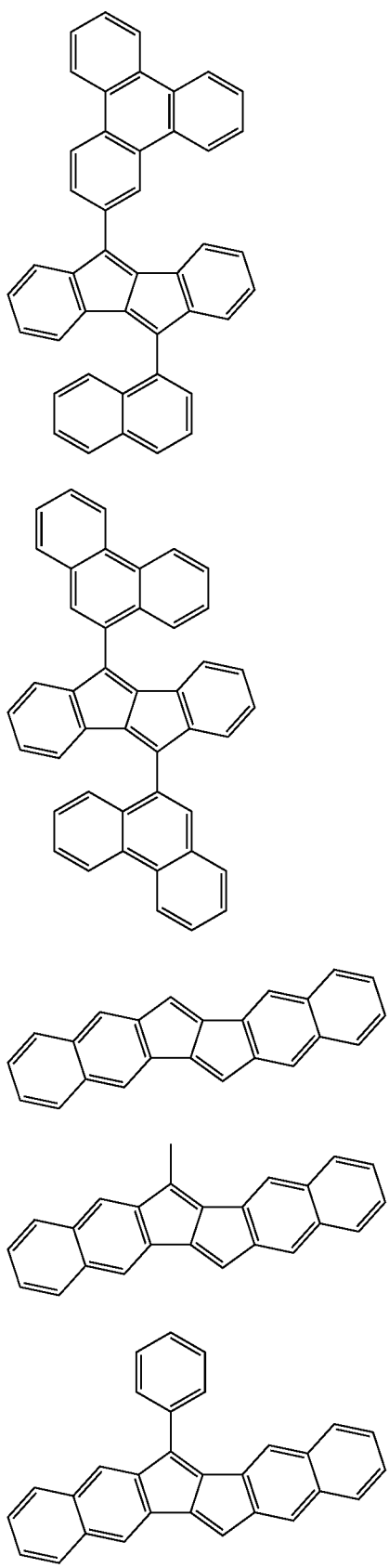
77
78
79
80
81
-continued
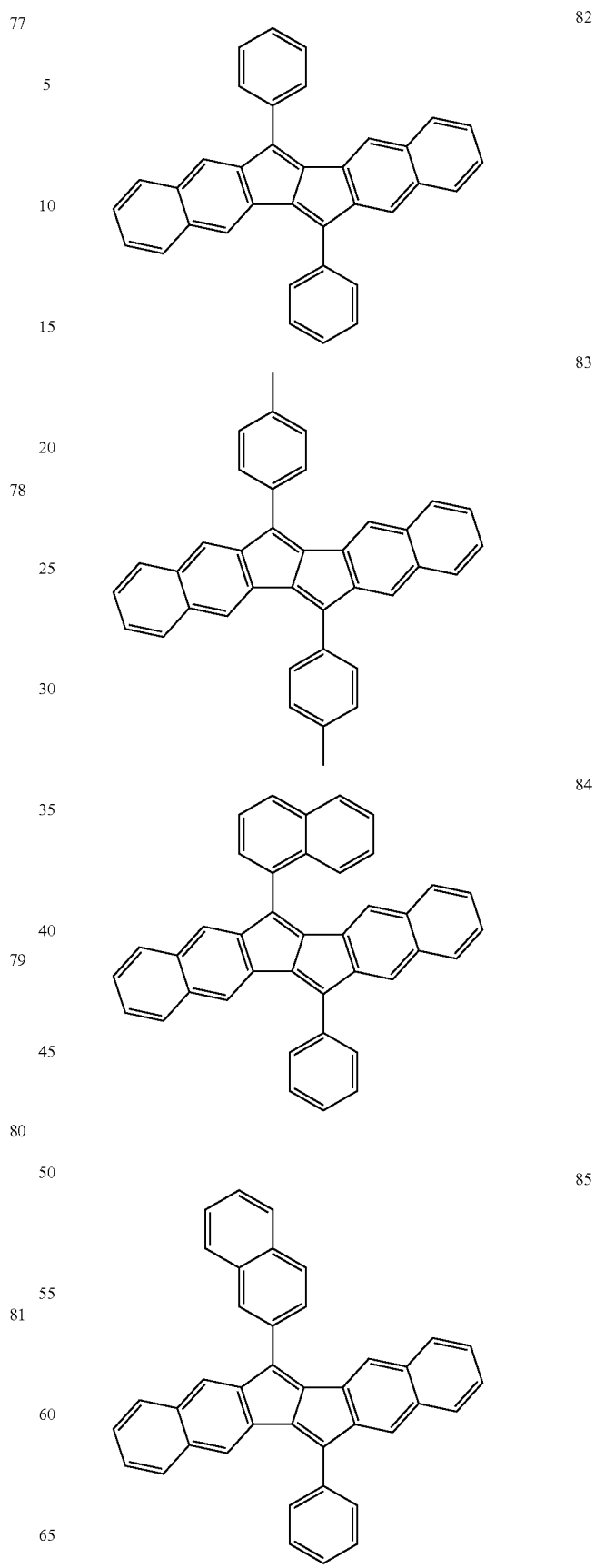
82
83
84
85

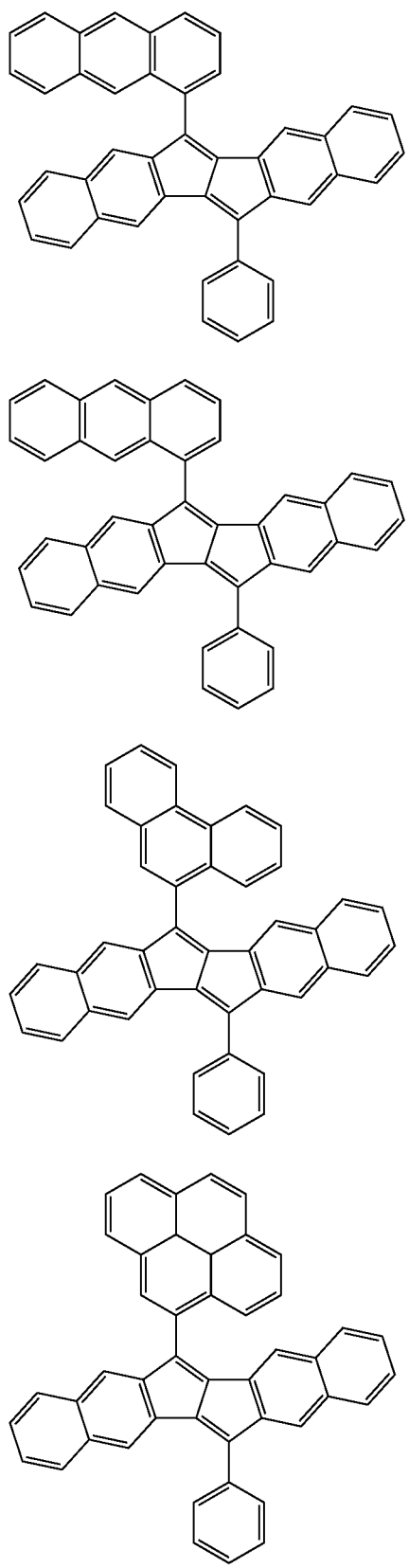
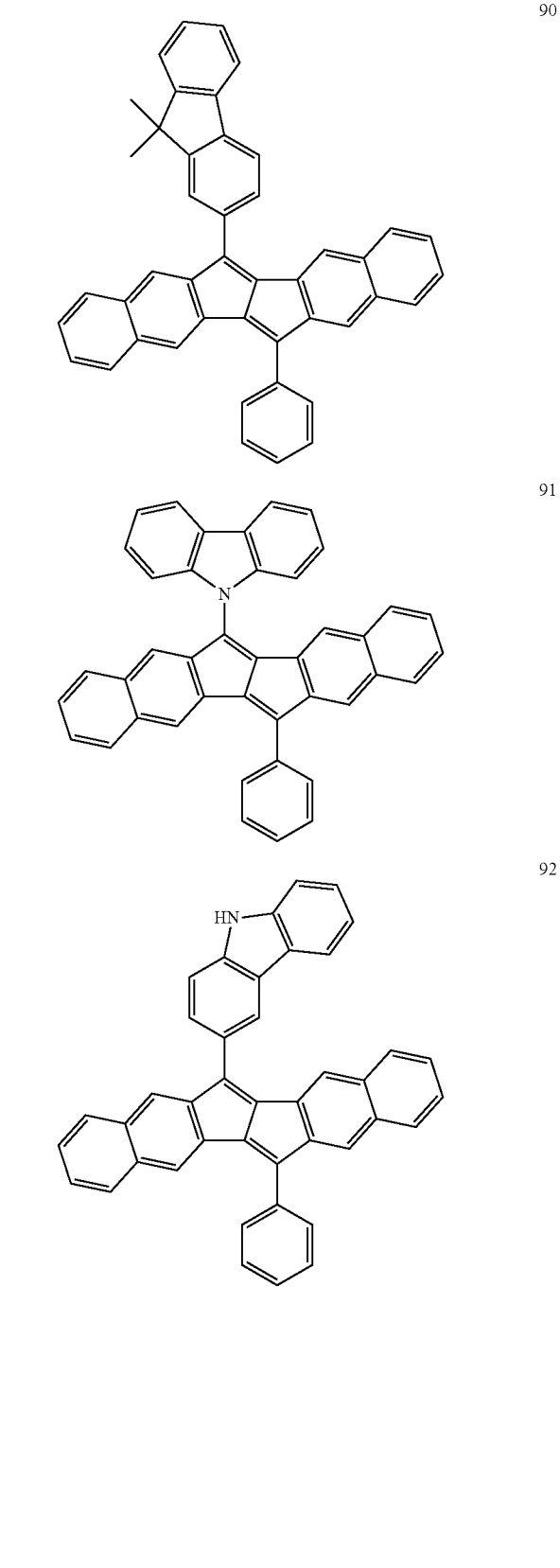

93
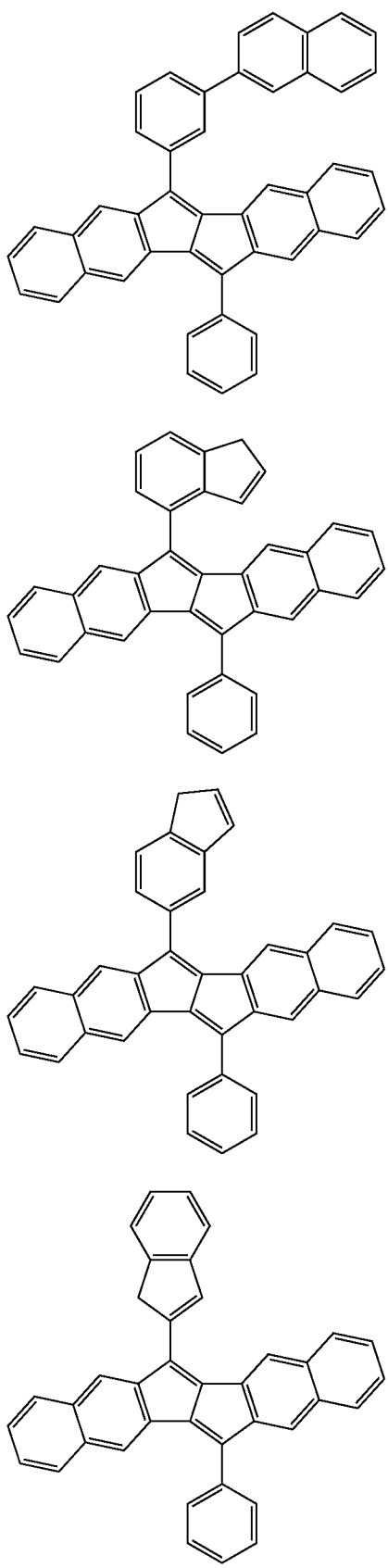
94
95
96
97
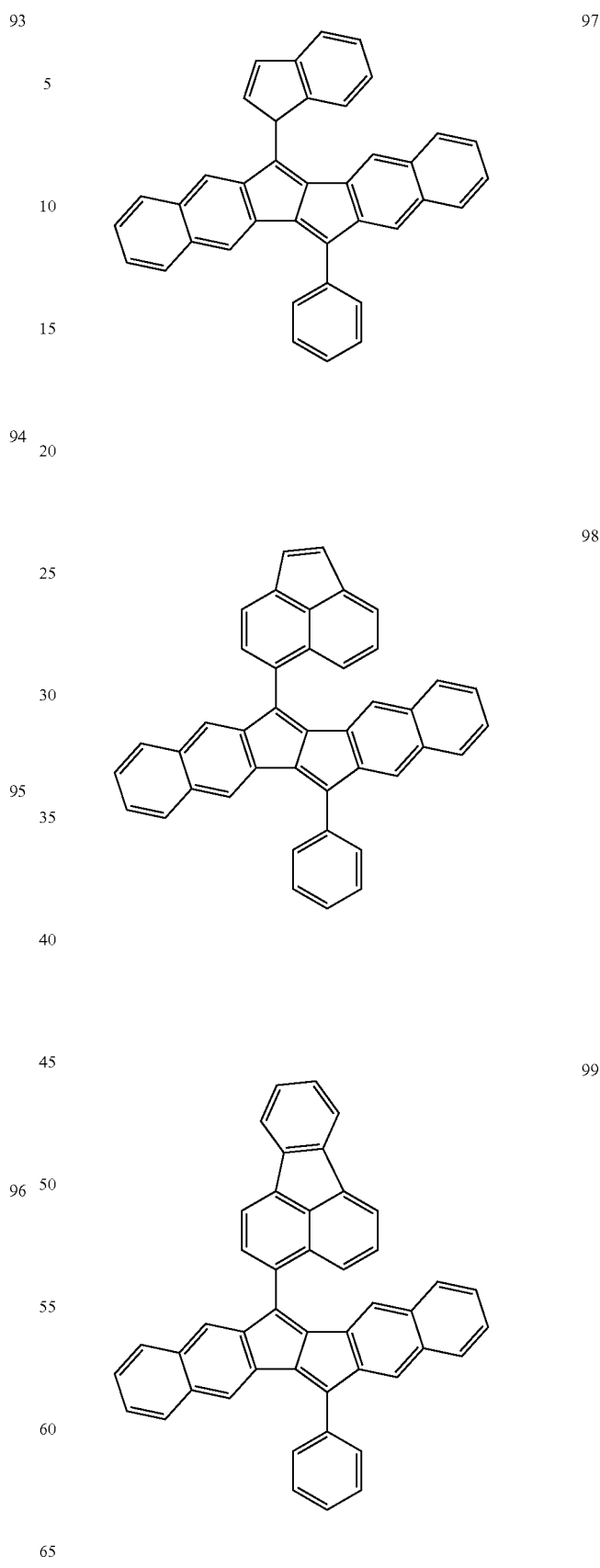
98
99

100
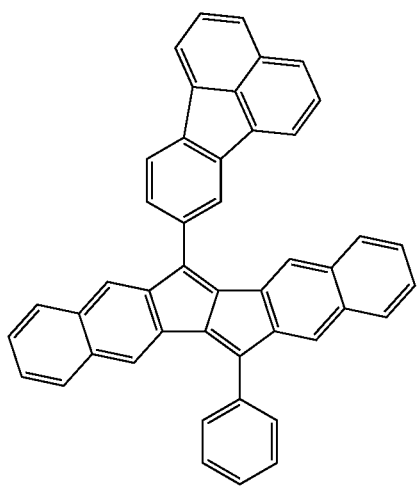
101
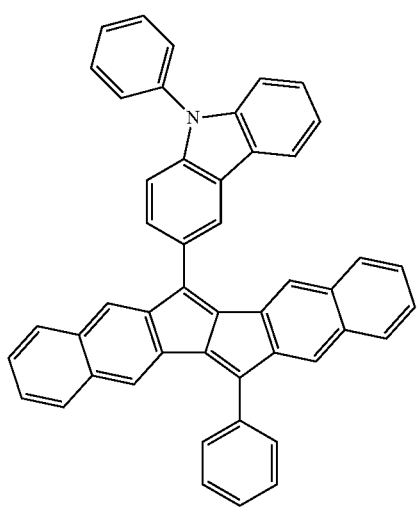
102
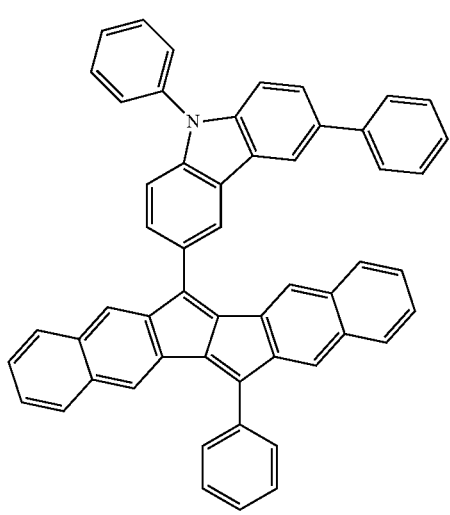
103
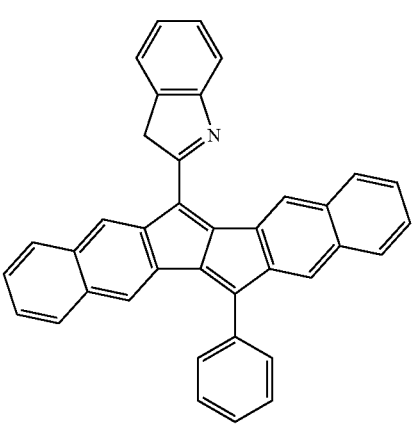
104
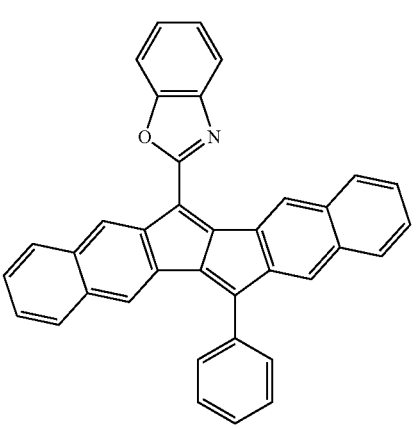
105
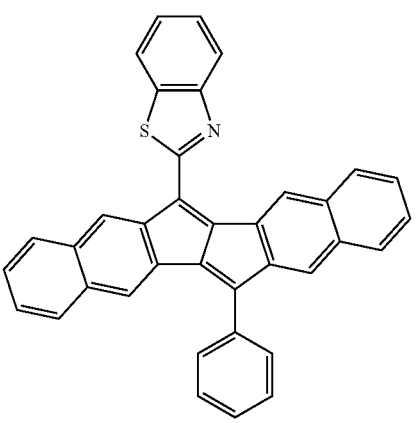

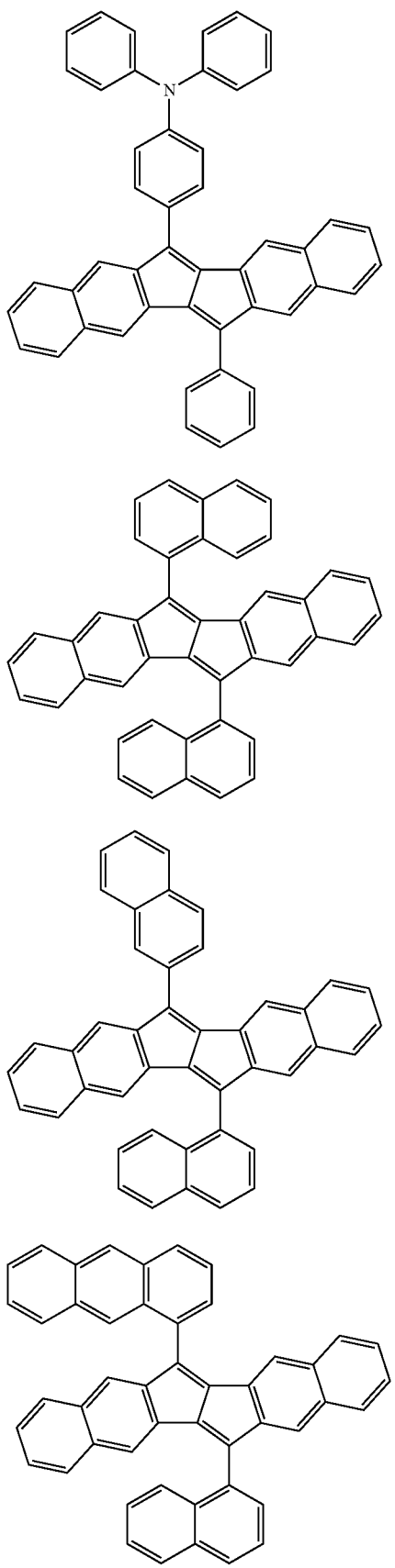
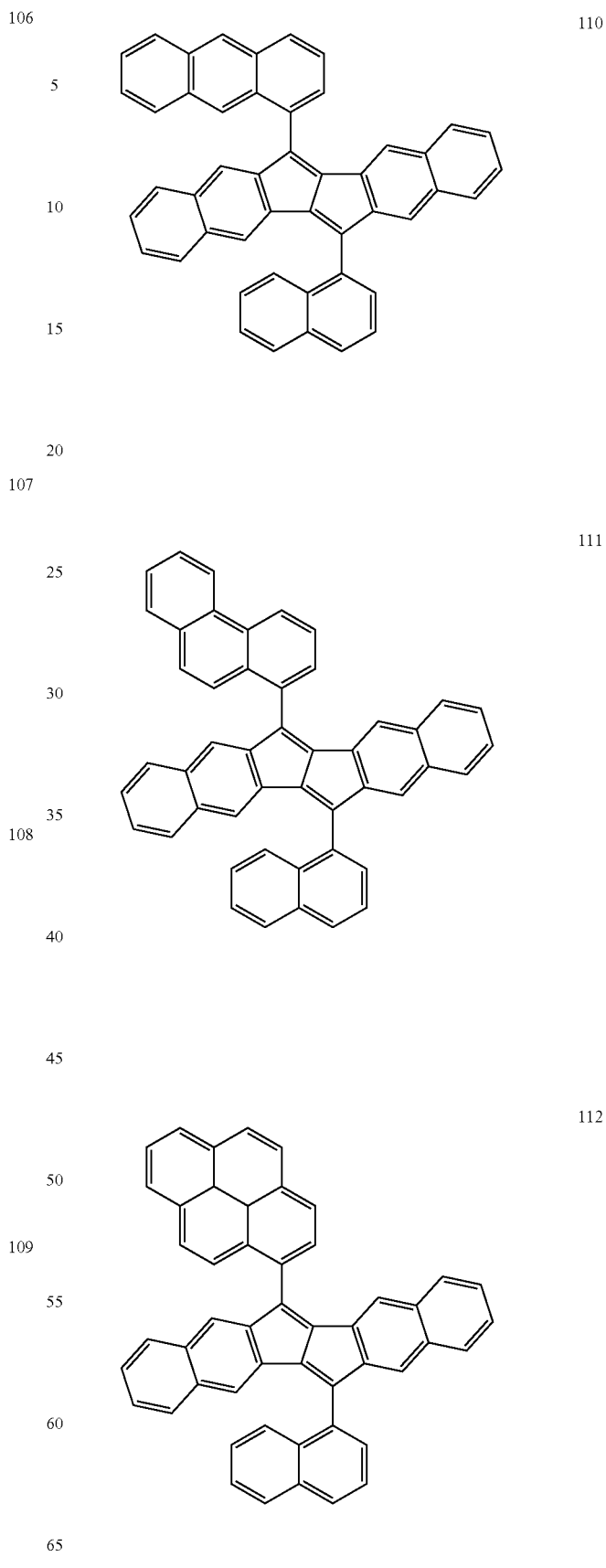

113
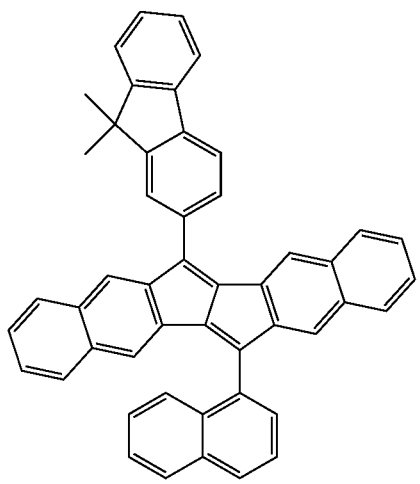
114
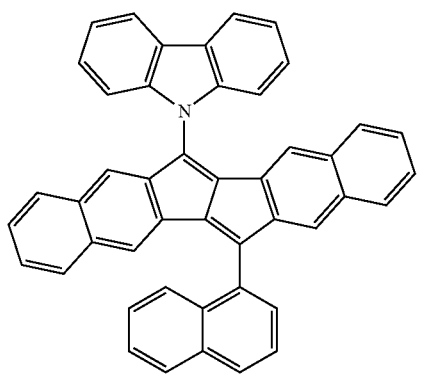
115
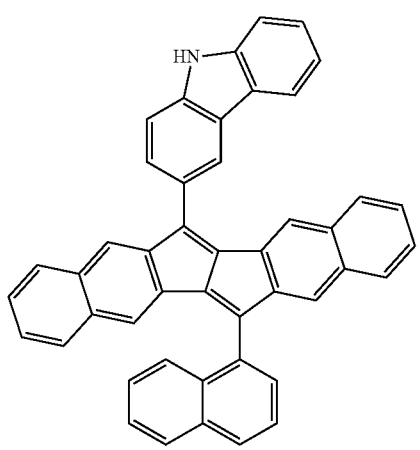
116
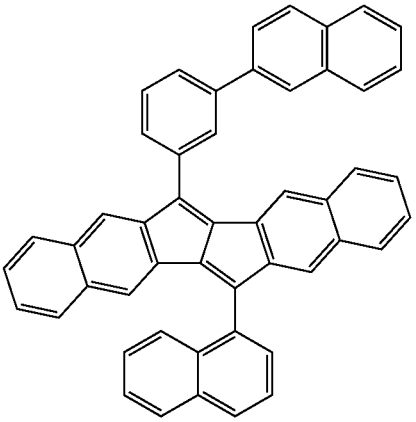
117
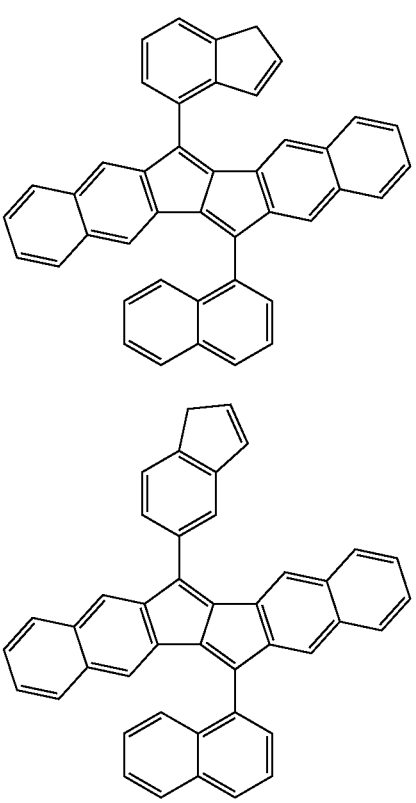
118
119
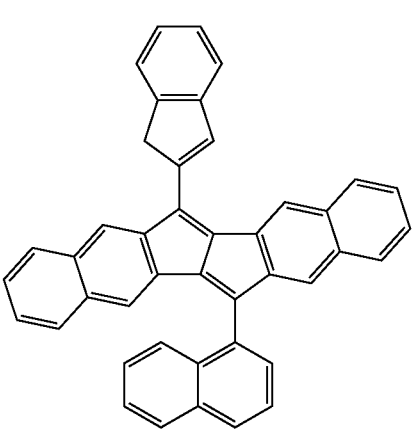

120
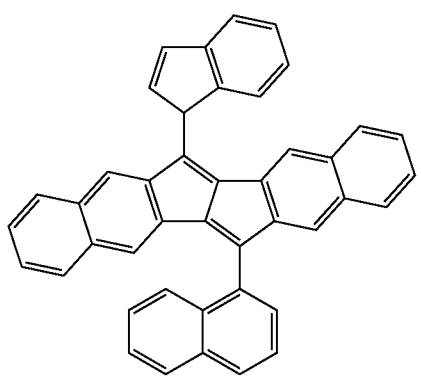
121
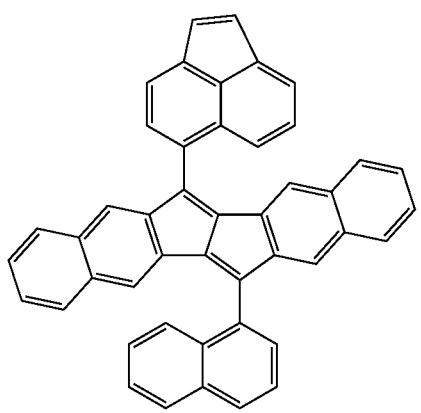
122
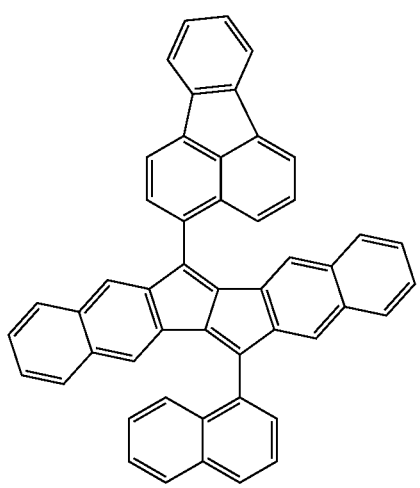
123
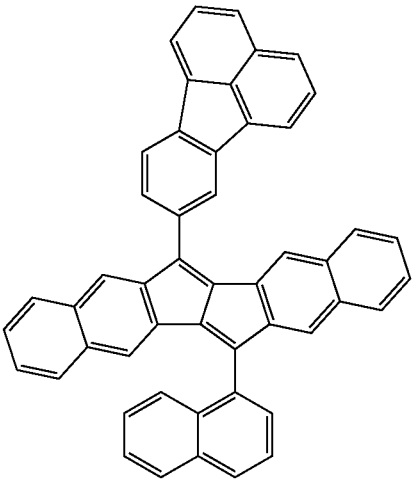
124
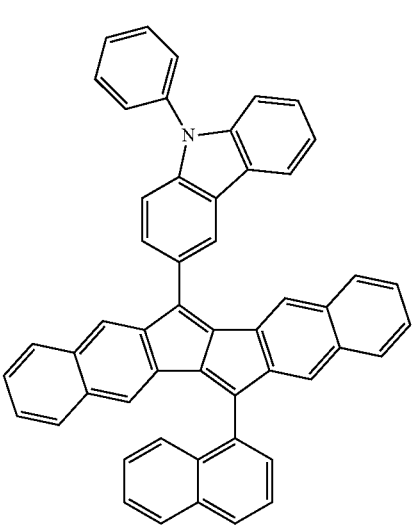
125
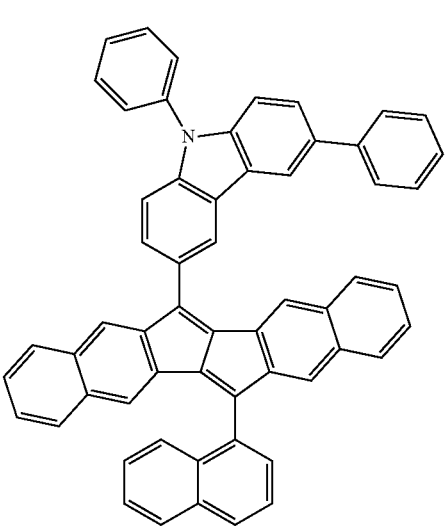

126
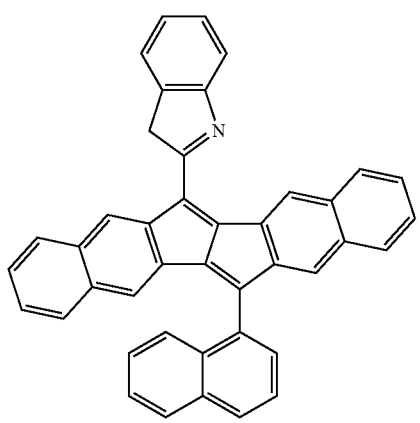
127
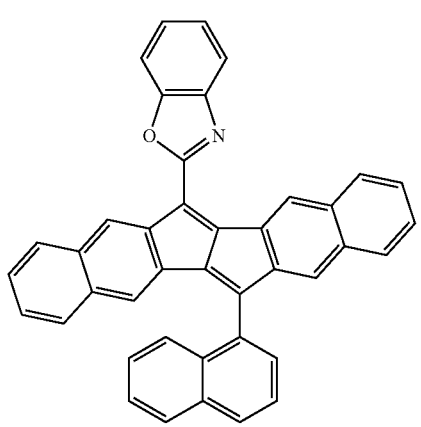
128
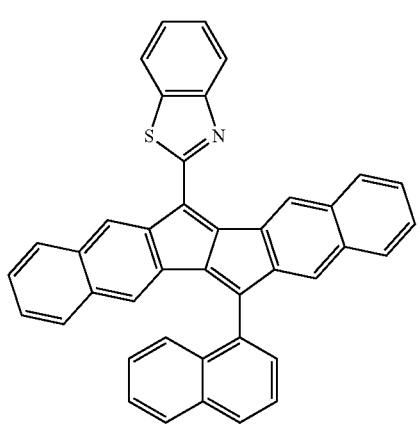
129
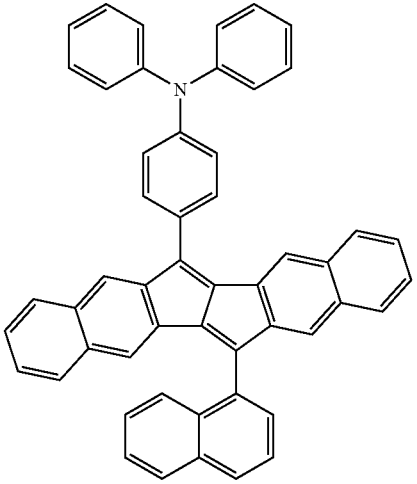
130
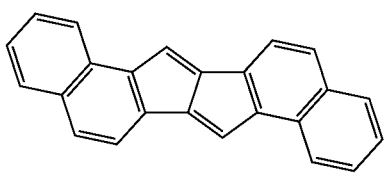
131
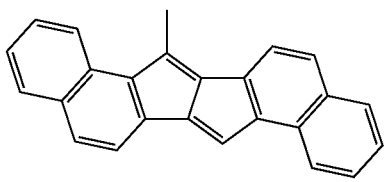
132
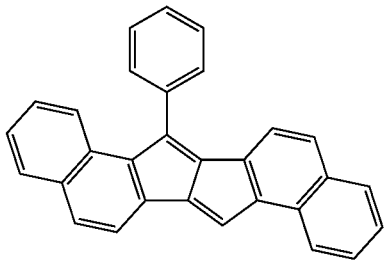
133
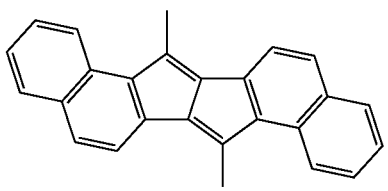
134
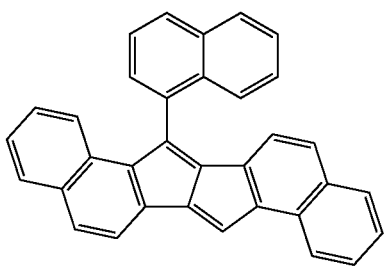

135
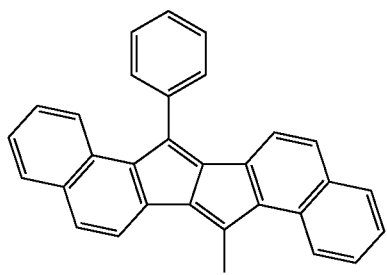
136
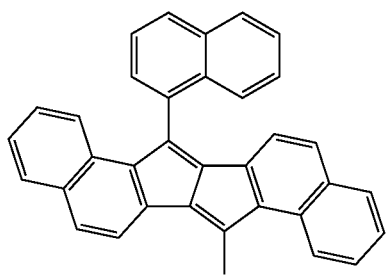
137
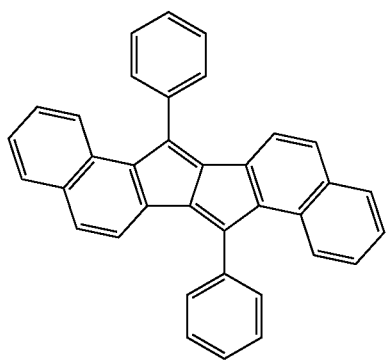
138
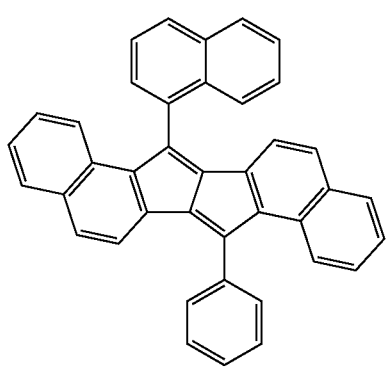
139
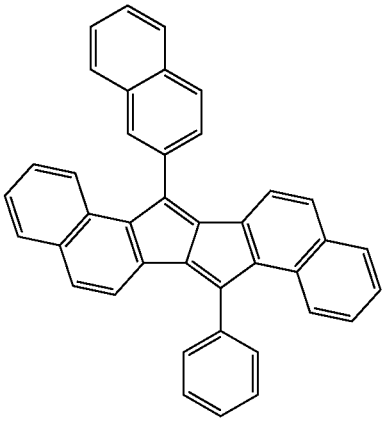
140
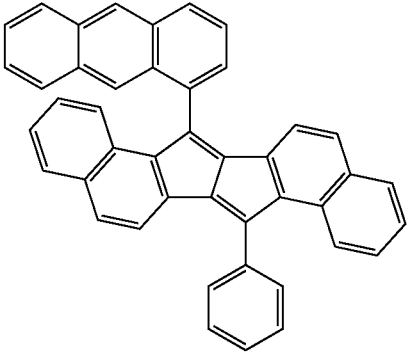
141
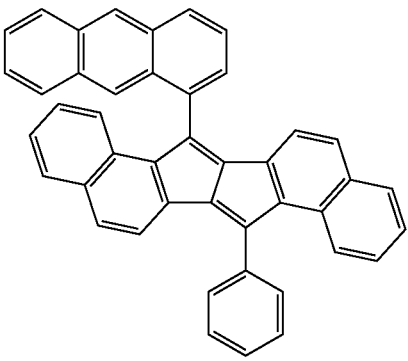
142
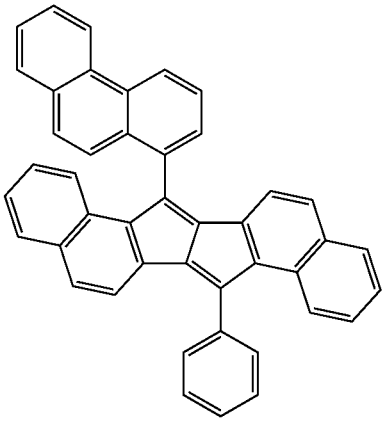

143
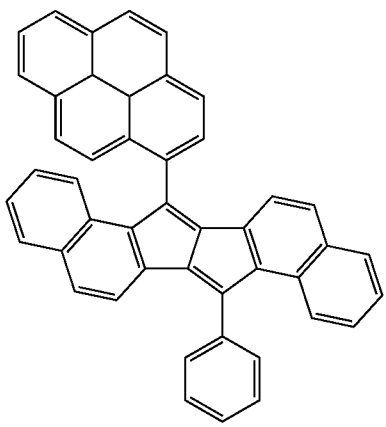
144
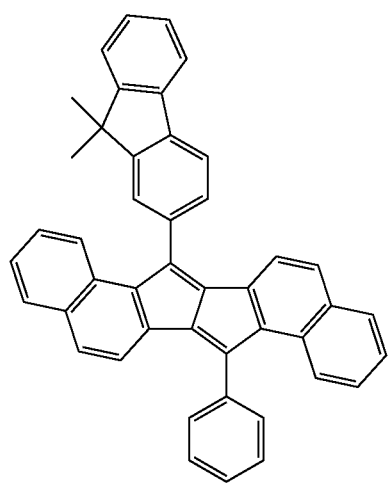
145
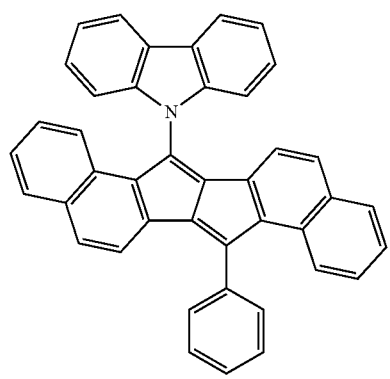
146
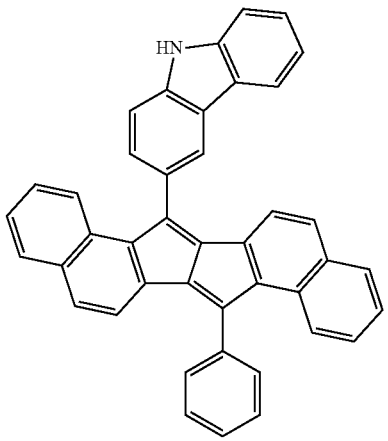
147
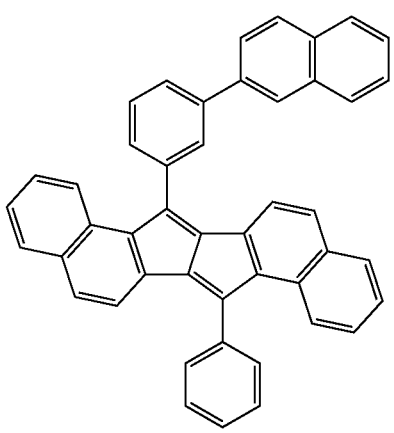
148
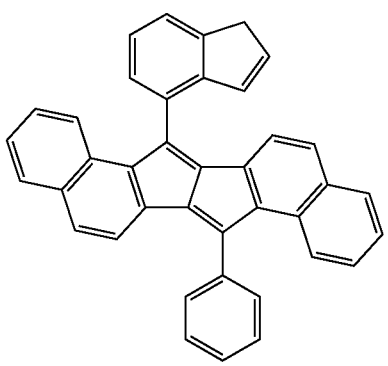
149
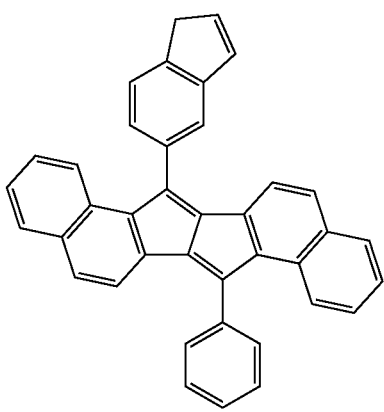

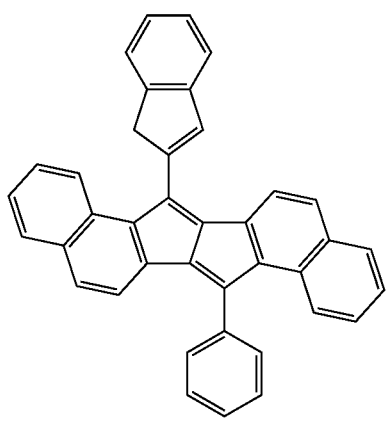
150
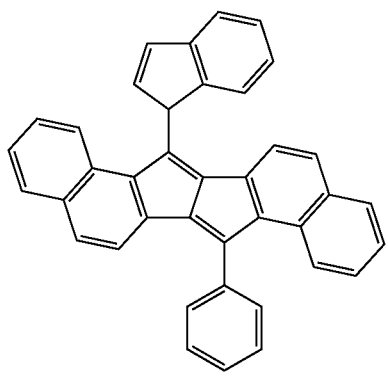
151
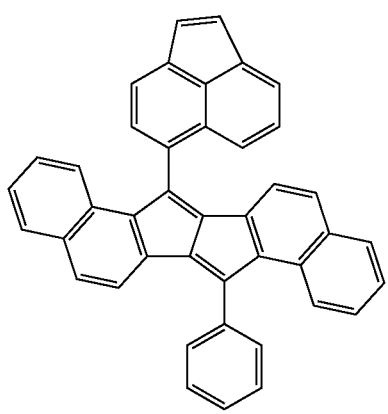
152
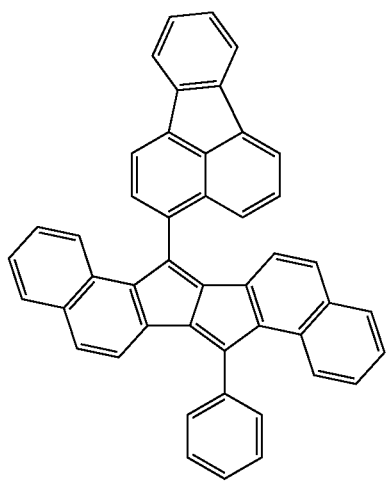
153
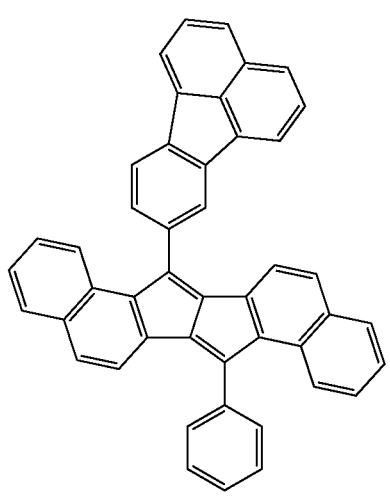
154
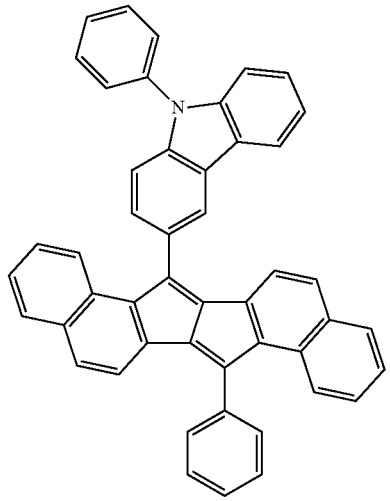
155

156
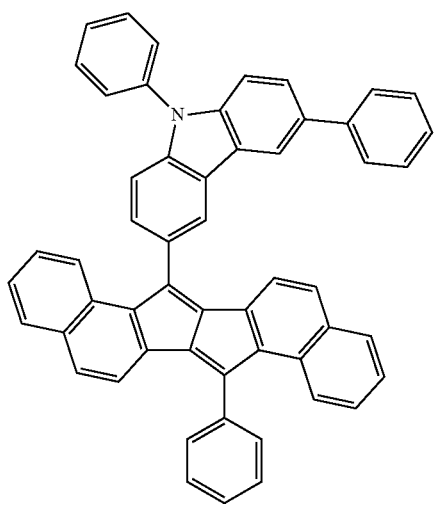
157
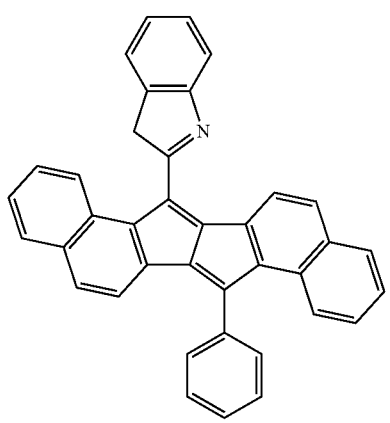
158
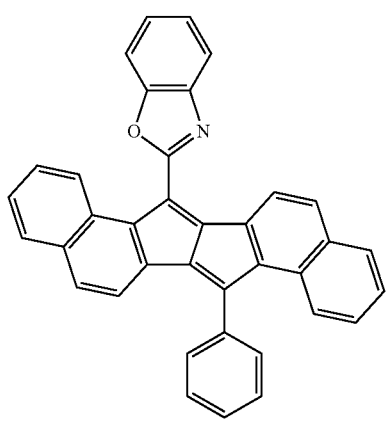
159
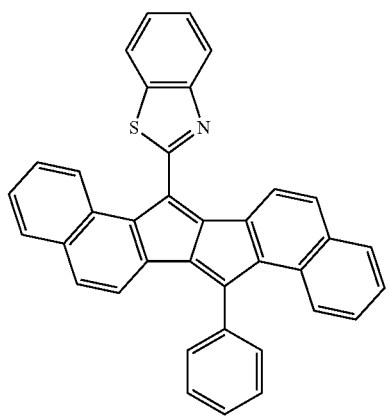
160
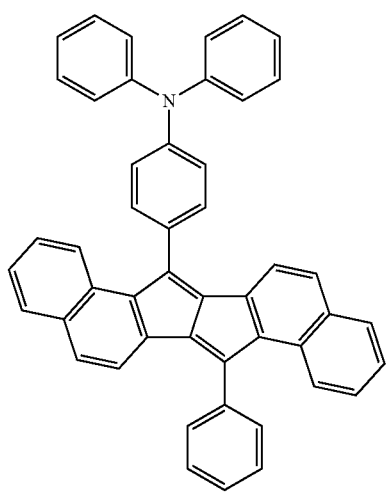
161
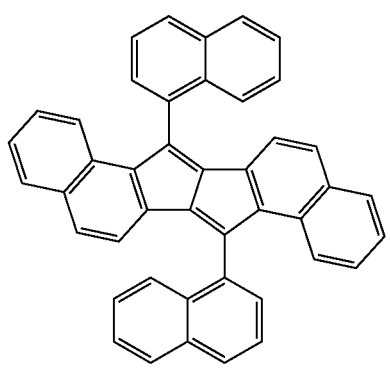

162
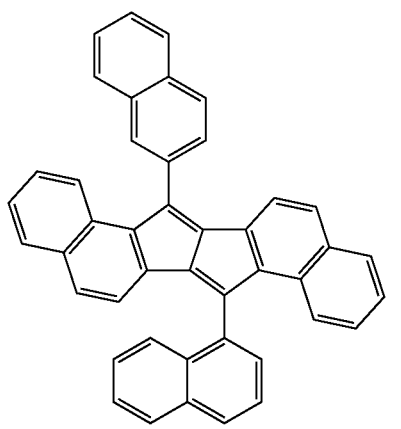
163
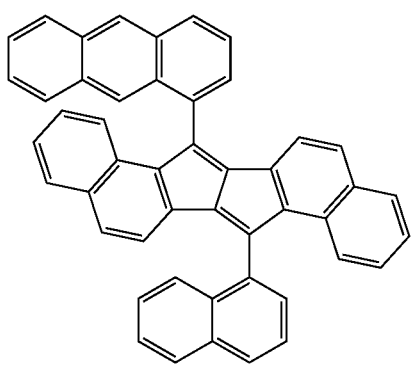
164
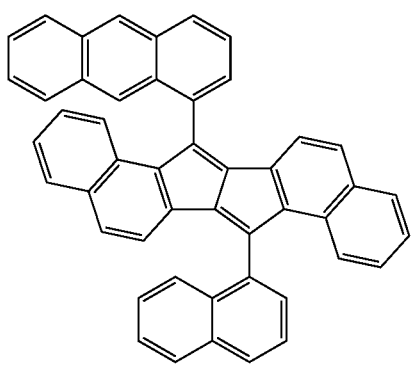
165
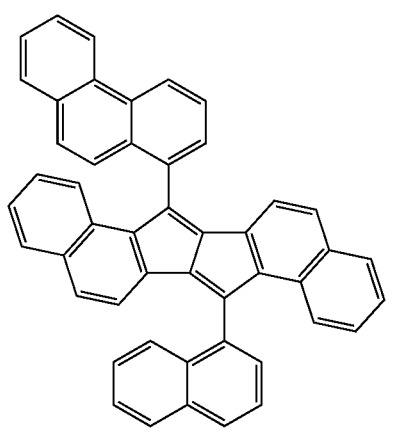
166
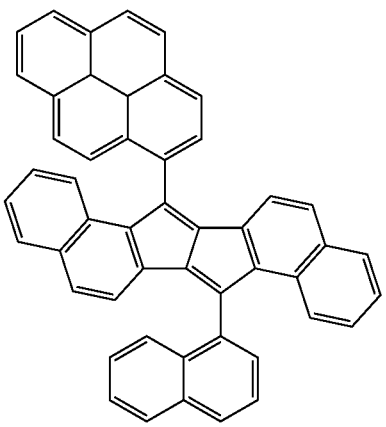
167
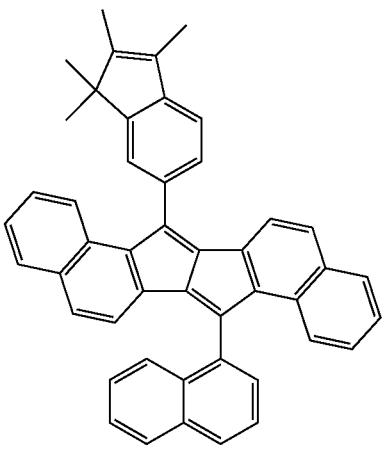
168
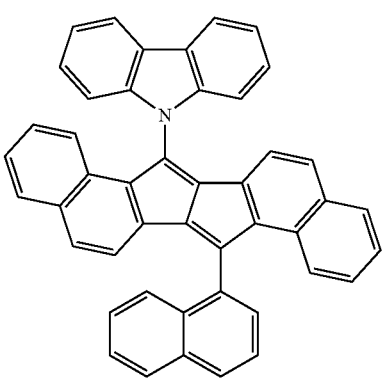

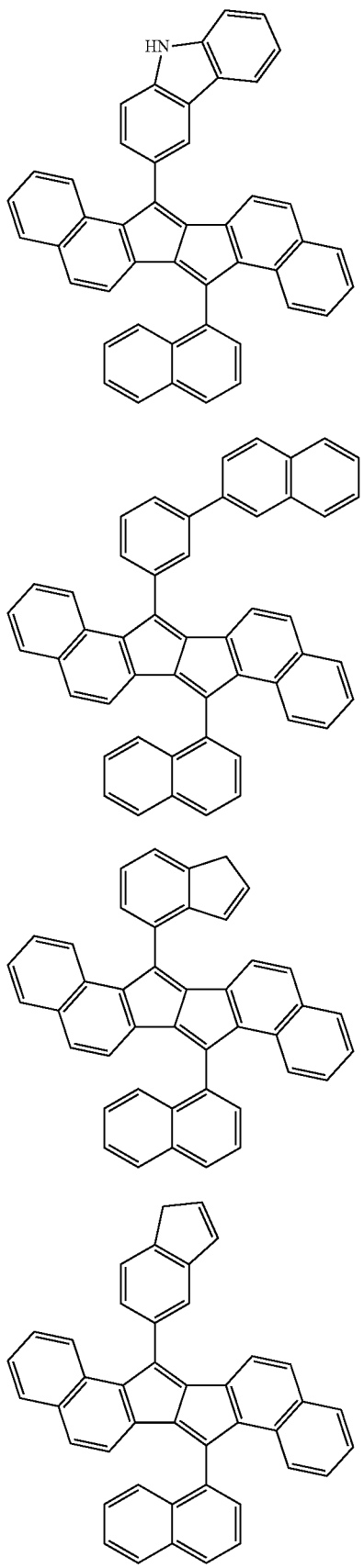
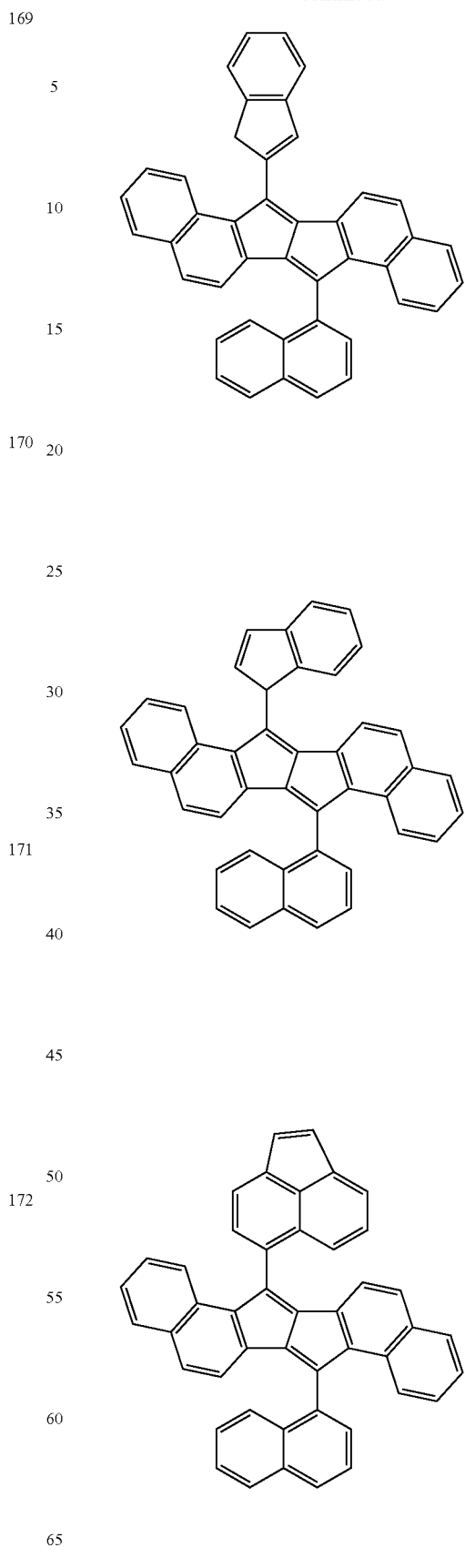

176
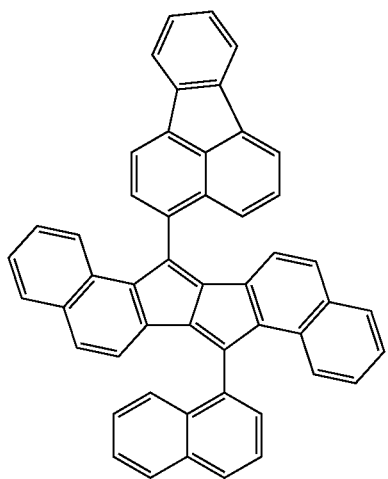
177
179
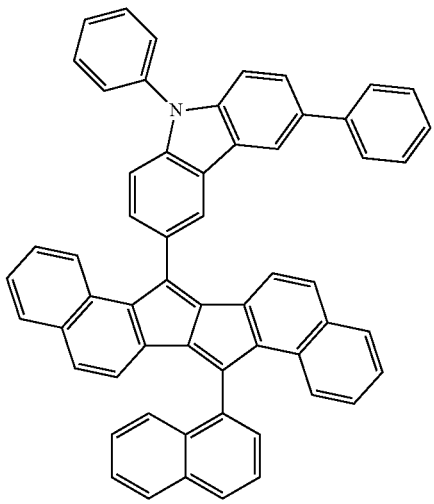
180
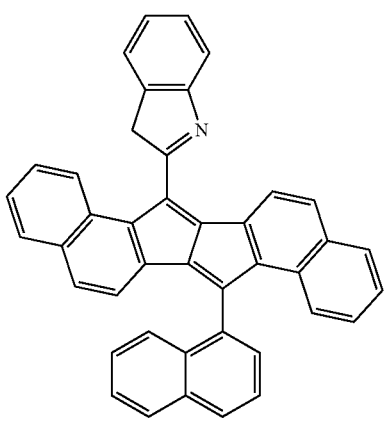
178
181
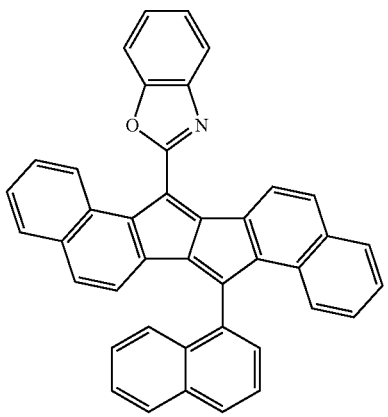

-continued

182

183

184

185

-continued

186

187

188

189

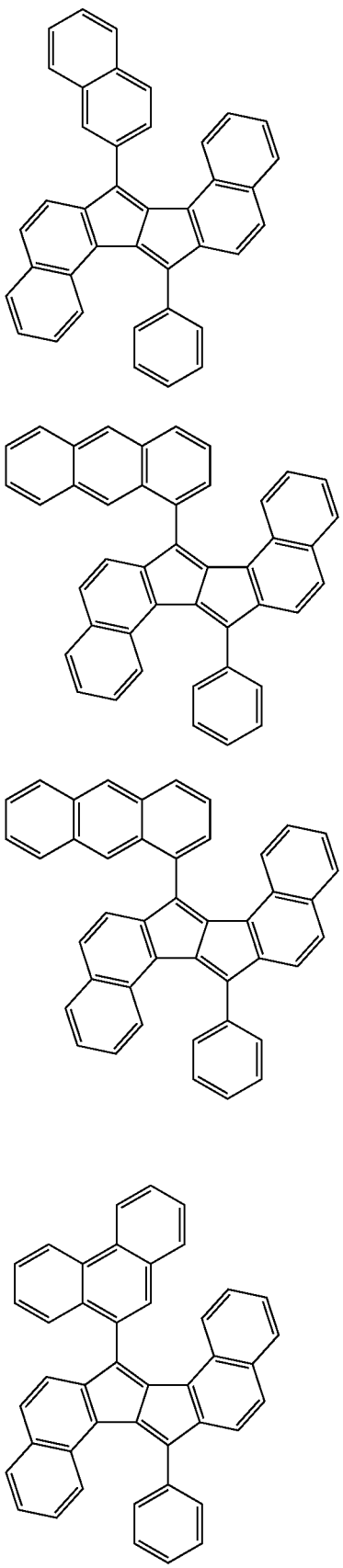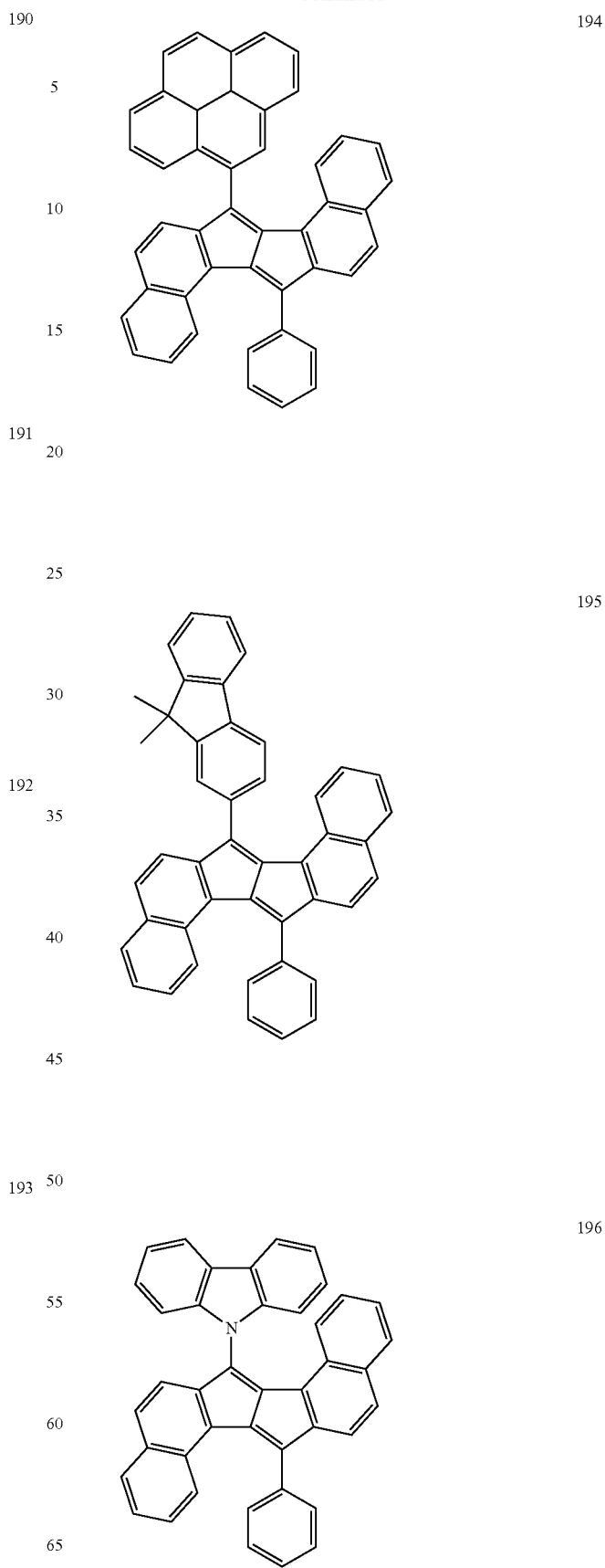

197
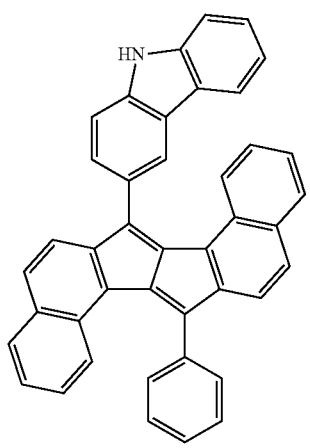
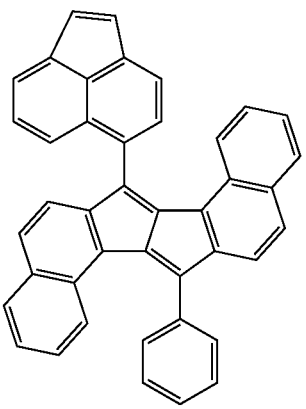
198
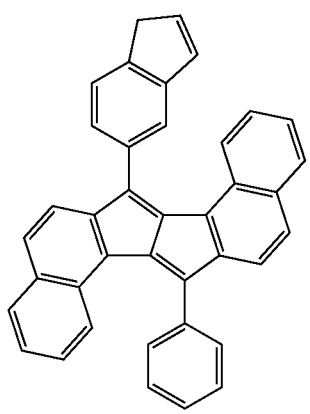
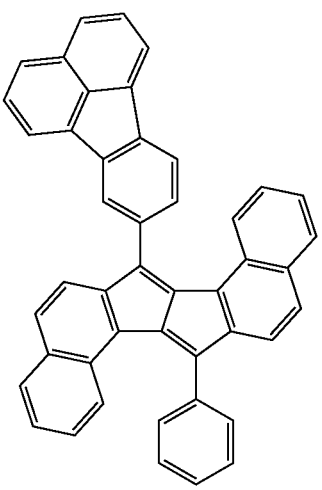
199
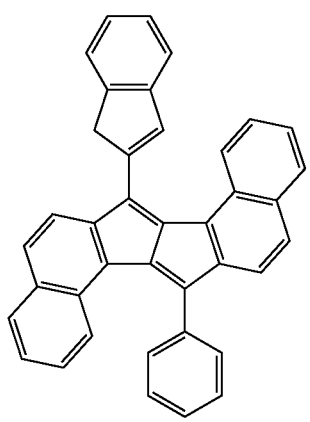
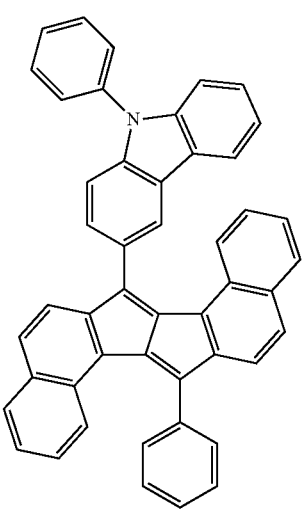
200
201
202

-continued
203
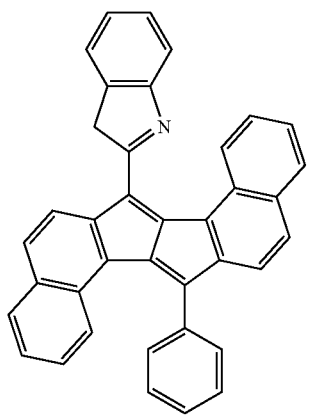
204
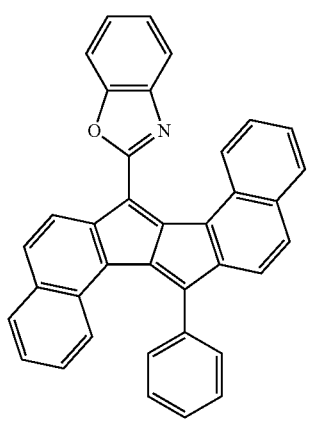
205
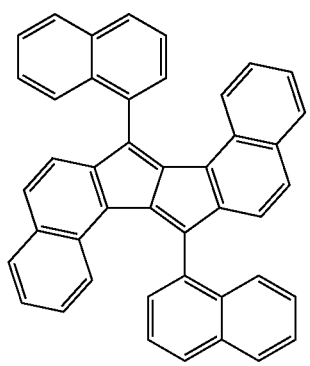
206
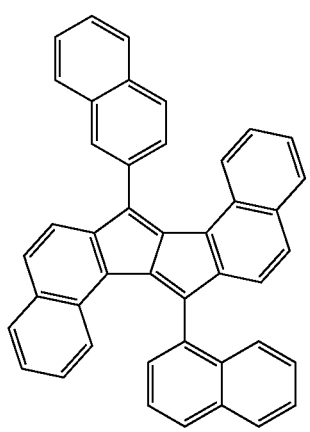
-continued
207
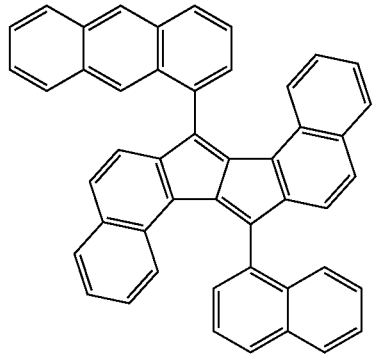
208
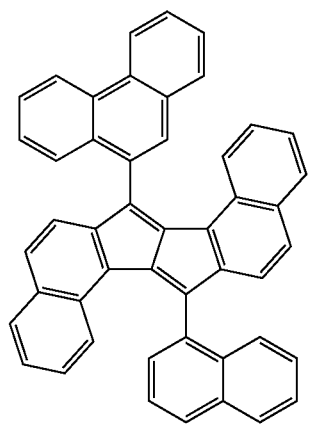
209
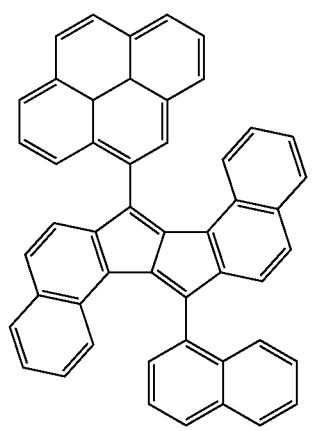

US 9,899,600 B2
-continued
210
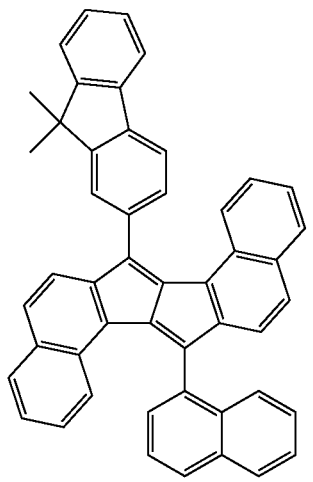
211
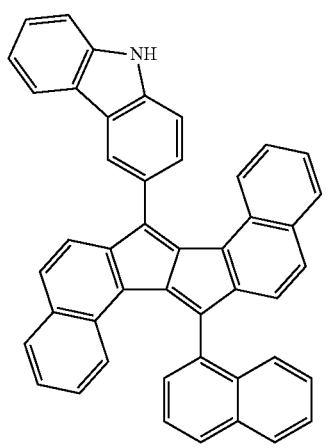
212
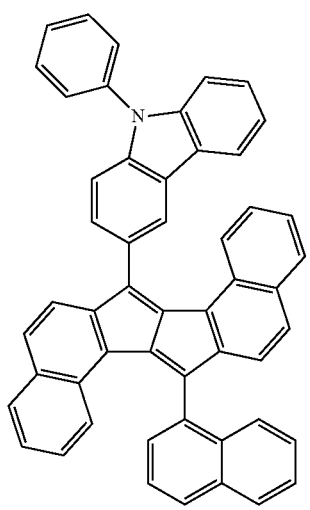
-continued
213
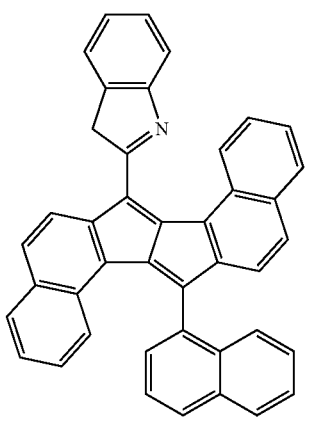
214
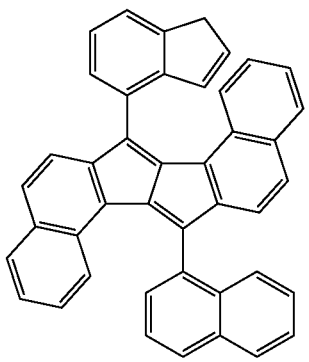
215
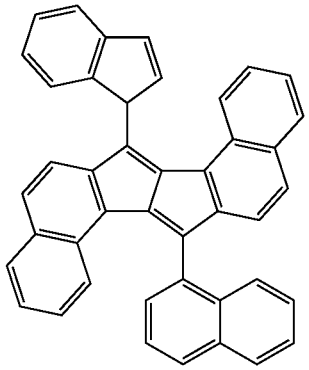
216
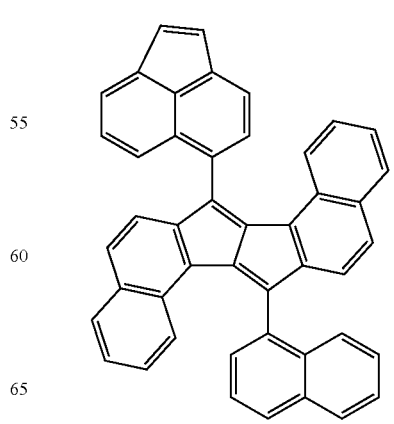

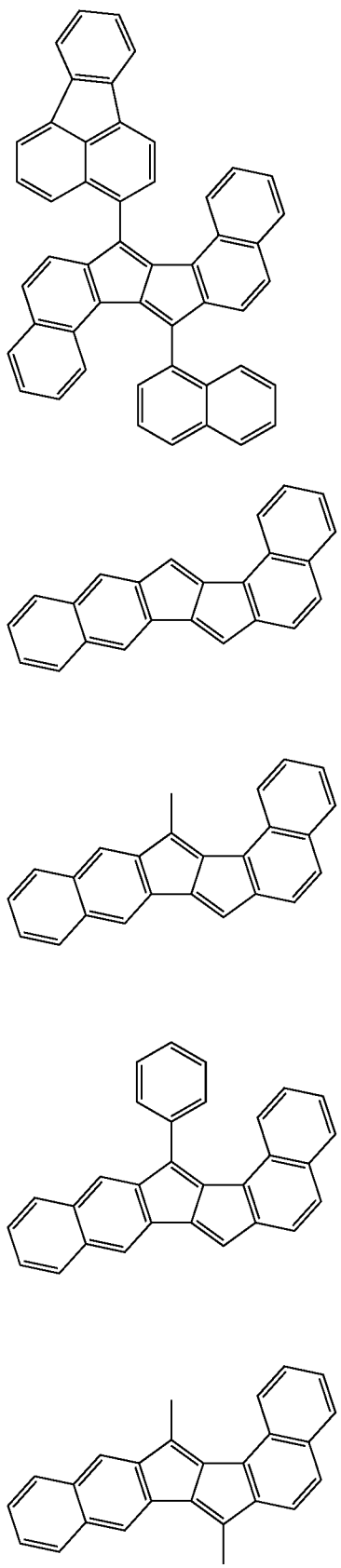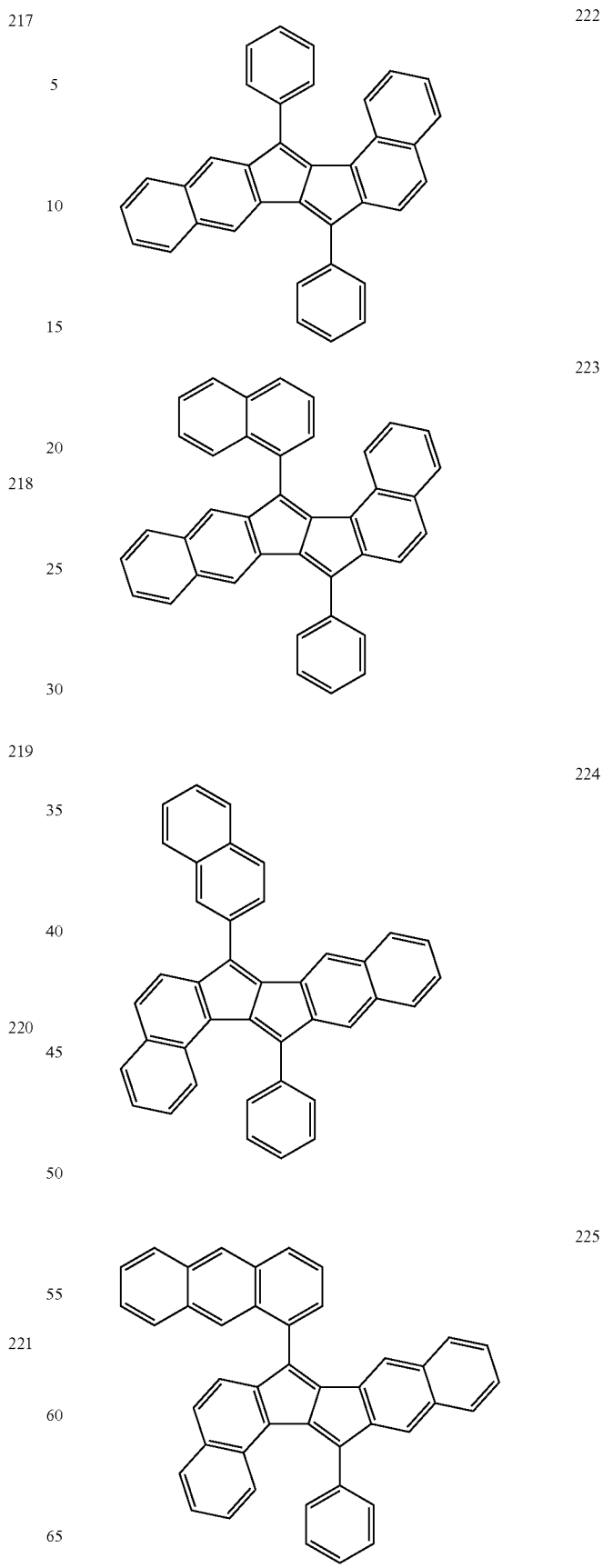

226
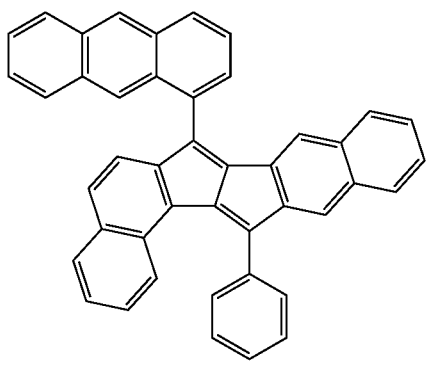
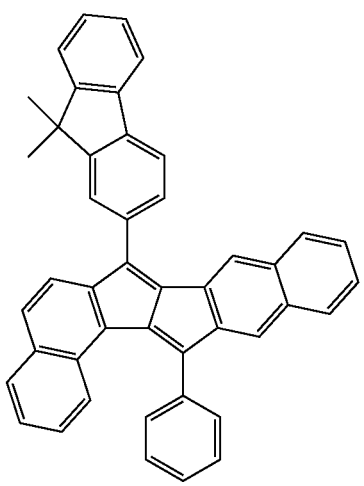
227
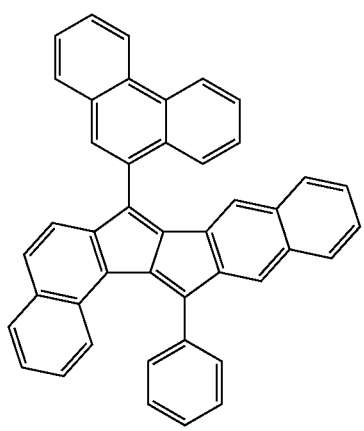
229
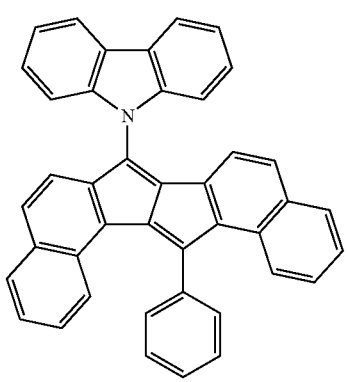
230
228
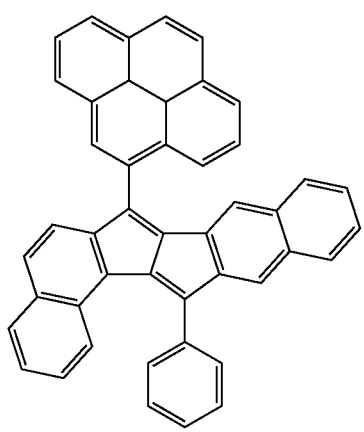
231
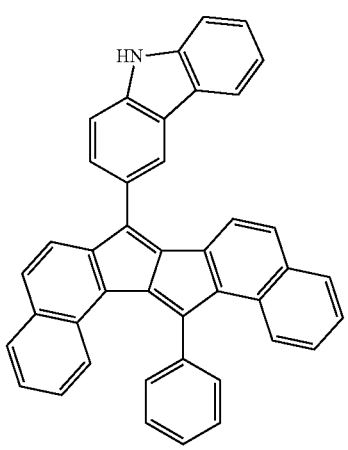

232
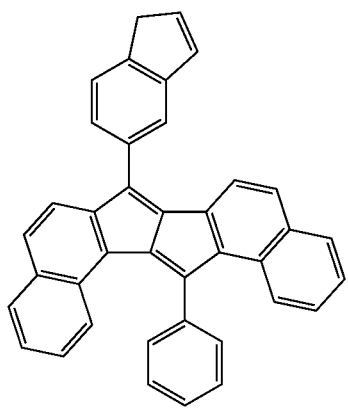
233
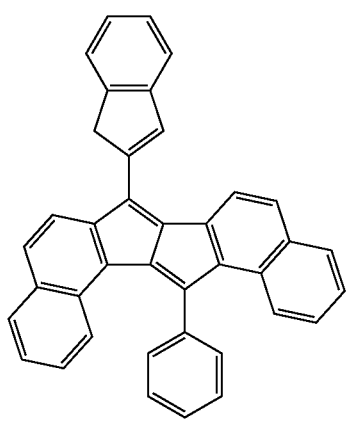
234
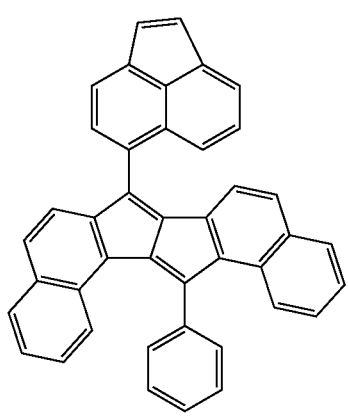
235
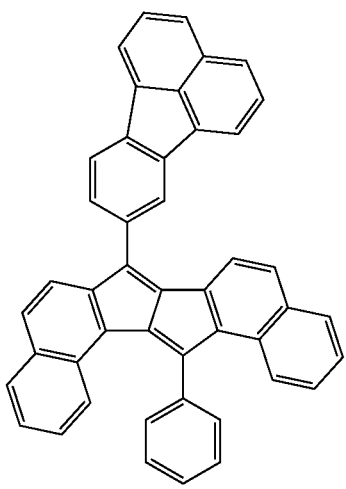
236
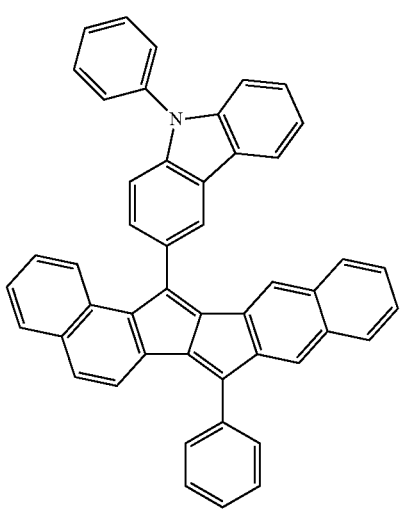
237
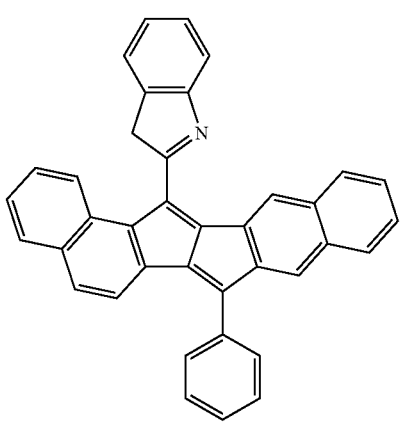

-continued

238

239

240

241

-continued

242

243

244

245 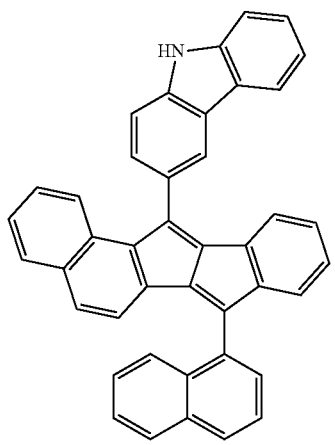
246 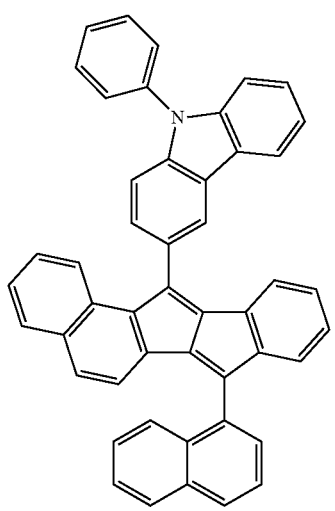
247 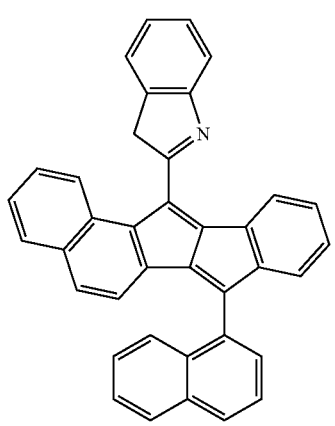
248 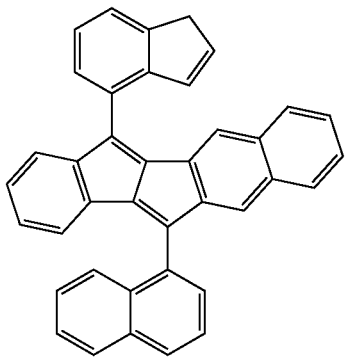
249 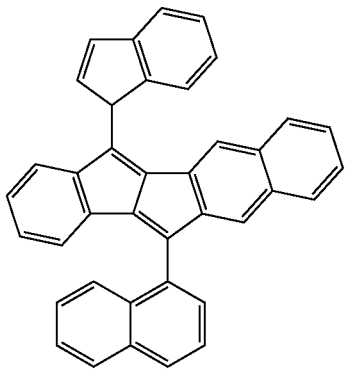
250 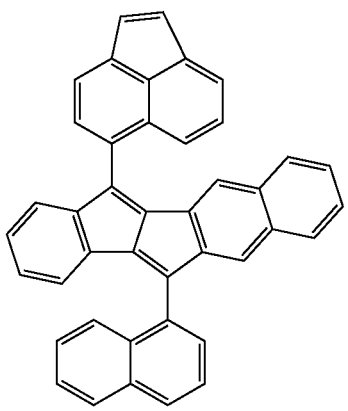
251 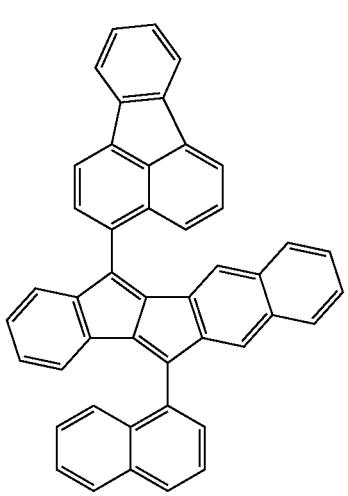

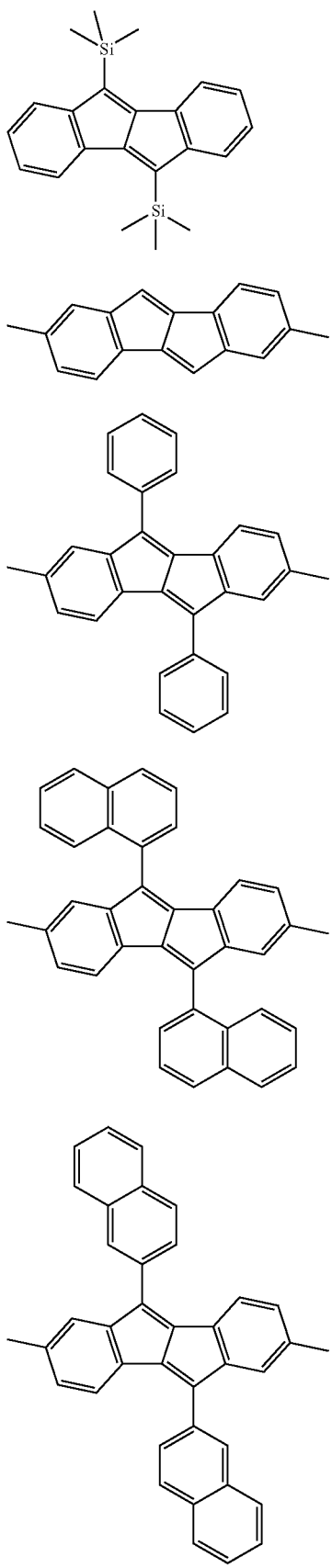
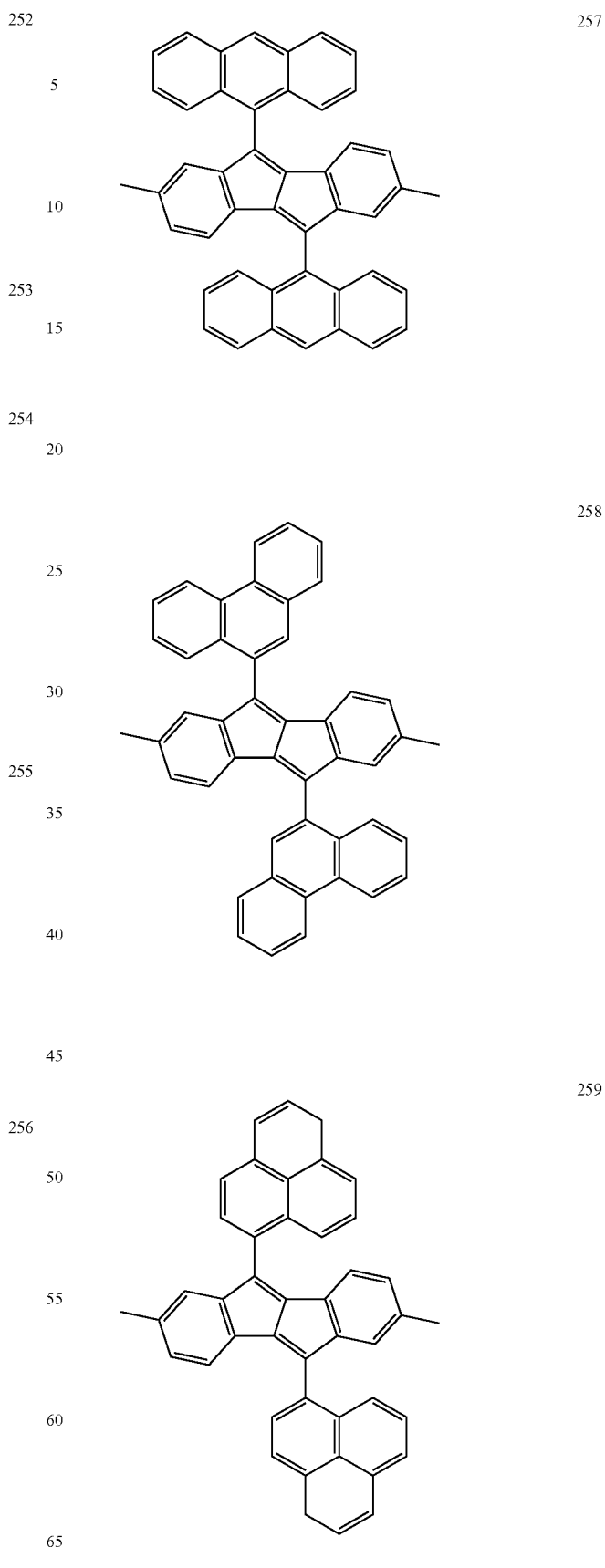

85
-continued
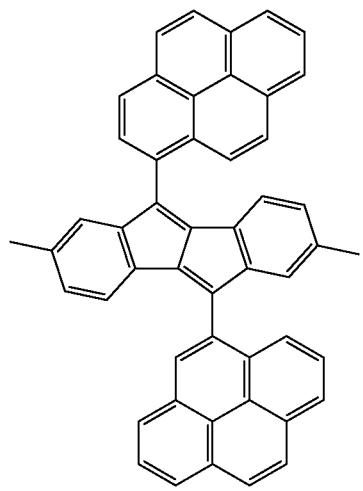
260
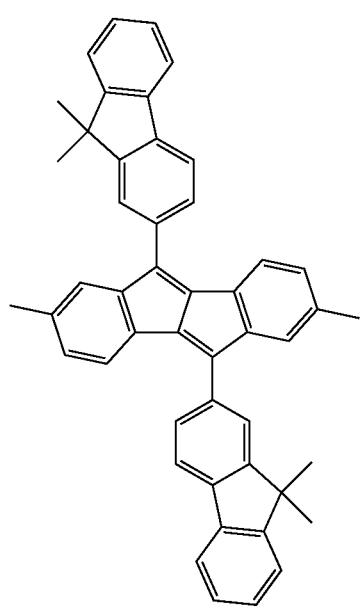
261
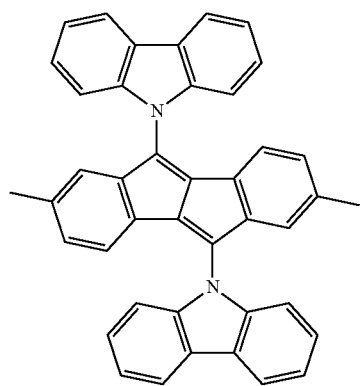
262
86
-continued
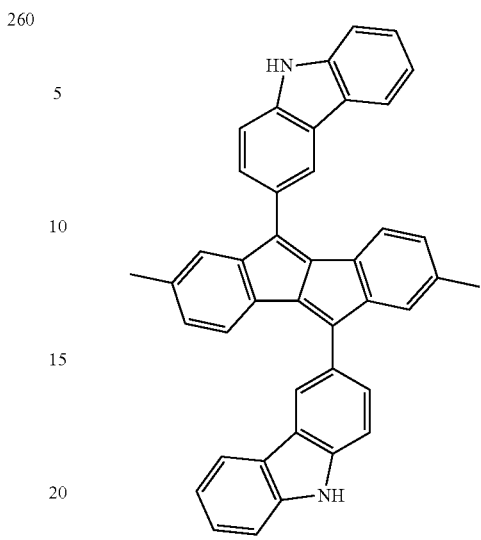
263
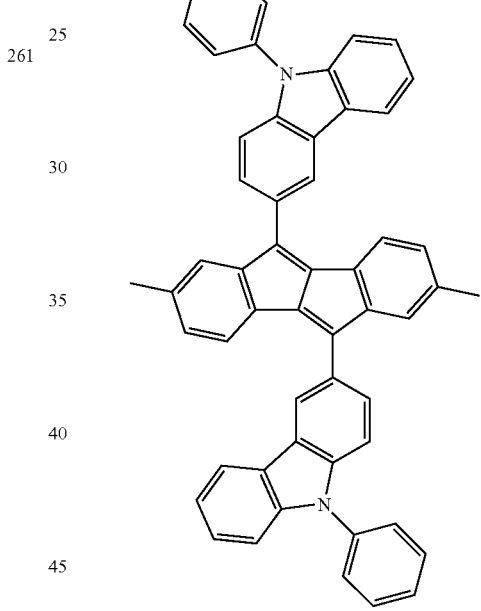
264
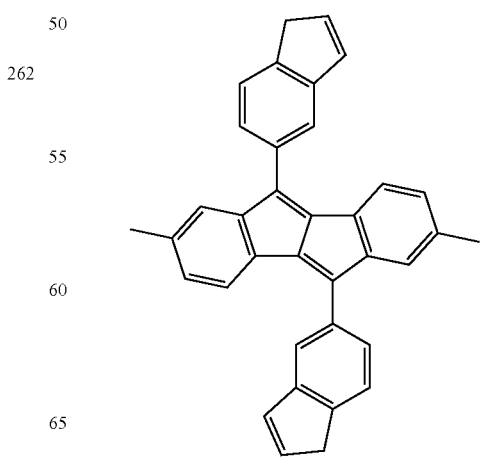
265

266
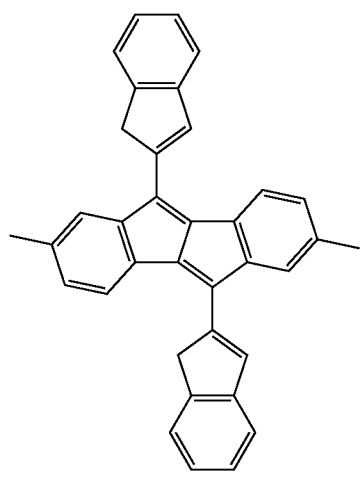
267
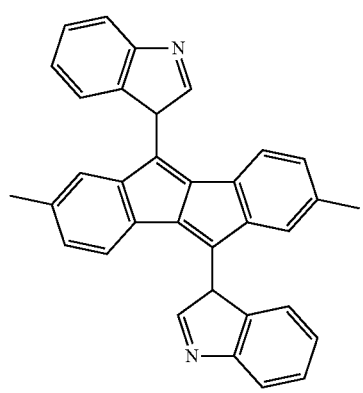
268
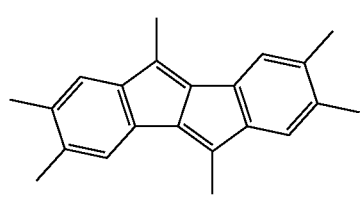
269
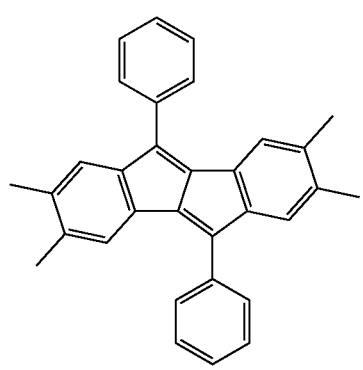
270
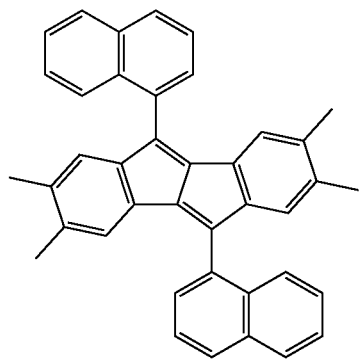
271
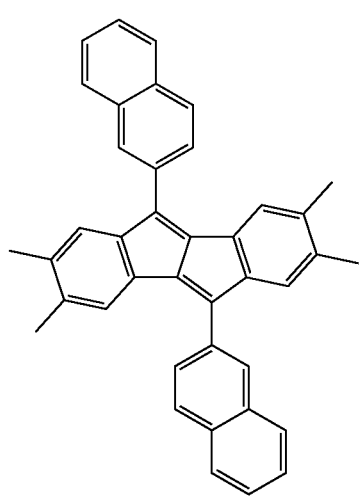
272
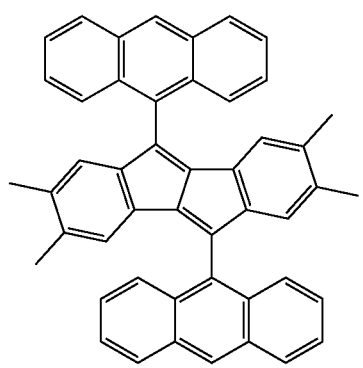

273
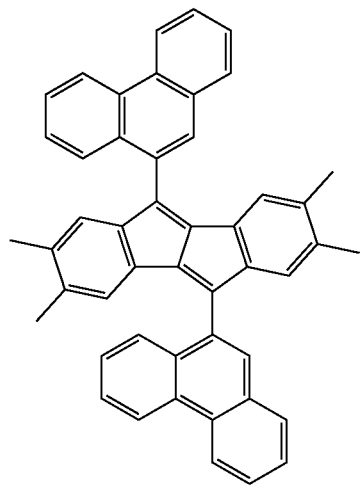
274
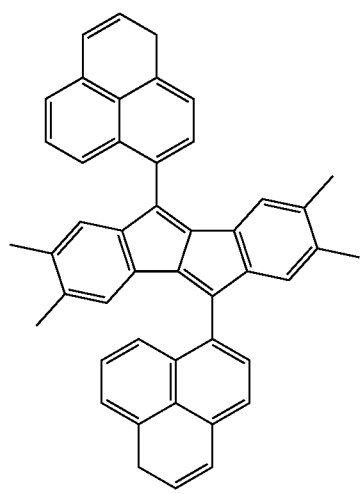
275
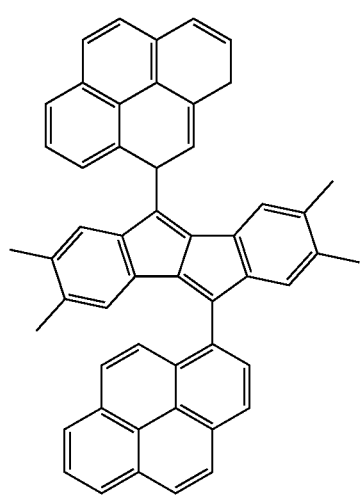
276
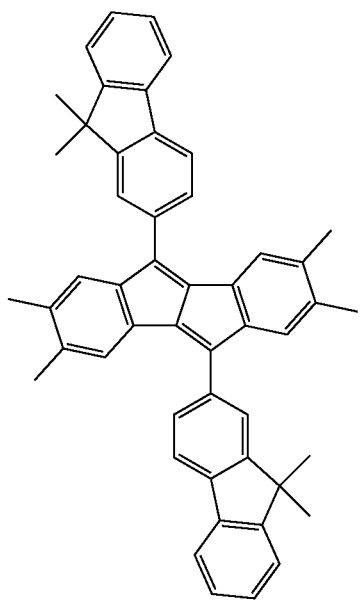
277
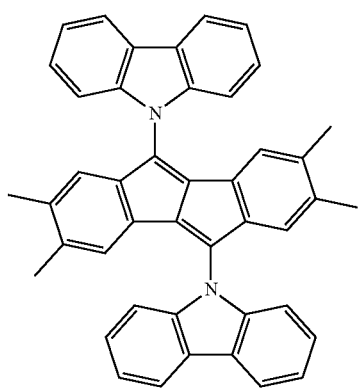
278
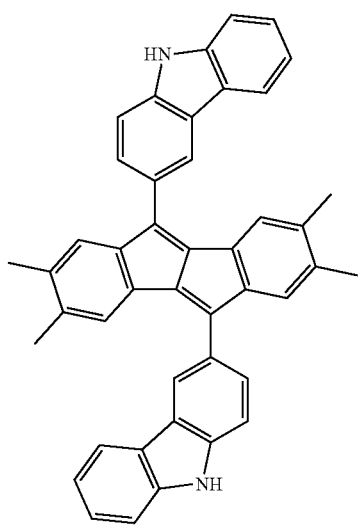

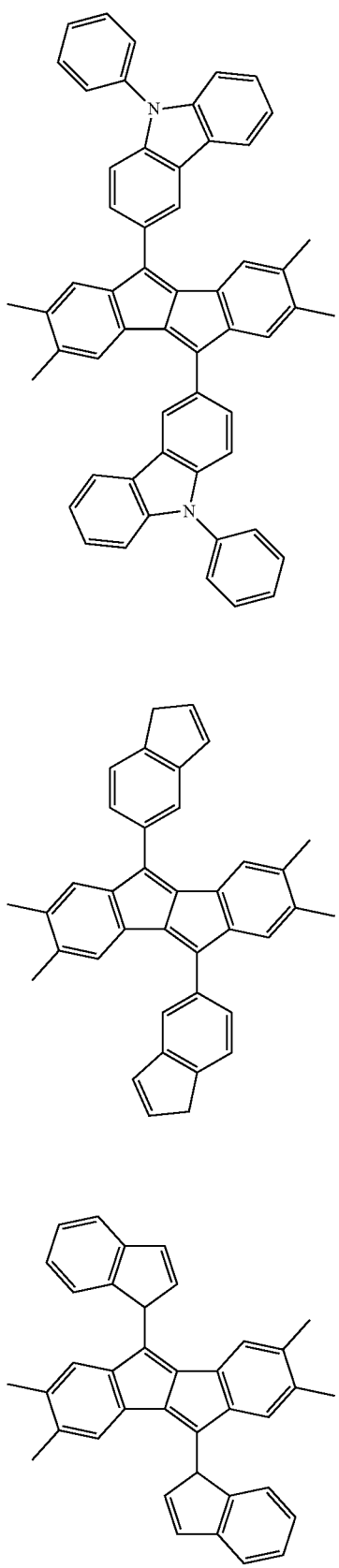
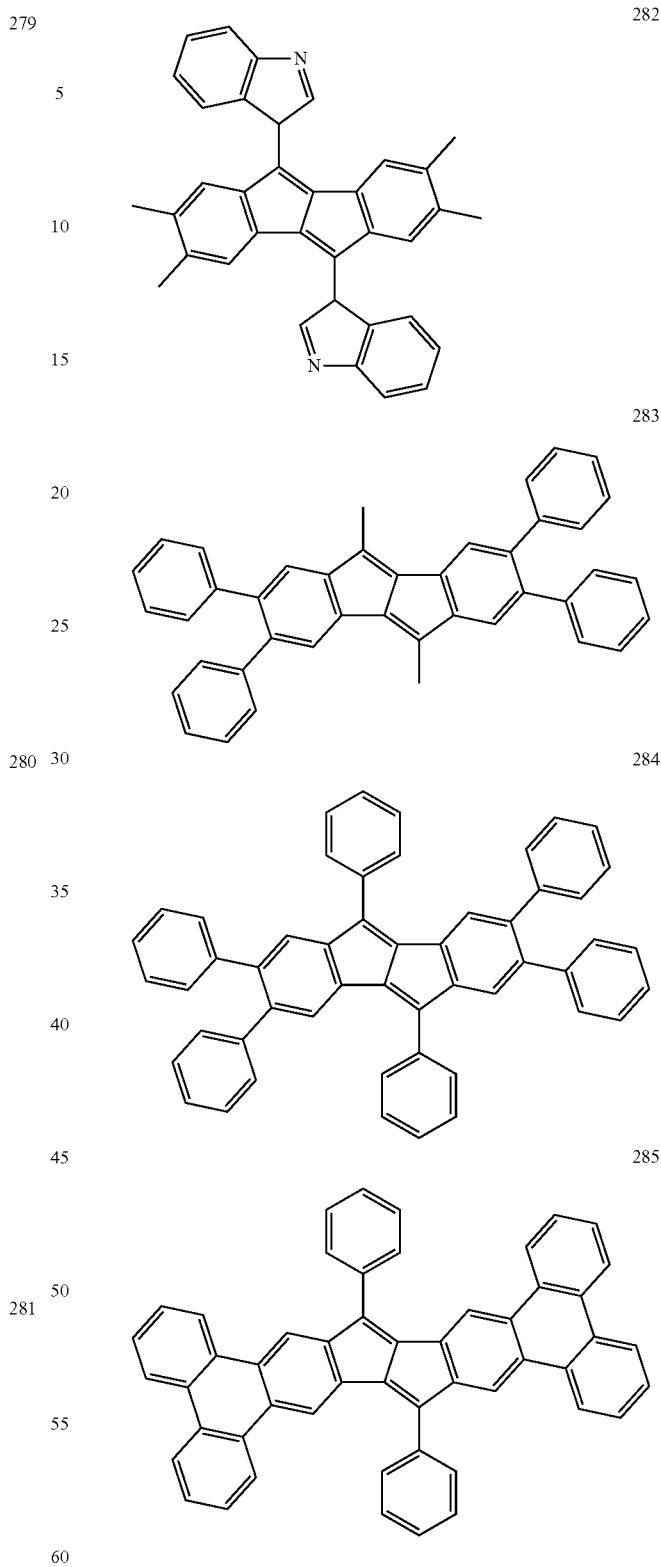
The compounds described in the present specification may be prepared with reference to preparation examples described later.
The present invention also provides an organic light emitting device that includes a first electrode, a second electrode, and one or more organic material layers provided between the first electrode and the second electrode, wherein one or more layers of the organic material layers include the compound of Chemical Formula 1.

The laminating order of the electrodes and the organic material layers of the organic light emitting device according to embodiments of the present invention is illustrated in FIGS. 1 to 3. However, these diagrams are not intended to limit the scope of the present invention, and the structures of organic light emitting devices known in the related art may also be applied to the present invention.

According to FIG. 1, an organic light emitting device in which an anode (200), an organic material layer (300) and a cathode (400) are laminated on a substrate (100) in consecutive order is shown by the diagram. However, the structure of the organic light emitting device is not limited to this structure only, and as shown in FIG. 2, an organic light emitting device in which a cathode, an organic material layer and an anode are laminated on a substrate in consecutive order may be included.

FIG. 3 illustrates the case in which the organic material layer is a multilayer. An organic light emitting device according to FIG. 3 includes a hole injection layer (301), a hole transfer layer (302), a light emitting layer (303), an electron transfer layer (304) and an electron injection layer (305). However, the scope of the present invention is not limited to this laminated structure, and when necessary, other layers except a light emitting layer may not be included, and other necessary layers having other functions may be added.

An organic light emitting device according to the present invention may be prepared using methods known in the related art except that the compound of Chemical Formula 1 is included in one or more layers of the organic material layers.

The compound of Chemical Formula 1 may form one or more layers of the organic material layers alone in the organic light emitting device. However, when necessary, the compound of Chemical Formula 1 may form the organic material layers by being mixed with other materials.

The compound of Chemical Formula 1 may be used as a hole injection material, a hole transfer material, a light emitting material, an electron transfer material, an electron injection material or the like in an organic light emitting device. Particularly, the compound of Chemical Formula 1 may be used as a light emitting material of an organic light emitting device, specifically as a host material of the light emitting layer, and particularly, as a phosphorescent host material, and in this case, an organic light emitting device having high efficiency and long life span can be provided. According to one specific example, the compound of Chemical Formula 1 may be used as a fluorescent blue host material.

According to one embodiment, the compound of Chemical Formula 1 may particularly function as an organic light emitting compound, therefore, the organic material layer that includes the compound of Chemical Formula 1 is a light emitting layer.

According to another embodiment, the compound of Chemical Formula 1 may function as a light emitting host material, therefore, the organic material layer that includes the compound of Chemical Formula 1 further includes a light emitting dopant.

According to another embodiment, the organic material layer that includes the compound of Chemical Formula 1 further includes a fluorescent dopant.

According to another embodiment, the organic material layer that includes the compound of Chemical Formula 1 further includes a blue fluorescent dopant.

According to another embodiment, the organic material layer that includes the compound of Chemical Formula 1 further includes a phosphorescent dopant.

The light emitting dopant applied to an organic light emitting device of the present invention is not particularly limited, however, the compounds of the following Chemical Formula 10 may be illustrated.

$$M^1L^{101}L^{102}L^{103} \qquad \text{[Chemical Formula 10]}$$

Herein, $M^1$ is selected from the group consisting of metals of group 7, group 8, group 9, group 10, group 11, group 13, group 14, group 15 and group 16, and ligands $L^{101}$, $L^{102}$ and $L^{103}$ are each independently selected from the following structures.

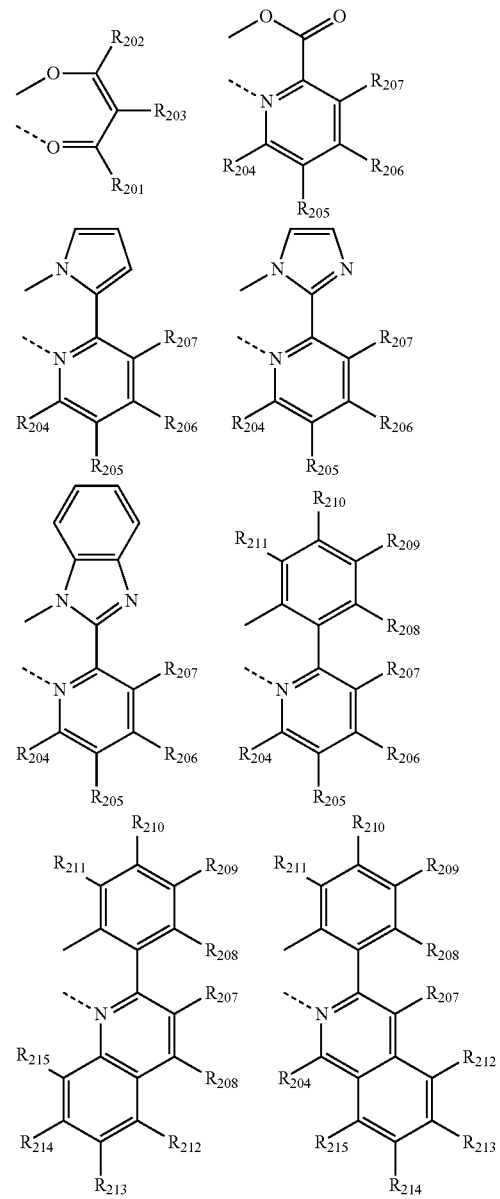

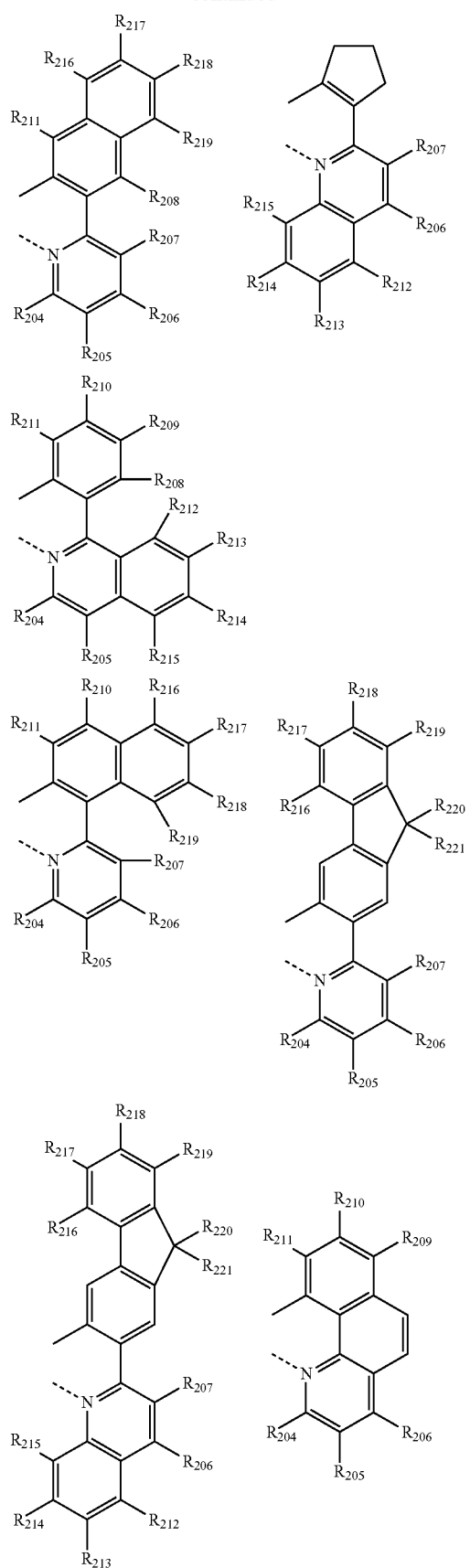
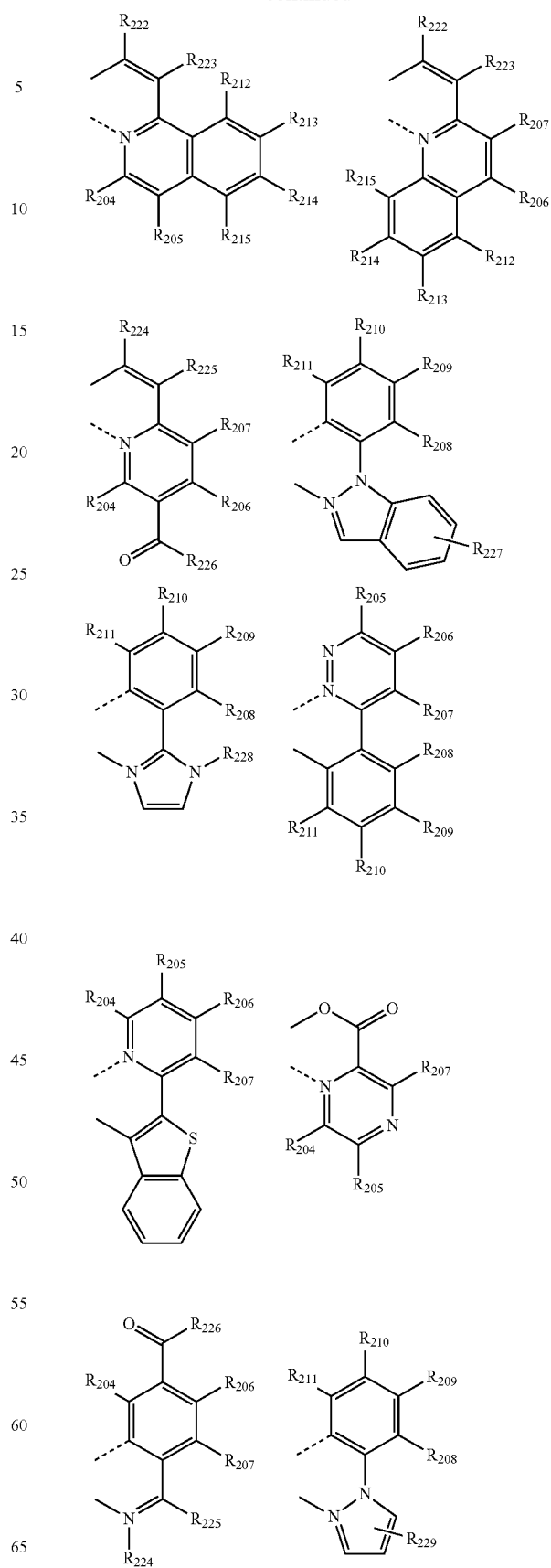

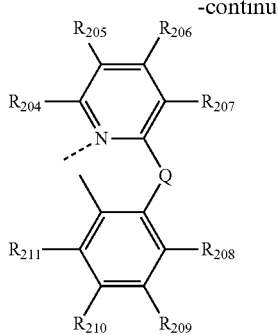

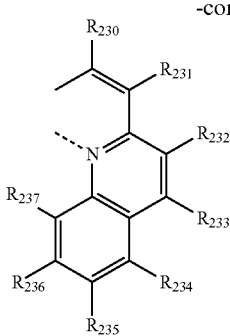

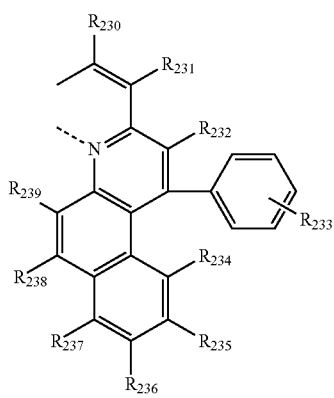

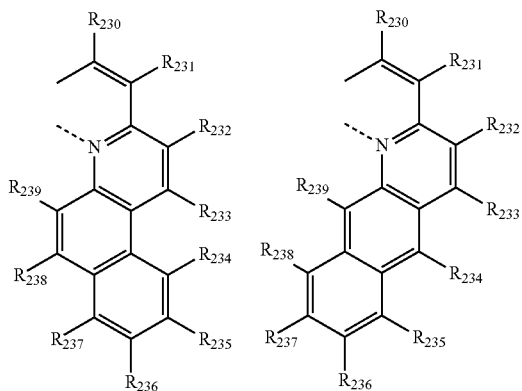

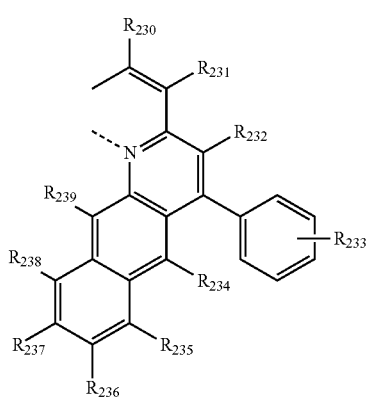

In Chemical Formula 10, $R_{201}$ to $R_{203}$ are each independently hydrogen, deuterium, $C_1$-$C_{30}$ alkyl in which halogen is substituted or unsubstituted, $C_6$-$C_{30}$ aryl in which $C_1$-$C_{30}$ alkyl is substituted or unsubstituted, or halogen;

$R_{204}$ to $R_{219}$ are each independently hydrogen, deuterium, substituted or unsubstituted $C_1$-$C_{30}$ alkyl, substituted or unsubstituted alkoxy, substituted or unsubstituted $C_3$-$C_{30}$ cycloalkyl, substituted or unsubstituted $C_2$-$C_{30}$ alkenyl, substituted or unsubstituted $C_6$-$C_{30}$ aryl, substituted or unsubstituted mono- or di-($C_1$-$C_{30}$)alkylamino, substituted or unsubstituted mono- or di-($C_6$-$C_{30}$)arylamino, SF5, substituted or unsubstituted tri($C_1$-$C_{30}$)alkylsilyl, substituted or unsubstituted di($C_1$-$C_{30}$)alkyl($C_6$-$C_{30}$)arylsilyl, substituted or unsubstituted tri($C_6$-$C_{30}$)arylsilyl, cyano, or halogen;

$R_{220}$ to $R_{223}$ are each independently hydrogen, deuterium, $C_1$-$C_{30}$ alkyl in which halogen is substituted or unsubstituted, $C_6$-$C_{30}$ aryl in which $C_1$-$C_{30}$ alkyl is substituted or unsubstituted;

$R_{224}$ and $R_{225}$ are each independently hydrogen, deuterium, substituted or unsubstituted $C_1$-$C_{30}$ alkyl, substituted or unsubstituted $C_6$-$C_{30}$ aryl, or halogen, or $R_{224}$ and $R_{225}$ may form a monocyclic or multicyclic aliphatic ring, or a monocyclic or multicyclic aromatic ring, by being linked through $C_3$-$C_{12}$ alkylene or $C_3$-$C_{12}$ alkenylene that does or does not include a fused ring;

$R_{226}$ is substituted or unsubstituted $C_1$-$C_{30}$ alkyl, substituted or unsubstituted $C_6$-$C_{30}$ aryl, substituted or unsubstituted $C_3$-$C_{30}$ heteroaryl, or halogen;

$R_{227}$ to $R_{229}$ are each independently hydrogen, deuterium, substituted or unsubstituted $C_1$-$C_{30}$ alkyl, substituted or unsubstituted $C_6$-$C_{30}$ aryl, or halogen;

$R_{230}$ and $R_{231}$ are each independently hydrogen, $C_1$-$C_{20}$ alkyl in which halogen is substituted or unsubstituted, $C_6$-$C_{20}$ aryl, halogen, cyano, tri($C_1$-$C_{20}$)alkylsilyl, di($C_1$-$C_{20}$)alkyl($C_6$-$C_{20}$)arylsilyl, tri($C_6$-$C_{20}$)arylsilyl, $C_1$-$C_{20}$ alkoxy, $C_1$-$C_{20}$ alkylcarbonyl, $C_6$-$C_{20}$ arylcarbonyl, di($C_1$-$C_{20}$)alkylamino or di($C_6$-$C_{20}$)arylamino, or $R_{230}$ and $R_{231}$ form a monocyclic or multicyclic aliphatic ring, or a monocyclic or multicyclic aromatic ring, by being linked through $C_3$-$C_{12}$ alkylene or $C_3$-$C_{12}$ alkenylene that does or does not include a fused ring;

The alkyl, aryl, or a monocyclic or multicyclic aliphatic ring or a monocyclic or multicyclic aromatic ring formed by being linked through $C_3$-$C_{12}$ alkylene or $C_3$-$C_{12}$ alkenylene that does or does not include a fused ring, which are included in $R_{230}$ and $R_{231}$, may be further substituted with one or more substituents selected from $C_1$-$C_{20}$ alkyl in which halogen is substituted or unsubstituted, halogen, cyano, tri($C_1$-$C_{20}$)alkylsilyl, di($C_1$-$C_{20}$)alkyl($C_6$-$C_{20}$)arylsilyl, tri ($C_6$-$C_{20}$)arylsilyl, $C_1$-$C_{20}$ alkoxy, $C_1$-$C_{20}$ alkylcarbonyl, $C_6$-$C_{20}$ arylcarbonyl, di($C_1$-$C_{20}$)alkylamino, di($C_6$-$C_{20}$)arylamino, phenyl, naphthyl, anthryl, fluorenyl or spirobifluorenyl, or may be further substituted with phenyl or fluorenyl in which one or more substituents selected from the group consisting of ($C_1$-$C_{20}$)alkyl in which halogen is substituted or unsubstituted, halogen, cyano, tri($C_1$-$C_{20}$)alkylsilyl, di($C_1$-$C_{20}$)alkyl($C_6$-$C_{20}$)arylsilyl, tri($C_6$-$C_{20}$)arylsilyl, ($C_1$-$C_{20}$)alkoxy, ($C_1$-$C_{20}$)alkylcarbonyl, ($C_6$-$C_{20}$)arylcarbonyl, di($C_1$-$C_{20}$)alkylamino, di($C_6$-$C_{20}$)arylamino, phenyl, naphthyl, anthryl, fluorenyl, and spirobifluorenyl are substituted;

$R_{232}$ to $R_{239}$ are each independently hydrogen, ($C_1$-$C_{20}$) alkyl in which halogen is substituted or unsubstituted, ($C_1$-$C_{20}$)alkoxy, ($C_3$-$C_{12}$)cycloalkyl, halogen, cyano, ($C_6$-$C_{20}$) aryl, ($C_4$-$C_{20}$)heteroaryl, tri($C_1$-$C_{20}$)alkylsilyl, di($C_1$-$C_{20}$)alkyl($C_6$-$C_{20}$)arylsilyl or tri($C_6$-$C_{20}$)arylsilyl; and Q is

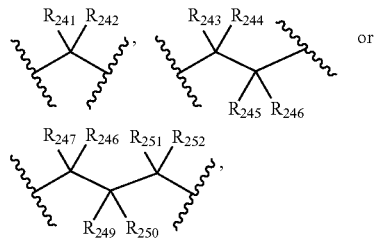

and $R_{241}$ to $R_{252}$ are each independently hydrogen, $C_1$-$C_{60}$ alkyl in which halogen is substituted or unsubstituted, $C_1$-$C_{30}$ alkoxy, halogen, $C_6$-$C_{60}$ aryl, cyano, $C_5$-$C_{60}$ cycloalkyl, or $R_{241}$ to $R_{252}$ may form a $C_5$-$C_7$ spiro ring or a $C_5$-$C_9$ fused ring by being linked to an adjacent substituent through alkylene or alkenylene, or may form a $C_5$-$C_7$ fused ring by being linked to $R_{207}$ or $R_{208}$ through alkylene or alkenylene.

$M^1$ is selected from Ir, Pt, Pd, Rh, Re, Os, Tl, Pb, Bi, In, Sn, Sb, Te, Au and Ag, and the compound of Chemical Formula 10 includes those illustrated in Korean Patent Application No. 10-2009-0037519, but is not limited thereto.

In the organic light emitting device of the present invention, the organic material layer that includes the compound of Chemical Formula 1 may further include one or more compounds selected from the group consisting of arylamine-based compounds or styrylarylamine-based compounds. The arylamine-based compound or styrylarylamine-based compound also includes those illustrated in Korean Patent Application No. 10-2008-0123276 or Korean Patent Application No. 10-2008-0107606, but is not limited thereto.

In addition, in the organic light emitting device of the present invention, the organic material layer that includes the compound of Chemical Formula 1 may further include one or more metals or complex compounds selected from the group consisting of group 1, group 2, period 4 and period 5 transition metals, lanthanide-series metals, and organic metals of d-transition atoms.

The organic light emitting device according to the present invention may be manufactured as an organic light emitting device that emits white light by further including one or more organic materials that emit blue, red or green light in addition to the compound of Chemical Formula 1. For example, the organic light emitting device may be manufactured to emit white light by including two or more light emitting materials in one organic material layer, or including two or more light emitting layers that emit different light emitting colors.

The organic light emitting device may include a light emitting layer and a charge generation layer together.

In the organic light emitting device according to the present invention, materials other than the compound of Chemical Formula 1 are illustrated below, however, these are for the illustrative purposes only, and do not intend to limit the scope of the present invention, and these materials may be substituted with materials known in the related art.

As the anode material, materials having relatively large work function may be used, and transparent conductive oxides, metals, conductive polymers or the like may be used.

As the cathode material, materials having relatively small work function may be used, and metals, metal oxides, conductive polymers or the like may be used.

As the hole transfer material, a pyrazoline derivative, an arylamine-based derivative, a stilbene derivative, a triphenyldiamine derivative or the like may be used, and a low molecular or high molecular material may also be used.

As the light emitting material, a red, green or blue light emitting material may be used, and when necessary, two or more light emitting materials may be mixed and used. In addition, as the light emitting material, a fluorescent material may be used, but a phosphorescent material may also be used. As the light emitting material, materials that emit alone by bonding the holes and the electrons injected from an anode and a cathode, respectively, may be used, however, materials in which a host material and a dopant material are both involved in light emitting may also be used.

As the electron transfer material, an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, 8-hydroxyquinoline and a metal complex of a derivative thereof, or the like, may be used, and a high molecular material as well as a low molecular material may also be used.

As the electron injection material, for example, LiF is typically used in the related industry, however, the present invention is not limited thereto.

Hereinafter, an organic light emitting compound according to the present invention, the preparation method thereof, and light emitting properties of the device will be described with reference to representative compounds of the present invention in order to understand the present invention in detail, however, this is only to illustrate the embodiments, and the scope of the present invention is not limited to these compounds.

PREPARATION EXAMPLE 1

Preparation of Compound 1

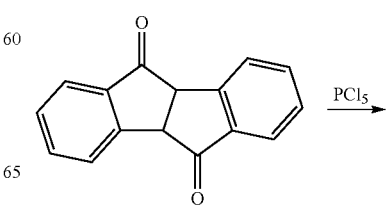

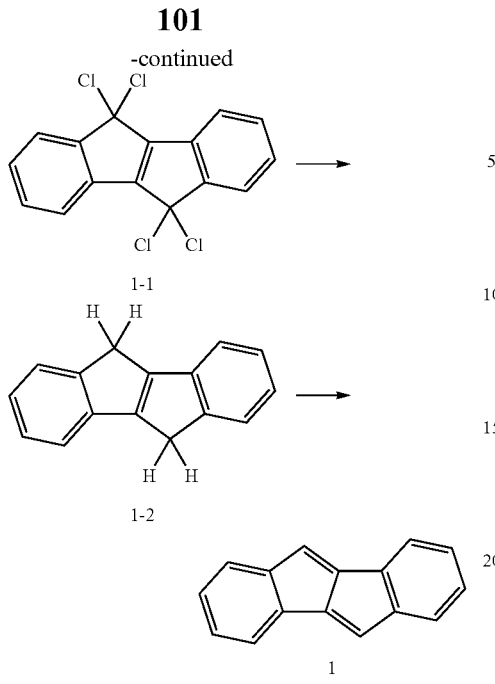

1-1

1-2

1

Preparation of Compound 1-1

After 10 g (42.7 mmol) of dibenzopentalenedione and 22.5 g (108 mmol) of phosphorus pentachloride were placed in a vessel, the vessel was sealed and heated until a liquid formed, and then an excess acetic acid solution was added thereto and the result was stirred for 48 hours. After the reaction completed, the compound was filtered using water, and then the liquid was extracted using water and diethylether. The solution was vacuum distilled, and separated and purified using a column, resulting in 5.8 g (16.9 mmol) of Compound 1-1.

Preparation of Compound 1-2

5 g (14.6 mmol) of Compound 1-1 was dissolved in acetic acid, and then the mixture was heated under reflux for 4 hours. After the reaction completed, the result was extracted using diethylether and water, and recrystallized using ethyl acetate, resulting in 3 g (14.6 mmol) of Compound 1-2.

Preparation of Compound 1

A solution in which 6 g (29.4 mmol) of Compound 1-2 and 0.12 ml (4.7 mmol) of bromine were dissolved in 300 ml of carbon disulfide was stirred for 12 hours at 0° C. After the stirring, the carbon disulfide was removed by vacuum distillation, and 19.6 g (117.5 mmol) of silver nitrate was added thereto. The mixture was dissolved in 250 ml of benzene, and the result was heated under reflux for 2 hours. After the reaction completed, the solution was vacuum distilled, and separated and purified using a column, resulting in 2.8 g (14.1 mmol) of Compound 1.

PREPARATION EXAMPLE 2

Preparation of Compound 5

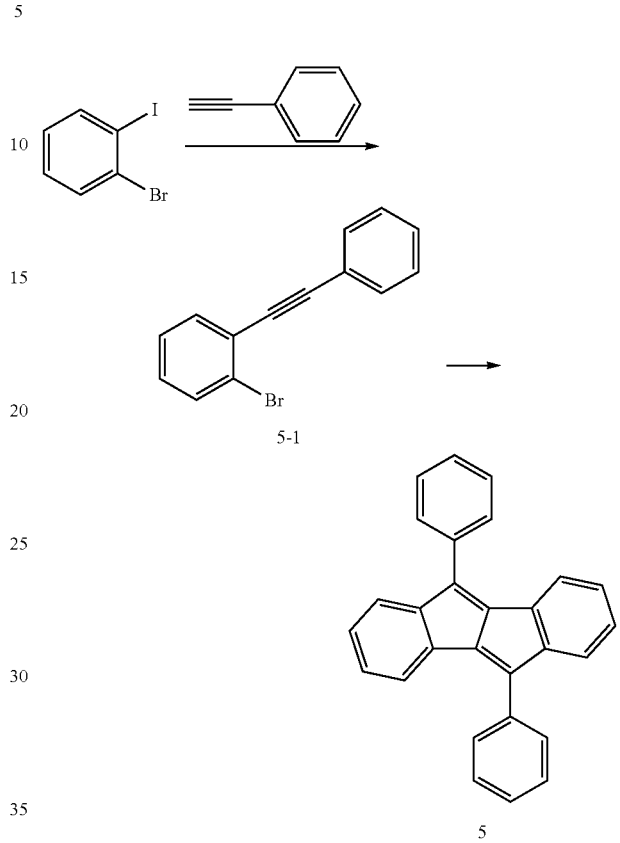

5-1

5

Preparation of Compound 5-1

To a solution in which 337 mg (1.77 mmol) of CuI and 744 mg (1.06 mmol) of $Pd(PPh_3)_2Cl_2$ were dissolved in 150 ml of triethylamine, 3.2 g (31.8 mmol) of phenylacetylene and 10 g (35.3 mml) of 1-bromo-2-iodobenzene were added in consecutive order, and the mixture was stirred for 24 hours at room temperature. After the reaction completed, the result was washed with an ammonium chloride solution and then extracted using ethyl acetate. The solution was vacuum distilled, and separated and purified using a column, resulting in 9 g (35.0 mmol) of Compound 5-1.

Preparation of Compound 5

After 4.3 g (39 mmol) of hydroquinone, 12.67 g (38.9 mmol) of $Cs_2CO_3$, 5.9 g (38.9 mmol) of CsF, 0.12 g (0.59 mmol) of $P(t-Bu)_3$ and 0.27 g (0.29 mmol) of $Pd_2(dba)_3$ were placed in a reaction vessel, a solution in which 5 g (19.45 mmol) of Compound 5-1 was dissolved in 150 ml of 1,4-dioxane was added thereto, and then the mixture was stirred for 24 hours at 120° C. After the reaction completed, the reaction solution was dissolved in toluene and then extracted, and residual water was removed using magnesium sulfate. The solution was vacuum distilled, and separated and purified using a column, resulting in 5.5 g (15.5 mmol) of Compound 5.

PREPARATION EXAMPLE 3

Preparation of Compound 6

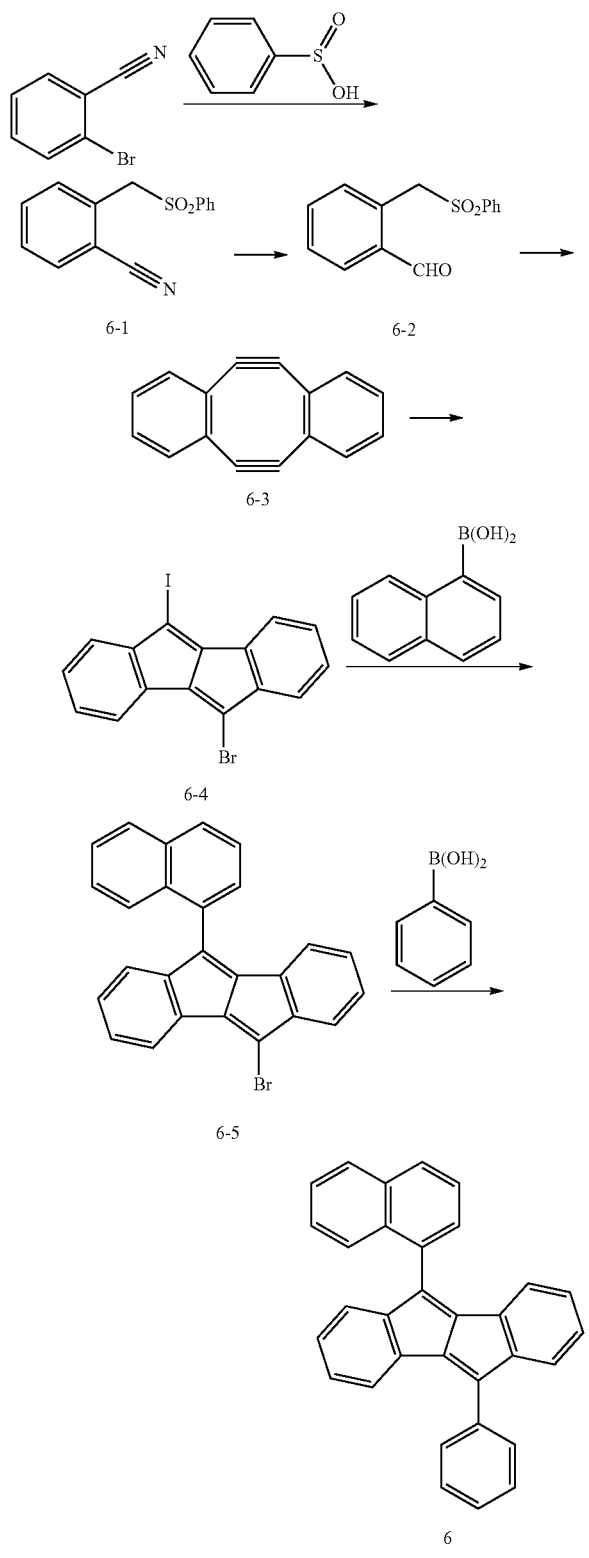

Preparation of Compound 6-1

A solution in which 15 g (82.4 mmol) of 2-bromobenzonitrile and 16.2 g (98.9 mmol) of PhSOOH were dissolved in 100 ml of DMF was heated under reflux for 2 hours at 80° C. After the reaction completed, the result was extracted using ethyl acetate and water, and the solution obtained was vacuum distilled. The obtained solid was separated and purified using a column, and 18.0 g (70.0 mmol) of Compound 6-1 was obtained.

Preparation of Compound 6-2

15 g (58.3 mmol) of Compound 6-1, 60 ml of 1M DIBAL solution and 45 ml of dichloromethane was placed in a reaction vessel in consecutive order, and the mixture was stirred for 2 hours at −78° C. After that, an excess 1M ammonium chloride solution was added thereto and the result was stirred for additional 1 hour. After the reaction completed, the result was extracted using dichloromethane and a hydrochloric acid solution, and the solution obtained was vacuum distilled. The obtained solid was separated and purified using a column, and 12.1 g (46.6 mmol) of Compound 6-2 was obtained.

Preparation of Compound 6-3

After 10 g (38.4 mmol) of Compound 6-2 and 7 ml (46 mmol) of ClP(O)OEt$_2$ were dissolved in 125 ml of THF, the mixture was stirred for 15 minutes at −78° C. After that, 75 ml of an 1M LiHMDS solution was placed in a reaction vessel, and the result was stirred for 2 hours at room temperature. After the temperature of the reaction vessel was again lowered to −78° C., 200 ml of an 1M DIBAL solution was added thereto, and the result was stirred for 2 hours at room temperature. After the reaction completed, an ammonium chloride solution was added thereto, the result was shortly stirred, then the solution was extracted using dichloromethane, and the liquid obtained was vacuum distilled. The obtained solid was separated and purified using a column, and 4.6 g (23 mmol) of Compound 6-3 was obtained.

Preparation of Compound 6-4

After 5 g (25 mmol) of Compound 6-3 and 4.7 g (27.4 mmol) of IBr were dissolved in 150 ml of dichloromethane, the mixture was stirred for 1 hour at −78° C. After the reaction completed, a sodium sulfite solution was added thereto, and then the result was shortly stirred. Next, the solution was extracted using an organic solvent, and the liquid obtained was vacuum distilled. The obtained solid was separated and purified using a column, and 6.3 g (15.4 mmol) of Compound 6-4 was obtained.

Preparation of Compound 6-5

After 5 g (12.2 mmol) of Compound 6-4, 3.1 g (18.4 mmol) of 1-naphthyl boronic acid, 1.4 g (1.2 mmol) of Pd(PPh$_3$)$_4$, and 7.8 g (36.9 mmol) of K$_3$PO$_4$ were dissolved in 37 ml of 1,4-dioxane and 13 ml of water, the mixture was heated under reflux for 2 hours at 90° C. After the reaction completed, an ammonium chloride solution was added thereto, the solution was extracted using an organic solvent, and the liquid obtained was vacuum distilled. The obtained solid was separated and purified using a column, and 4.3 g (10.4 mmol) of Compound 6-5 was obtained.

Preparation of Compound 6

After 6 g (14.7 mmol) of Compound 6-5, 2.7 g (22.1 mmol) of phenylboronic acid, 1.7 g (1.5 mmol) of Pd(PPh$_3$)$_4$ and 9.4 g (44.2 mmol) of K$_3$PO$_4$ were dissolved in 45 ml of 1,4-dioxane and 15 ml of water, the mixture was heated under reflux for 2 hours at 90° C. After the reaction completed, an ammonium chloride solution was added thereto, the solution was extracted using an organic solvent, and the liquid obtained was vacuum distilled. The obtained solid was separated and purified using a column, and 5.4 g (13.3 mmol) of Compound 6 was obtained.

PREPARATION EXAMPLE 4

Preparation of Compound 66

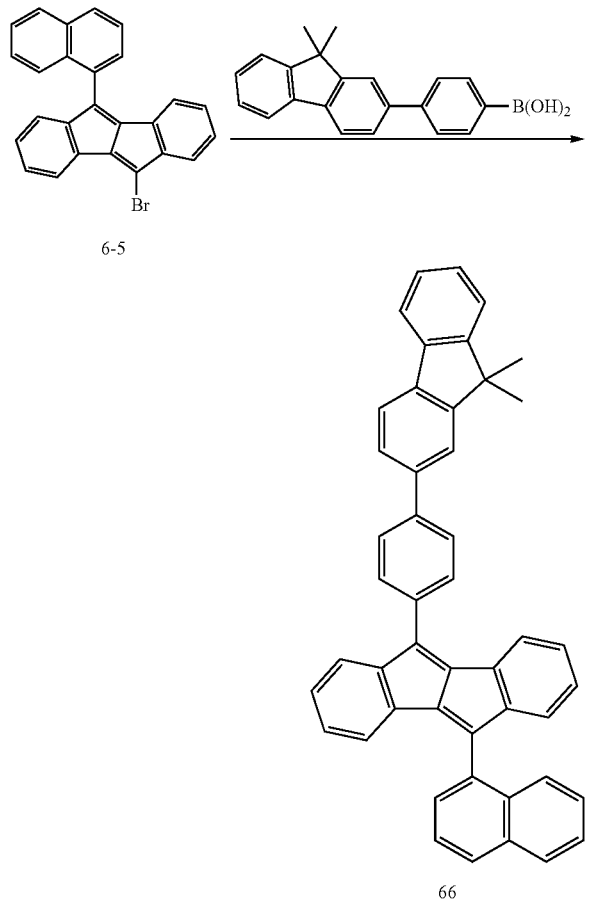

66

After 5 g (12.2 mmol) of Compound 6-5, 5.8 g (18.4 mmol) of phenylboronic acid, 1.4 g (1.2 mmol) of Pd(PPh$_3$)$_4$, and 7.8 g (36.9 mmol) of K$_3$PO$_4$ were dissolved in 37 ml of 1,4-dioxane and 13 ml of water, the mixture was heated under reflux for 2 hours at 90° C. After the reaction completed, an ammonium chloride solution was added thereto, the solution was extracted using an organic solvent, and the liquid obtained was vacuum distilled. The obtained solid was separated and purified using a column, and 5.5 g (9.2 mmol) of Compound 66 was obtained.

PREPARATION EXAMPLE 5

Preparation of Compound 82

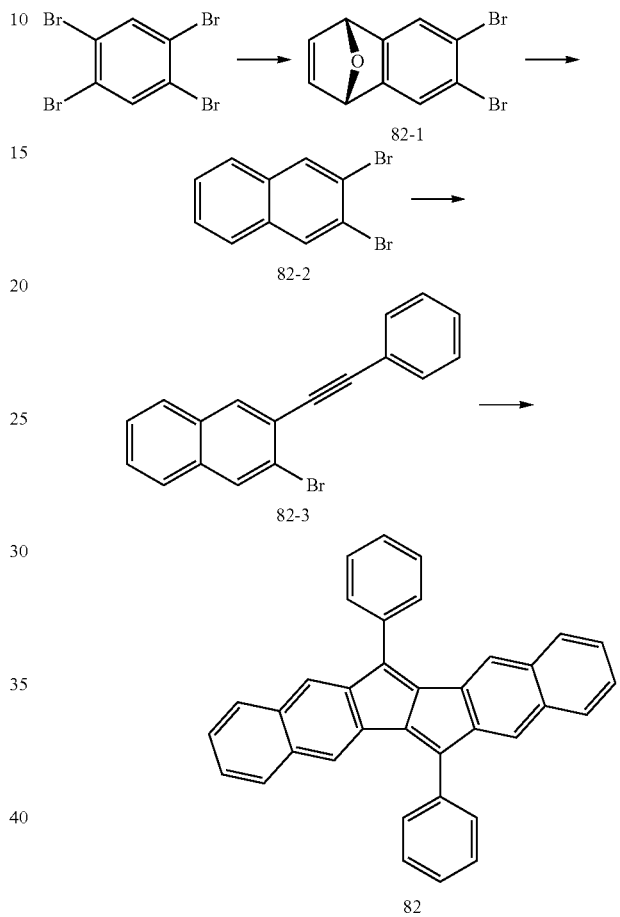

Preparation of Compound 82-1

After 4 g (10 mmol) of 2,3,5,6-tetrabromobenzene and 5 ml (70 mmol) of furan were dissolved in 50 ml of THF, 25 ml of a 0.5M n-BuLi solution was added thereto at −78° C., and then the mixture was stirred for 18 hours. After the reaction completed, small amount of methanol was added thereto, the result was extracted using an organic solvent, and the solution obtained was vacuum distilled. The obtained solid was recrystallized using hexane and methanol, and 2.0 g (6.5 mmol) of Compound 82-1 was obtained.

Preparation of Compound 82-2

8.7 g (132 mmol) of zinc powder and 8.7 ml (79 mmol) of titanium tetrachloride were dissolved in 200 ml of THF, and the mixture was heated under reflux for 18 hours. After the mixture was cooled to room temperature, a solution in which 4 g (13.2 mmol) of Compound 82-1 was dissolved in THF was added thereto, and the result was heated under reflux for 18 hours. After the reaction completed, an HCl solution was introduced thereto, the result was extracted using an organic solvent, and the solution obtained was vacuum distilled. The obtained solid was separated and purified using a column, and 3.1 g (11.0 mmol) of Compound 82-2 was obtained.

Preparation of Compound 82-3

2 g (7.0 mmol) of Compound 82-2, 0.7 g (7.0 mmol) of phenylacetylene, 0.3 g (0.3 mmol) of Pd(PPh$_3$)$_2$Cl$_2$ and 4.5 g (21.0 mmol) of CuI were placed in a reaction vessel in consecutive order, dissolved in 30 ml of triethylamine, and the mixture was heated under reflux for 18 hours at 100° C. After the reaction completed, an HCl solution was introduced thereto, the result was extracted using an organic solvent, and then residual water was removed using sodium sulfate. After the solution was vacuum distilled, the obtained solid was separated and purified using a column, and 1.0 g (3.3 mmol) of Compound 82-3 was obtained.

Preparation of Compound 82

5.5 g (18.0 mmol) of Compound 82-3, 5.9 g (9.0 mmol) of Ni(PPh$_3$)$_2$Cl$_2$ and 1.8 g (26.9 mmol) of zinc powder were placed in a reaction vessel in consecutive order, were dissolved in 80 ml of tetrahydrofuran and 20 ml of diethylether, and the mixture was heated under reflux for 24 hours at 80° C. After the reaction completed, the result was extracted using an organic solvent, and the solution obtained was vacuum distilled. The obtained solid was separated and purified using a column, and 1.5 g (3.2 mmol) of Compound 82 was obtained.

PREPARATION EXAMPLE 6

Preparation of Compound 107

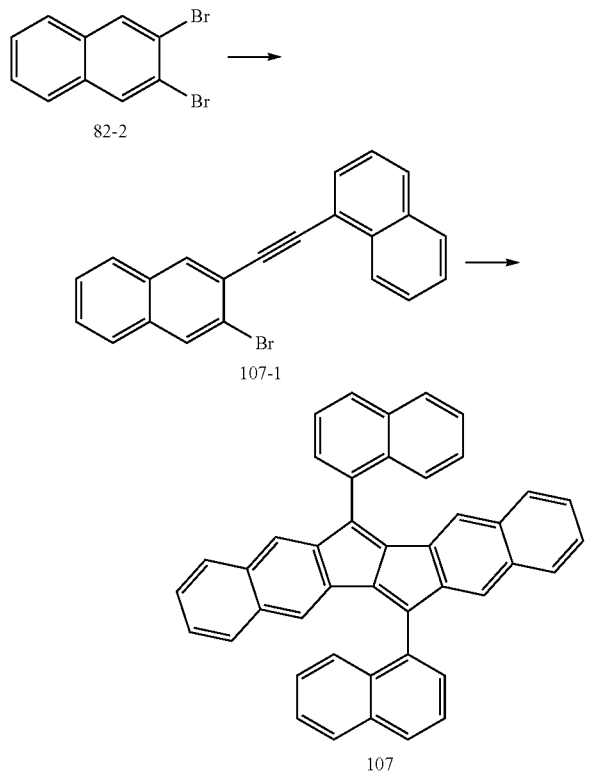

Preparation of Compound 107-1

4 g (14.0 mmol) of Compound 82-2, 2.1 g (14.0 mmol) of phenylacetylene, 0.5 g (0.7 mmol) of Pd(PPh$_3$)$_2$Cl$_2$ and 8.9 g (42.0 mmol) of CuI were placed in a reaction vessel in consecutive order, were dissolved in 60 ml of triethylamine, and the mixture was heated under reflux for 18 hours at 100° C. After the reaction completed, an HCl solution was introduced thereto, the result was extracted using an organic solvent, and then residual water was removed using sodium sulfate. After the solution was vacuum distilled, the obtained solid was separated and purified using a column, and 2.1 g (5.9 mmol) of Compound 107-1 was obtained.

Preparation of Compound 107

4 g (11.2 mmol) of Compound 107-1, 3.7 g (5.6 mmol) of Ni(PPh$_3$)$_2$Cl$_2$ and 1.1 g (16.8 mmol) of zinc powder were placed in a reaction vessel in consecutive order, were dissolved in 48 ml of tetrahydrofuran and 12 ml of diethylether, and the mixture was heated under reflux for 24 hours at 80° C. After the reaction completed, the result was extracted using an organic solvent, and the solution obtained was vacuum distilled. The obtained solid was separated and purified using a column, and 683 mg (1.2 mmol) of Compound 107 was obtained.

PREPARATION EXAMPLE 7

Preparation of Compound 116

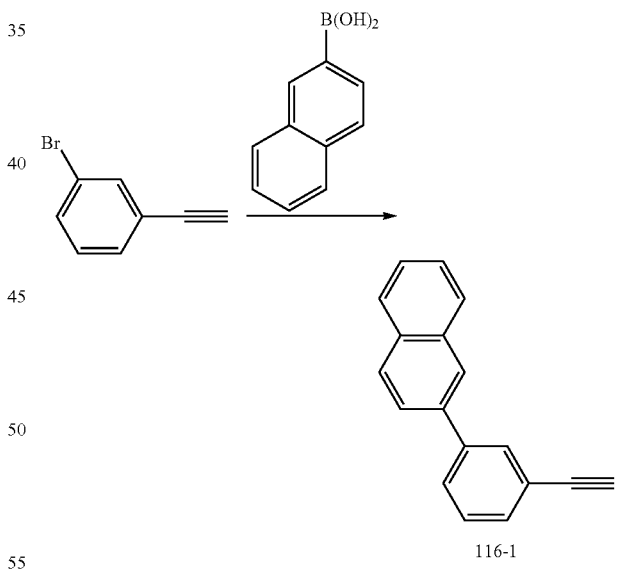

Preparation of Compound 116-1

After 10 g (55.2 mmol) of 3-bromophenylacetylene, 14.3 g (82.9 mmol) of 2-naphthyl boronic acid, 6.4 g (5.5 mmol) of Pd(PPh$_3$)$_4$ and 35.2 g (165 mmol) of K$_3$PO$_4$ were dissolved in 150 ml of 1,4-dioxane and 50 ml of water, the mixture was heated under reflux for 2 hours at 90° C. After the reaction completed, an ammonium chloride solution was added thereto, the solution was extracted using an organic solvent, and the liquid obtained was vacuum distilled. The obtained solid was separated and purified using a column, and 10.2 g (44.7 mmol) of Compound 116-1 was obtained.

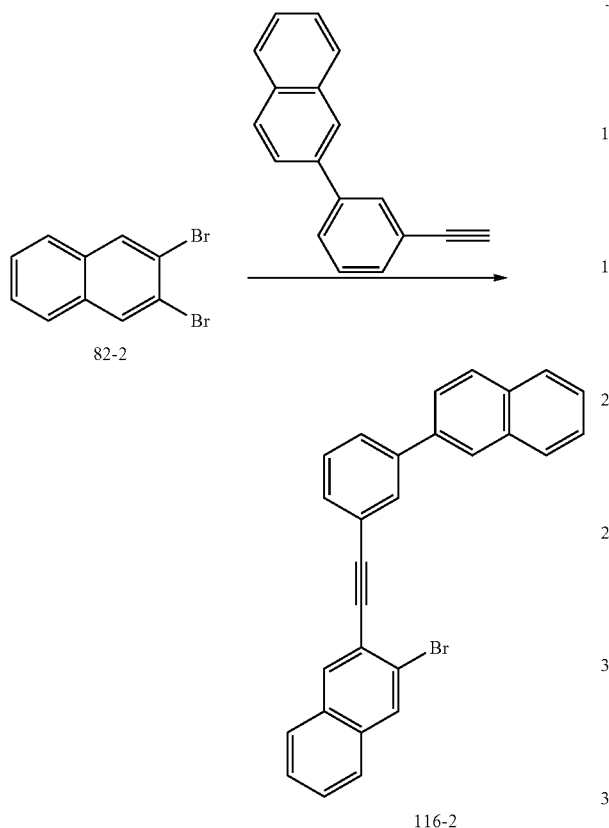

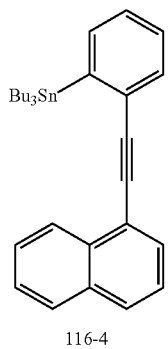

Preparation of Compound 116-2

To a solution in which 417 mg (2.2 mmol) of CuI and 922 mg (1.3 mmol) of Pd(PPh$_3$)$_2$Cl$_2$ were dissolved in 400 ml of triethylamine, 10 g (43.8 mmol) of Compound 116-1 and 12.5 g (43.8 mml) of Compound 82-2 were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 9 g (43.4 mmol) of Compound 116-2.

Preparation of Compound 116-3

After the temperature of a solution in which 8 g (24.0 mmol) of 2-bromo-3-iodonaphthalene was dissolved in 12 ml of tetrahydrofuran was lowered to −78° C., a 2.5M n-BuLi solution was added thereto, and the mixture was stirred for 40 minutes. After the reaction vessel was warmed to room temperature, 8.6 g (26.4 mmol) of SnBu$_3$Cl was added thereto, and the result was stirred for 18 hours. When the reaction completed, the result was washed with an ammonium chloride solution, extracted using an organic solvent, and residual water was removed using magnesium sulfate. The solution was vacuum distilled, and then separated and purified using a column, resulting in 11.9 g (24.0 mmol) of 116-3.

Preparation of Compound 116-4

To a solution in which 38 mg (0.1 mmol) of CuI and 85 mg (0.1 mmol) of Pd(PPh$_3$)$_2$Cl$_2$ were dissolved in 20 ml of triethylamine, 2 g (4.0 mmol) of Compound 116-3 and 0.6 g (4.0 mml) of 1-ethynylnaphthalene were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 2.2 g (3.9 mmol) of Compound 116-4.

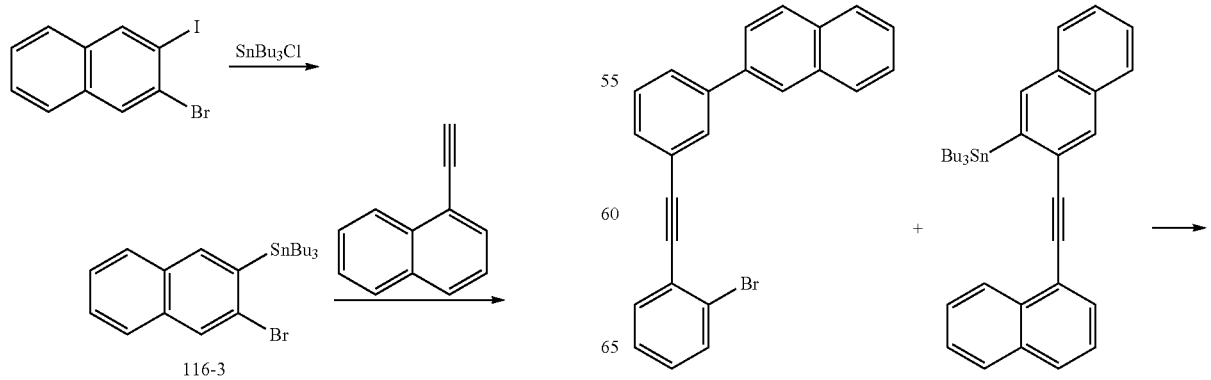

-continued

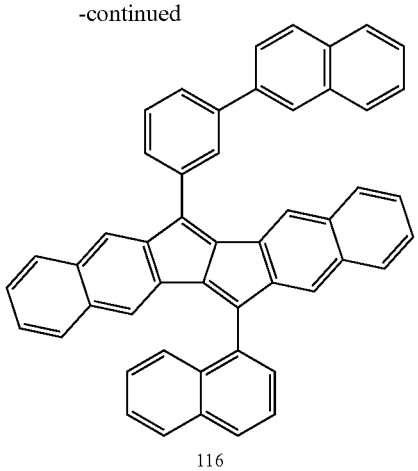

116

Preparation of Compound 116

1.1 g (9.7 mmol) of hydroquinone, 3.2 g (9.7 mmol) of Cs$_2$CO$_3$, 1.5 g (9.7 mmol) of CsF, 0.03 g (0.15 mmol) of P(t-Bu)$_3$ and 0.07 g (0.07 mmol) of Pd$_2$(dba)$_3$ were placed in a reaction vessel, and after a solution in which 2.1 g (4.8 mmol) of Compound 116-2 and 3 g (5.3 mmol) of Compound 116-4 were dissolved in 75 ml of 1,4-dioxane was added thereto, the mixture was stirred for 24 hours at 150° C. After the reaction completed, the reaction solution was dissolved in toluene and then extracted, and residual water was removed using magnesium sulfate. The solution was vacuum distilled, and separated and purified using a column, resulting in 1.2 g (1.8 mmol) of Compound 116.

PREPARATION EXAMPLE 8

Preparation of Compound 139

Preparation of Compound 139-1

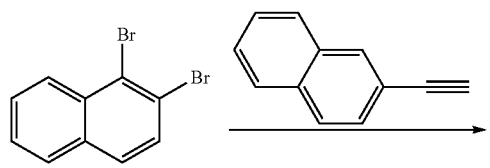

139-1

To a solution in which 0.17 g (0.9 mmol) of CuI and 0.37 g (0.5 mmol) of Pd(PPh$_3$)$_2$Cl$_2$ were dissolved in 400 ml of triethylamine, 5 g (17.5 mmol) of 1,2-dibromonaphthalene and 2.7 g (17.5 mml) of 2-ethynylnaphthalene were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 3 g (8.4 mmol) of Compound 139-1.

Preparation of Compound 139-2

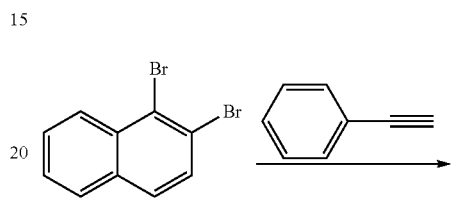

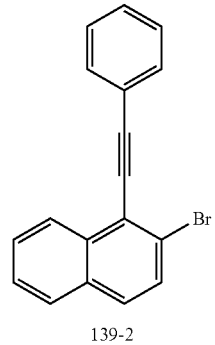

139-2

To a solution in which 0.17 g (0.9 mmol) of CuI and 0.37 g (0.5 mmol) of Pd(PPh$_3$)$_2$Cl$_2$ were dissolved in 400 ml of triethylamine, 5 g (17.5 mmol) of 1,2-dibromonaphthalene and 1.8 g (17.5 mml) of phenylacetylene were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 2.3 g (7.3 mmol) of Compound 139-2.

Preparation of Compound 139

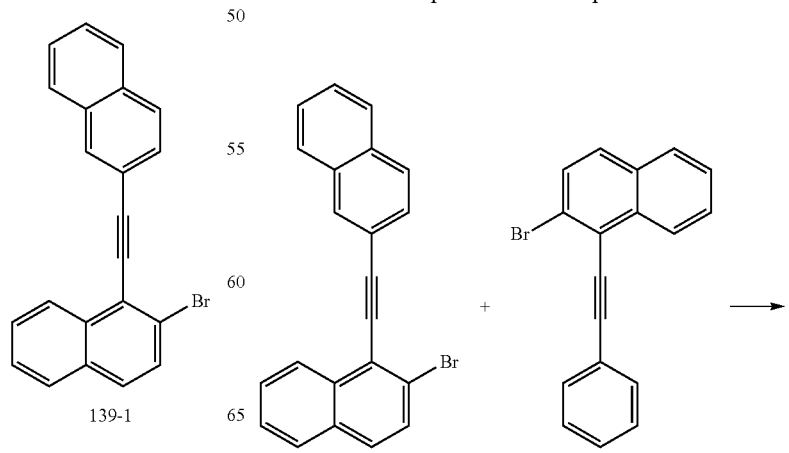

-continued

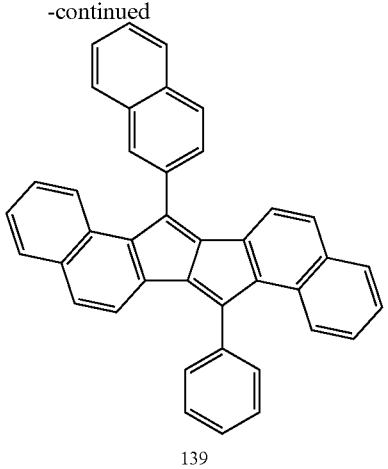

139

1.3 g (11.8 mmol) of hydroquinone, 3.8 g (11.8 mmol) of Cs$_2$CO$_3$, 1.8 g (11.8 mmol) of CsF, 0.03 g (0.17 mmol) of P(t-Bu)$_3$ and 0.08 g (0.09 mmol) of Pd$_2$(dba)$_3$ were placed in a reaction vessel, and after a solution in which 2 g (4.8 mmol) of Compound 139-1 and 2 g (5.3 mmol) of Compound 139-2 were dissolved in 60 ml of 1,4-dioxane was added thereto, the mixture was stirred for 24 hours at 150° C. After the reaction completed, the reaction solution was dissolved in toluene and then extracted, and residual water was removed using magnesium sulfate. The solution was vacuum distilled, and separated and purified using a column, resulting in 1.5 g (3.0 mmol) of Compound 139.

PREPARATION EXAMPLE 9

Preparation of Compound 163

Preparation of Compound 163-1

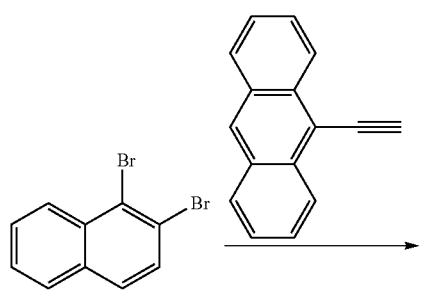

163-1

To a solution in which 0.17 g (0.9 mmol) of CuI and 0.37 g (0.5 mmol) of Pd(PPh$_3$)$_2$Cl$_2$ were dissolved in 400 ml of triethylamine, 5 g (17.5 mmol) of 1,2-dibromonaphthalene and 3.5 g (17.5 mml) of 9-ethynylanthracene were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 2.8 g (6.8 mmol) of Compound 163-1.

Preparation of Compound 163-2

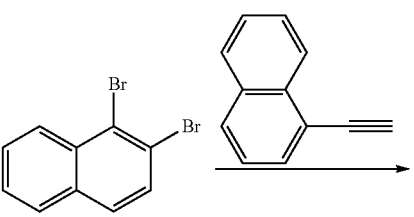

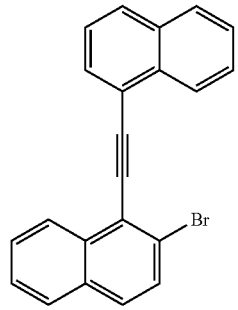

163-2

To a solution in which 0.17 g (0.9 mmol) of CuI and 0.37 g (0.5 mmol) of Pd(PPh$_3$)$_2$Cl$_2$ were dissolved in 400 ml of triethylamine, 5 g (17.5 mmol) of 1,2-dibromonaphthalene and 2.7 g (17.5 mml) of 1-ethynylnaphthalene were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 2.9 g (8.2 mmol) of Compound 163-2.

Preparation of Compound 163

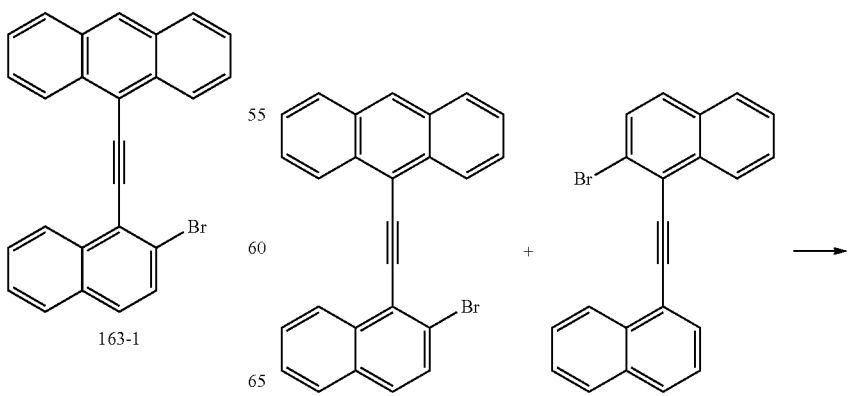

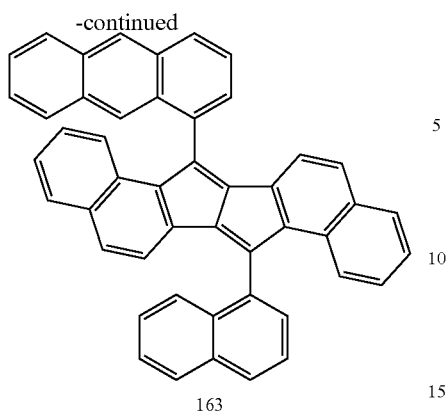

163

1.7 g (15.2 mmol) of hydroquinone, 5.0 g (15.2 mmol) of Cs₂CO₃, 2.3 g (15.2 mmol) of CsF, 0.05 g (0.23 mmol) of P(t-Bu)₃ and 0.10 g (0.11 mmol) of Pd₂(dba)₃ were placed in a reaction vessel, and after a solution in which 3.1 g (7.6 mmol) of Compound 163-1 and 3 g (8.4 mmol) of Compound 163-2 were dissolved in 100 ml of 1,4-dioxane was added thereto, the mixture was stirred for 24 hours at 150° C. After the reaction completed, the reaction solution was dissolved in toluene and then extracted, and residual water was removed using magnesium sulfate. The solution was vacuum distilled, and separated and purified using a column, resulting in 1.8 g (3.0 mmol) of Compound 163.

PREPARATION EXAMPLE 10

Preparation of Compound 206

Preparation of Compound 206-1

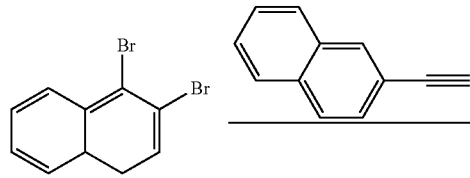

To a solution in which 0.1 g (0.5 mmol) of CuI and 0.22 g (0.3 mmol) of Pd(PPh₃)₂Cl₂ were dissolved in 200 ml of triethylamine, 3 g (10.5 mmol) of 1,2-dibromonaphthalene and 1.6 g (10.5 mml) of 2-ethynylnaphthalene were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 1.6 g (4.5 mmol) of Compound 206-1.

Preparation of Compound 206-2

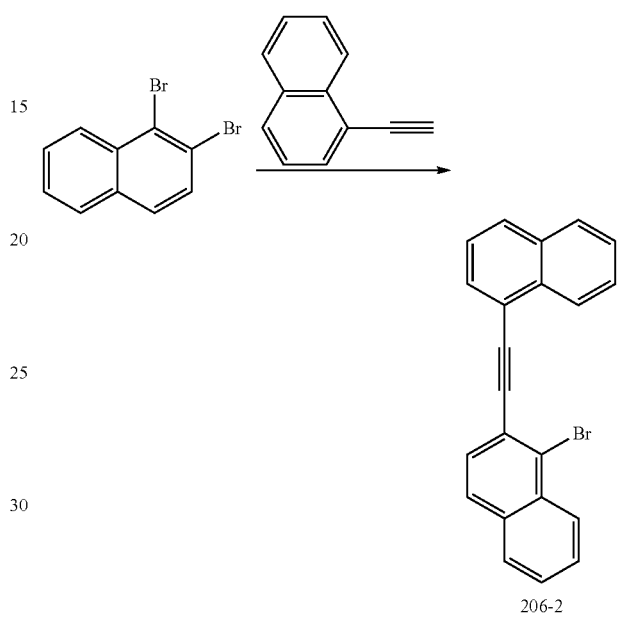

206-2

To a solution in which 0.1 g (0.5 mmol) of CuI and 0.22 g (0.3 mmol) of Pd(PPh₃)₂Cl₂ were dissolved in 200 ml of triethylamine, 3 g (10.5 mmol) of 1,2-dibromonaphthalene and 1.6 g (10.5 mml) of 1-ethynylnaphthalene were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 1.2 g (3.3 mmol) of Compound 206-2.

Preparation of Compound 206

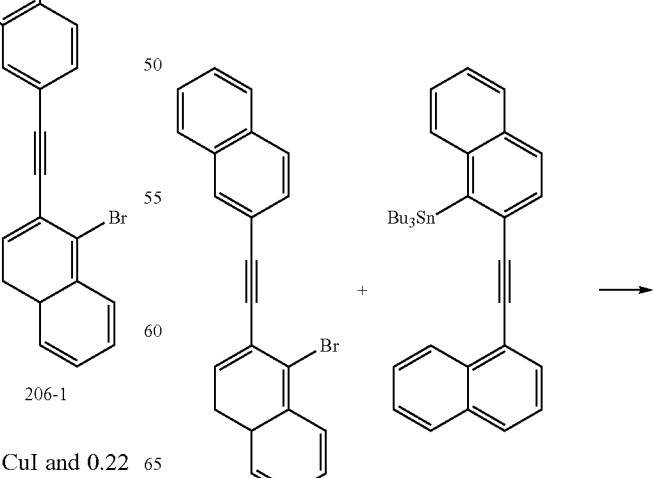

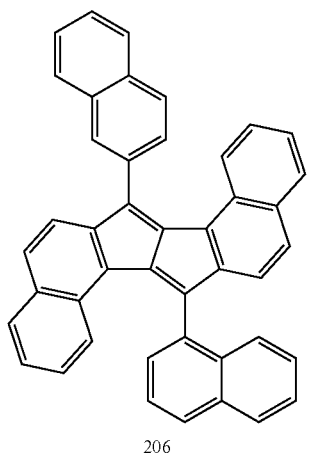

206

1.1 g (10.1 mmol) of hydroquinone, 3.3 g (10.1 mmol) of Cs$_2$CO$_3$, 1.5 g (10.1 mmol) of CsF, 0.04 g (0.2 mmol) of P(t-Bu)$_3$ and 0.07 g (0.08 mmol) of Pd$_2$(dba)$_3$ were placed in a reaction vessel, and after a solution in which 1.8 g (5.0 mmol) of Compound 206-1 and 2 g (5.5 mmol) of Compound 206-2 were dissolved in 100 ml of 1,4-dioxane was added thereto, the mixture was stirred for 24 hours at 150° C. After the reaction completed, the reaction solution was dissolved in toluene and then extracted, and residual water was removed using magnesium sulfate. The solution was vacuum distilled, and separated and purified using a column, resulting in 1.1 g (2.0 mmol) of Compound 206.

PREPARATION EXAMPLE 11

Preparation of Compound 244

Preparation of Compound 244-1

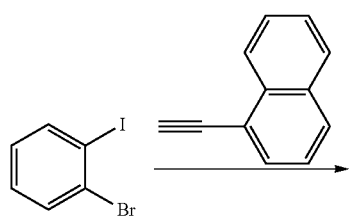

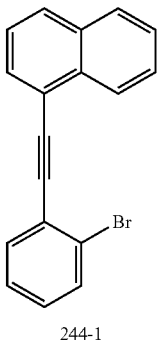

244-1

To a solution in which 0.07 g (0.4 mmol) of CuI and 0.15 g (0.2 mmol) of Pd(PPh$_3$)$_2$Cl$_2$ were dissolved in 60 ml of triethylamine, 2 g (7.0 mmol) of 1-bromo-2-iodobenzene and 1.1 g (7.0 mml) of 1-ethynylnaphthalene were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 1.7 g (5.6 mmol) of Compound 244-1.

Preparation of Compound 244-2

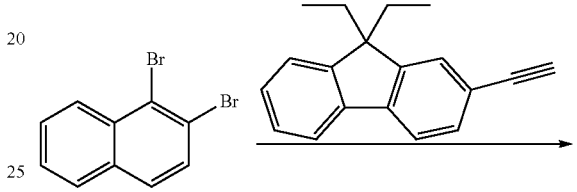

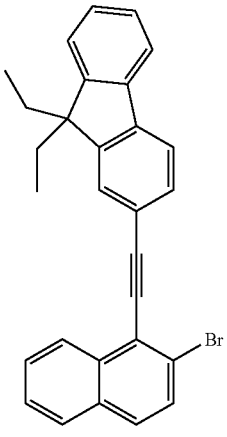

244-2

To a solution in which 0.07 g (0.4 mmol) of CuI and 0.15 g (0.2 mmol) of Pd(PPh$_3$)$_2$Cl$_2$ were dissolved in 80 ml of triethylamine, 2 g (7.0 mmol) of 1,2-dibromonaphthalene and 1.7 g (7.0 mml) of 9,9-diethyl-2-ethynyl-9H-fluorene were added in consecutive order, and the mixture was stirred for 24 hours at room temperature. After the reaction completed, the result was washed with an ammonium chloride solution, and then extracted using ethyl acetate. The solution was vacuum distilled, and then separated and purified using a column, resulting in 1.1 g (2.5 mmol) of Compound 244-2.

Preparation of Compound 244

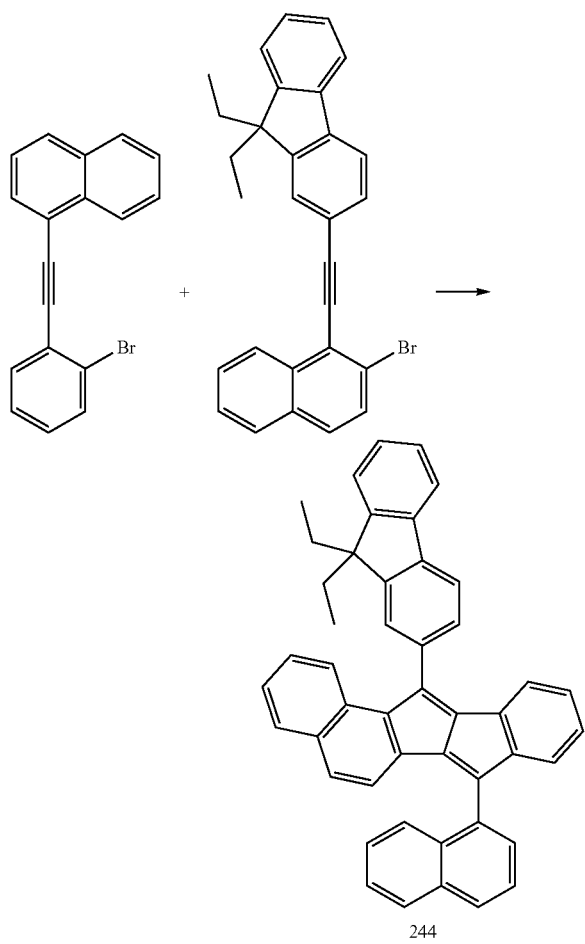

244

1.3 g (11.2 mmol) of hydroquinone, 3.8 g (11.2 mmol) of $Cs_2CO_3$, 1.8 g (11.2 mmol) of CsF, 0.04 g (0.18 mmol) of $P(t-Bu)_3$ and 0.08 g (0.09 mmol) of $Pd_2(dba)_3$ were placed in a reaction vessel, and after a solution in which 1.8 g (5.9 mmol) of Compound 244-1 and 2.9 g (6.4 mmol) of Compound 244-2 were dissolved in 60 ml of 1,4-dioxane was added thereto, the mixture was stirred for 24 hours at 150° C. After the reaction completed, the reaction solution was dissolved in toluene and then extracted, and residual water was removed using magnesium sulfate. The solution was vacuum distilled, and separated and purified using a column, resulting in 1.5 g (2.6 mmol) of Compound 244.

In addition, various compounds represented by Chemical Formulae 1 to 6 may be synthesized by introducing various substituents using well-known methods with any one, two or more mixtures selected from 2,4-dichloropyrido[2,3-d]pyrimidine (manufactured by OChem Incorporation), 2-chloro-pyrido[3,2-d]pyrimidine (manufactured by Anichem LLC), pyrido[4,3-d]pyrimidin-4(3H)-one (manufactured by Aces Pharma, Inc.), 2-chloro-6,7-dimethyl-pteridine (manufactured by International Laboratory Limited), 2-chloropteridine (manufactured by Princeton BioMolecular Research, Inc.), 3-chloroquinoline (manufactured by Texas Biochemicals Inc.), 2,4-dichloroquinoline (manufactured by Shanghai PI Chemicals Ltd), 2,3-dichloroquinoline (manufactured by Aces Pharma, Inc.), 1-chloroisoquinoline (manufactured by Alfa Aesar, China Ltd.), 1,3-dichloroisoquinoline (manufactured by Aalen Chemical Co. Ltd.) and 1,4-dichloroisoquinoline (manufactured by Bepharm Ltd) as a starting material.

Compound 1 to Compound 285 were prepared using the methods of Preparation Examples 1 to 11, and $^1$H NMR and MS/FAB of the prepared compounds are shown in Table 1.

TABLE 1

| Compound | $^1$H NMR (CDCl$_3$, 200 MHz) | MS/FAB Found | MS/FAB Calculated |
|---|---|---|---|
| 1 | δ = 8.42 (4H, d), 8.10 (4H, d) | 202.25 | 202.08 |
| 3 | δ = 8.42 (4H, d), 8.10 (4H, d), 2.34 (6H, s) | 230.30 | 230.11 |
| 5 | δ = 7.68 (4H, d), 7.54 (4H, t), 7.47 (2H, t), 7.21 (2H, d), 7.03 (2H, d), 6.92 (2H, t), 6.85 (2H, t) | 354.14 | 354.14 |
| 6 | δ = 8.55 (1H, d), 8.42 (5H, d), 8.10 (4H, d), 8.08 (1H, d), 8.04 (1H, d), 7.61 (1H, t), 7.55 (2H, d), 7.52 (2H, d), 7.51 (2H, t), 7.41 (1H, t) | 404.50 | 404.16 |
| 10 | δ = 8.93 (2H, d), 8.55 (1H, d), 8.42 (4H, d), 8.12 (2H, t), 8.10 (4H, d), 7.93 (1H, d), 7.88~7.82 (4H, m), 7.52 (2H, d), 7.51 (2H, t), 7.41 (1H, t) | 454.56 | 454.17 |
| 13 | δ = 8.55 (1H, d), 8.42 (4H, d), 8.12 (1H, d), 8.10 (4H, d), 7.94 (1H, d), 7.63~7.25 (10H, m) | 443.54 | 443.17 |
| 16 | δ = 8.42 (4H, d), 8.10 (4H, d), 7.70 (1H, s), 7.57 (1H, t), 7.52 (4H, d), 7.51 (4H, t), 7.48 (2H, d), 7.41 (2H, t) | 430.54 | 430.17 |
| 19 | δ = 8.42 (4H, d), 8.10 (4H, d), 8.00 (2H, d), 7.92 (1H, d), 7.73~7.48 (12H, m) 7.41 (1H, t) | 480.60 | 480.19 |

TABLE 1-continued

| Compound | ¹H NMR (CDCl₃, 200 MHz) | MS/FAB Found | MS/FAB Calculated |
|---|---|---|---|
| 21 | δ = 8.42 (4H, d), 8.10 (4H, d), 7.83 (1H, s), 7.52 (4H, d), 7.51 (4H, t), 7.41 (2H, t), 7.21 (2H, d), 6.58 (1H, d), 6.39 (1H, ds), 3.22 (1H, d), | 392.49 | 392.16 |
| 24 | δ = 8.42 (5H, d), 8.10 (4H, d), 7.96 (1H, t), 7.90 (1H, d), 7.80 (1H, d), 7.58 (1H, t), 7.52 (2H, d), 7.51 (2H, t), 7.41 (1H, t), 7.15 (2H, s) | 428.52 | 428.16 |
| 27 | δ = 8.55 (2H, d), 8.42 (4H, d), 8.10 (4H, d), 8.01 (2H, s), 7.55 (2H, d), 7.52 (2H, d), 7.51 (4H, t), 7.49 (2H, d), 7.41 (2H, t) | 480.60 | 480.19 |
| 30 | δ = 8.42 (4H, d), 8.10 (4H, d), 7.92 (2H, d), 7.73 (2H, d), 7.58 (2H, s), 7.52 (4H, d), 7.51 (4H, t), 7.41 (2H, t) | 480.60 | 480.19 |
| 32 | δ = 8.42 (4H, d), 8.10 (4H, d), 8.06 (1H, s), 7.87~7.53 (4H, m), 7.52 (4H, d), 7.51 (4H, t), 7.41 (2H, t), 7.38~7.28 (4H, s), 1.72 (6H, s) | 546.70 | 546.23 |
| 35 | δ = 8.55 (1H, d), 8.42 (4H, d), 8.10 (4H, d), 7.98~7.69 (4H, m), 7.58 (2H, t), 7.52 (6H, m), 7.45 (1H, t), 7.41 (1H, t), 7.33~7.25 (2H, d) | 519.63 | 519.20 |
| 41 | δ = 8.55 (2H, d), 8.42 (6H, d), 8.10 (4H, d), 8.06 (4H, d), 7.61 (2H, t), 7.55 (4H, d) | 454.56 | 454.17 |
| 45 | δ = 8.93 (2H, d), 8.55 (1H, d), 8.42 (5H, d), 8.12 (2H, d), 8.10 (4H, d), 8.06 (2H, d), 7.93 (1H, d), 7.85 (4H, d), 7.61 (1H, t), 7.55 (2H, d) | 504.62 | 504.19 |
| 47 | δ = 8.55 (2H, d), 8.42 (5H, d), 8.10 (4H, d), 8.06 (2H, d), 7.90 (2H, dd), 7.77~7.55 (6H, m), 7.38~7.28 (2H, m), 1.72 (6H, s) | 520.66 | 520.22 |
| 50 | δ = 8.55 (2H, d), 8.42 (5H, d), 8.10 (4H, d), 8.06 (2H, d), 7.61 (1H, t), 7.55 (2H, d), 7.52 (4H, dt), 7.41 (1H, t), 7.25 (4H, s) | 480.60 | 480.19 |
| 52 | δ = 8.55 (2H, d), 8.42 (6H, d), 8.10 (4H, d), 8.06 (4H, d), 7.61 (2H, t), 7.55 (4H, d), 7.25 (4H, s) | 530.66 | 530.20 |
| 57 | δ = 8.55 (1H, d), 8.42 (5H, d), 8.10 (4H, d), 8.06 (2H, d), 7.61 (1H, t), 7.55 (2H, d), 7.33 (1H, d), 7.26 (1H, d), 7.21 (2H, t), 6.94 (1H, s), 3.22 (1H, s) | 442.55 | 442.17 |
| 59 | δ = 8.55 (1H, d), 8.42 (5H, d), 8.10 (4H, d), 8.06 (2H, d), 7.96~7.79 (4H, m), 7.61 (1H, t), 7.58 (1H, t), 7.55 (2H, d), 7.15 (2H, s) | 478.58 | 478.17 |
| 66 | δ = 8.55 (1H, d), 8.42 (5H, d), 8.10 (4H, d), 8.06 (2H, d), 7.61 (1H, t), 7.58 (1H, t), 7.55 (2H, d), 7.25 (4H, s) | 596.76 | 596.25 |
| 69 | δ = 8.55 (1H, d), 8.42 (5H, d), 8.10 (4H, d), 8.08 (1H, d), 8.04 (1H, d), 7.87 (2H, d), 7.77 (2H, s), 7.69 (2H, d), 7.61 (1H, t), 7.55 (2H, d), 7.52 (2H, d), 7.51 (2H, t), 7.41 (1H, t) | 569.69 | 569.21 |
| 71 | δ = 8.55 (1H, d), 8.42 (5H, d), 8.18 (1H, d), 8.10 (4H, d), 8.08 (1H, d), 8.04 (1H, d), 8.00 (1H, d), 7.87 (1H, d), 7.77 (2H, s), 7.69 (1H, d), 7.58 (2H, t), 7.55 (2H, d), 7.52 (2H, d), 7.51 (2H, t), 7.50 (2H, d), 7.45 (2H, d), 7.41 (1H, d) | 645.79 | 645.25 |
| 76 | δ = 8.55 (1H, d), 8.42 (5H, d), 8.10 (4H, d), 8.08 (1H, d), 8.04 (1H, d), 7.61 (1H, d), 7.55 (2H, d), 7.54 (2H, d), 7.20 (4H, t), 6.81 (2H, d), 6.69 (2H, d), 6.63 (4H, d) | 571.71 | 571.23 |
| 79 | δ = 8.16 (4H, d), 7.67 (8H, d) | 302.37 | 302.11 |
| 82 | δ = 8.16 (4H, d), 7.67 (8H, d), 2.34 (2H, s) | 330.42 | 330.14 |
| 86 | δ = 8.31 (2H, s), 8.16 (4H, d), 7.91 (2H, d), 7.87 (1H, d), 7.67 (8H, d), 7.61 (1H, d), 7.52 (2H, d), 7.51 (2H, t), 7.45 (1H, t), 7.41 (1H, t), 7.39 (2H, d) | 554.68 | 554.20 |
| 87 | δ = 8.27 (1H, s), 8.16 (4H, d), 7.91 (4H, d), 7.67 (8H, d), 7.52 (2H, d), 7.51 (2H, t), 7.41 (1H, t), 7.39 (4H, d) | 554.68 | 554.20 |
| 90 | δ = 8.16 (4H, d), 7.93 (1H, d), 7.87 (1H, d), 7.77 (1H, s), 7.67 (8H, d), 7.63 (1H, d), 7.55 (1H, d), 7.52 (2H, d), 7.51 (2H, t), 7.41 (1H, t), 7.38 (1H, t), 7.28 (1H, t), 1.72 (2H, s) | 570.72 | 570.23 |

TABLE 1-continued

| Compound | ¹H NMR (CDCl₃, 200 MHz) | MS/FAB Found | MS/FAB Calculated |
|---|---|---|---|
| 93 | δ = 8.16 (4H, d), 8.00 (2H, d), 7.92 (1H, d), 7.73 (1H, d), 7.70 (1H, s), 7.67 (8H, d), 7.59 (2H, d), 7.58 (1H, s), 7.57 (1H. t), 7.52 (2H, d), 7.51 (2H, t), 7.48 (2H, d), 7.41 (1H, t) | 580.71 | 580.22 |
| 96 | δ = 8.16 (4H, d), 7.67 (8H, d), 7.52 (2H, d), 7.51 (2H, t), 7.41 (1H, t), 7.33 (1H, d), 7.26 (1H, d), 7.21 (2H, d), 6.94 (1H. s), 3.22 (1H, s) | 492.61 | 492.19 |
| 100 | δ = 8.16 (4H, d), 7.90 (2H, d), 7.79 (2H, d), 7.67 (8H, d), 7.63 (1H, d), 7.58 (2H, t), 7.52 (2H, d), 7.51 (2H, t), 7.48 (1H, s), 7.41 (1H, t), 7.19 (1H, d) | 578.70 | 578.20 |
| 105 | δ = 8.18 (1H, d), 8.16 (4H, d), 8.01 (1H, d), 7.67 (8H, d), 7.53 (2H, d), 7.52 (2H, d), 7.51 (2H, t), 7.41 (1H, t) | 511.63 | 511.24 |
| 107 | δ = 8.55 (2H, d), 8.42 (2H, d), 8.16 (4H, d), 8.08 (2H, d), 8.04 (2H, d), 7.67 (8H, d), 7.61 (2H, d), 7.55 (4H, d) | 554.68 | 554.20 |
| 110 | δ = 8.55 (1H, s), 8.42 (1H, d), 8.27 (1H, s), 8.16 (4H, d), 8.08 (1H, d), 8.04 (1H, d), 7.91 (4H, d), 7.67 (8H, d), 7.61 (1H, d), 7.55 (2H, d), 7.39 (4H, d) | 604.74 | 604.22 |
| 115 | δ = 8.55 (1H, s), 8.42 (1H, d), 8.16 (4H, d), 8.12 (1H, d), 8.08 (1H, d), 8.04 (1H, d), 7.87 (1H, d), 7.77 (1H, s), 7.69 (1H, d), 7.67 (8H, d), 7.63 (1H, d), 7.61 (1H, d), 7.55 (2H, d), 7.50 (1H, t), 7.29 (1H, t) | 593.71 | 593.21 |
| 116 | δ = 8.55 (1H, d), 8.42 (1H, d), 8.16 (4H, d), 8.08 (1H, d), 8.04 (1H, d), 8.00 (2H, d), 7.92 (1H, d), 7.73 (1H, d), 7.70 (1H, s), 7.67 (8H, d), 7.61 (1H, d), 7.59 (2H, d), 7.58 (1H, s), 7.57 (1H, t), 7.55 (2H, d), 7.48 (2H, d) | 630.77 | 630.23 |
| 119 | δ = 8.55 (1H, d), 8.42 (1H, d), 8.16 (4H, d), 8.08 (1H, d), 8.04 (1H, d), 7.67 (8H, d), 7.61 (1H, d), 7.55 (2H, d), 7.33 (1H, d), 7.26 (1H, d), 7.21 (2H, d), 6.94 (1H, s), 3.22 (1H, s) | 542.67 | 542.20 |
| 124 | δ = 8.55 (2H, d), 8.42 (1H, d), 8.16 (4H, d), 8.08 (1H, d), 8.04 (1H, d), 7.94 (1H, d), 7.87 (1H, d), 7.77 (1H, s), 7.69 (1H, d), 7.67 (8H, d), 7.61 (1H, d), 7.58 (2H, d), 7.55 (2H, t), 7.50 (2H, d), 7.45 (1H, t), 7.33 (1H, t), 7.25 (1H, t) | 669.81 | 669.25 |
| 126 | δ = 8.55 (1H, d), 8.42 (1H, d), 8.16 (4H, d), 8.08 (1H, d), 8.04 (1H, d), 7.67 (8H, d), 7.61 (1H, d), 7.55 (2H, d), 7.33 (1H, t), 7.26 (1H, t), 7.23 (1H, d), 7.01 (1H, d), 3.05 (1H, d) | 543.65 | 543.20 |
| 132 | δ = 8.54 (2H, d), 8.16 (4H, d), 7.81 (2H, d), 7.67 (4H, d), 7.52 (2H, d), 7.51 (2H, t), 7.41 (1H, t) | 378.46 | 378.14 |
| 136 | δ = 8.55 (1H, d), 8.54 (2H, d), 8.42 (1H, d), 8.16 (4H, d), 8.08 (1H, d), 8.04 (1H, d), 7.81 (2H, d), 7.67 (4H, d), 7.61 (1H, d), 7.55 (2H, d), 2.34 (1H, s) | 442.55 | 442.17 |
| 139 | δ = 8.54 (2H, d), 8.16 (4H, d), 8.00 (2H, d), 7.92 (1H, d), 7.81 (2H, d), 7.73 (1H, d), 7.67 (4H, d), 7.59 (2H, d), 7.58 (1H, s), 7.52 (2H, d), 7.51 (2H, t), 7.41 (1H, t) | 504.62 | 504.19 |
| 142 | δ = 8.93 (2H, d), 8.54 (2H, d), 8.16 (4H, d), 8.12 (1H, d), 7.93 (1H, s), 7.88 (2H, t), 7.82 (2H, dt), 7.81 (2H, d), 7.67 (4H, d), 7.52 (2H, d), 7.51 (2H, t), 7.41 (1H, t) | 554.68 | 554.20 |
| 147 | δ = 8.54 (2H, d), 8.16 (4H, d), 8.00 (2H, d), 7.92 (1H, d), 7.81 (2H, d), 7.73 (1H, d), 7.70 (1H, s), 7.67 (4H, d), 7.59 (3H, s), 7.57 (1H, t), 7.52 (2H, d), 7.51 (2H, t), 7.48 (2H, d), 7.41 (1H, t) | 580.71 | 580.22 |
| 150 | δ = 8.54 (2H, d), 8.16 (4H, d), 7.81 (2H, d), 7.67 (4H, d), 7.52 (2H, d), 7.51 (2H, t), 7.41 (1H, t), 7.33 (1H, d), 7.26 (1H, d), 7.21 (2H, d), 6.94 (1H, s), 3.22 (1H, s) | 492.61 | 492.19 |
| 152 | δ = 8.54 (2H, d), 8.16 (4H, d), 7.96 (1H, d), 7.90 (1H, d), 7.81 (2H, d), 7.80 (2H, d), | 528.64 | 582.19 |

TABLE 1-continued

| Compound | $^1$H NMR (CDCl$_3$, 200 MHz) | MS/FAB Found | MS/FAB Calculated |
|---|---|---|---|
| | 7.67 (4H, d), 7.58 (1H, d) 7.52 (2H, d), 7.51 (2H, t), 7.41 (1H, t), 7.15 (2H, s) | | |
| 158 | δ = 8.54 (2H, d), 8.16 (4H, d), 7.81 (2H, d), 7.74 (2H, d), 7.67 (4H, d), 7.52 (2H, d), 7.51 (2H, t), 7.41 (1H, t), 7.39 (2H, d) | 495.57 | 495.16 |
| 162 | δ = 8.55 (1H, d), 8.54 (2H, d), 8.42 (1H, d), 8.16 (4H, d), 8.06 (2H, d), 8.00 (2H, d), 7.92 (1H, d), 7.81 (2H, d), 7.73 (1H, d), 7.67 (4H, d), 7.61 (1H, t), 7.59 (2H, d), 7.58 (1H, d), 7.55 (2H, d) | 554.68 | 554.20 |
| 164 | δ = 8.55 (1H, d), 8.54 (2H, d), 8.42 (1H, d), 8.27 (1H, s), 8.16 (4H, d), 8.06 (2H, d), 7.91 (4H, d), 7.81 (2H, d), 7.67 (4H, d), 7.61 (1H, t), 7.55 (2H, d), 7.39 (4H, d) | 604.74 | 604.22 |
| 167 | δ = 8.55 (1H, d), 8.54 (2H, d), 8.42 (1H, d), 8.16 (4H, d), 8.06 (2H, d), 7.93 (1H, d), 7.87 (2H, d), 7.81 (2H, d), 7.77 (1H, s), 7.67 (4H, d), 7.63 (1H, d), 7.61 (1H, t), 7.55 (3H, d), 7.38 (1H, t), 7.28 (1H, t), 1.72 (6, s) | 593.71 | 593.21 |
| 171 | δ = 8.55 (1H, d), 8.54 (2H, d), 8.42 (1H, d), 8.16 (4H, d), 8.10 (1H, d), 8.06 (2H, d), 7.81 (2H, d), 7.67 (4H, d), 7.61 (1H, t), 7.55 (2H, d), 7.28 (2H, d), 6.58 (1H, d), 6.39 (1H, t), 3.22 (1H, d) | 542.67 | 542.20 |
| 176 | δ = 8.55 (1H, d), 8.54 (2H, d), 8.42 (3H, d), 8.16 (4H, d), 8.10 (2H, d), 8.06 (2H, d), 7.96 (1H, d), 7.90 (1H, d), 7.81 (3H, d), 7.67 (4H, d), 7.61 (1H, t), 7.58 (1H, d), 7.55 (2H, d) | 628.76 | 628.22 |
| 181 | δ = 8.55 (1H, d), 8.54 (2H, d), 8.42 (1H, d), 8.16 (4H, d), 8.06 (2H, d), 7.81 (2H, d), 7.74 (2H, d), 7.67 (4H, d), 7.61 (1H, t), 7.55 (2H, d), 7.39 (2H, d) | 545.63 | 545.18 |
| 183 | δ = 8.55 (1H, d), 8.54 (2H, d), 8.42 (1H, d), 8.16 (4H, d), 8.06 (2H, d), 7.81 (2H, d), 7.67 (4H, d), 7.61 (1H, t), 7.55 (2H, d), 7.54 (2H, d), 7.20 (4H, t), 6.81 (2H, t), 6.69 (2H, d), 6.63 (4H, d) | 671.83 | 671.26 |
| 189 | δ = 8.55 (1H, d), 8.54 (2H, d), 8.42 (1H, d), 8.16 (4H, d), 8.06 (2H, d), 7.81 (2H, d), 7.67 (4H, d), 7.61 (1H, t), 7.55 (2H, dt), 7.52 (2H, d), 7.51 (2H, d), 7.41 (1H, t) | 454.56 | 454.17 |
| 194 | δ = 8.54 (2H, d), 8.16 (4H, d), 7.98 (9H, s), 7.81 (2H, d), 7.67 (4H, d), 7.52 (2H, d), 7.51 (2H, d), 7.41 (1H, t), 4.82 (2H, s) | 580.71 | 580.22 |
| 196 | δ = 8.55 (1H, d), 8.54 (2H, d), 8.16 (4H, d), 8.12 (1H, d), 7.94 (1H, d), 7.81 (2H, d), 7.67 (4H, d), 7.63 (1H, d), 7.52 (2H, d), 7.51 (2H, d), 7.50 (1H, t), 7.41 (1H, t), 7.33 (1H, t), 7.29 (1H, d), 7.25 (1H, d) | 543.65 | 543.20 |
| 199 | δ = 8.54 (2H, d), 8.16 (4H, d), 7.81 (2H, d), 7.67 (4H, d), 7.52 (2H, d), 7.51 (2H, d), 7.41 (1H, t), 7.33 (1H, d), 7.26 (1H, d), 7.21 (2H, d), 6.94 (1H, s), 3.22 (1H, s) | 492.61 | 492.19 |
| 204 | δ = 8.54 (2H, d), 8.16 (4H, d), 7.81 (2H, d), 7.74 (2H, d), 7.67 (4H, d), 7.52 (2H, d), 7.51 (2H, t), 7.41 (1H, t), 7.39 (2H, d) | 445.51 | 445.15 |
| 206 | δ = 8.55 (1H, d), 8.54 (2H, d), 8.42 (1H, d), 8.16 (4H, d), 8.06 (2H, d), 8.00 (2H, d), 7.92 (1H, d), 7.81 (2H, d), 7.73 (1H, d), 7.67 (4H, d), 7.61 (1H, t), 7.59 (2H, d), 7.58 (1H, s), 7.55 (2H, d) | 554.68 | 554.20 |
| 213 | δ = 8.55 (1H, d), 8.54 (2H, d), 8.42 (1H, d), 8.16 (4H, d), 8.06 (2H, d), 7.81 (2H, d), 7.67 (4H, d), 7.61 (1H, t), 7.55 (2H, d), 7.33 (1H, t), 7.26 (1H, t), 7.23 (1H, d), 7.01 (1H, d), 3.05 (1H, s) | 543.65 | 543.20 |
| 217 | δ = 8.55 (1H, d), 8.54 (2H, d), 8.42 (3H, dd), 8.16 (4H, d), 8.10 (2H, d), 8.06 (2H, d), 7.96 (1H, d), 7.90 (1H, d), 7.81 (2H, d), 7.80 (1H, d), 7.79 (1H, d), 7.67 (4H, d), 7.61 (1H, t), 7.58 (1H, t), 7.55 (2H, d) | 628.76 | 628.22 |
| 220 | δ = 8.54 (1H, d), 8.16 (4H, d), 7.81 (1H, d), 7.67 (6H, ds), 7.52 (2H, d), 7.51 (2H, d), 7.41 (1H, t) | 378.46 | 378.14 |

TABLE 1-continued

| Compound | $^1$H NMR (CDCl$_3$, 200 MHz) | MS/FAB Found | MS/FAB Calculated |
|---|---|---|---|
| 222 | δ = δ = 8.54 (1H, d), 8.16 (4H, d), 7.81 (1H, d), 7.67 (6H, ds), 7.52 (4H, d), 7.51 (4H, d), 7.41 (2H, t) | 454.56 | 454.17 |
| 225 | δ = δ = 8.54 (1H, d), 8.31 (2H, s), 8.16 (4H, d), 7.91 (2H, d), 7.87 (1H, d), 7.81 (1H, d), 7.67 (6H, ds), 7.61 (1H, d), 7.52 (2H, d), 7.51 (1H, d), 7.45 (1H, t), 7.41 (1H, t), 7.39 (2H, d) | 554.68 | 554.20 |
| 230 | δ = 8.55 (1H, d), 8.54 (2H, s), 8.16 (4H, d), 8.12 (1H, d), 7.94 (1H, d), 7.81 (2H, d), 7.67 (4H, d), 7.63 (1H, d), 7.52 (2H, d), 7.51 (3H, m), 7.41 (1H, t), 7.33 (1H, t), 7.27 (2H, t) | 543.65 | 543.20 |
| 233 | δ = 8.54 (2H, s), 8.16 (4H, d), 7.81 (2H, d), 7.67 (4H, d), 7.52 (2H, d), 7.51 (2H, t), 7.41 (1H, t), 7.33 (1H, d), 7.26 (1H, d), 7.21 (2H, dd), 6.94 (1H, s), 3.22 (1H, s) | 492.61 | 492.19 |
| 238 | δ = 8.54 (1H, d), 8.16 (4H, d), 7.81 (1H, d), 7.74 (2H, d), 7.67 (6H, ds), 7.52 (2H, d), 7.51 (2H, d), 7.41 (1H, t), 7.39 (3H, dd) | 495.57 | 495.16 |
| 240 | δ = 8.54 (2H, d), 8.42 (1H, d), 8.16 (4H, d), 8.08 (1H, d), 8.04 (1H, d), 8.00 (2H, d), 7.92 (1H, d), 7.81 (1H, t), 7.73 (1H, d), 7.67 (6H, ds), 7.61 (1H, t), 7.59 (2H, d), 7.58 (1H, s), 7.55 (2H, d) | 554.68 | 554.20 |
| 244 | δ = 8.55 (1H, d), 8.54 (1H, d), 8.42 (3H, dd), 8.16 (2H, d), 8.10 (2H, d), 8.06 (2H, dd), 7.93 (1H, d), 7.87 (1H, d), 7.81 (1H, t), 7.77 (1H, s), 7.67 (2H, d), 7.63 (1H, d), 7.61 (1H, t), 7.55 (3H, dd), 7.38 (1H, d), 7.28 (1H, t), 1.91 (4H, d), 0.90 (6H, s) | 598.77 | 598.27 |
| 246 | δ = 8.55 (2H, dd), 8.54 (1H, d), 8.42 (3H, dd), 8.16 (2H, d), 8.10 (2H, d), 8.06 (2H, dd), 7.94 (1H, d), 7.87 (1H, d), 7.81 (1H, t), 7.77 (1H, s), 7.69 (1H, d), 7.67 (2H, d), 7.61 (1H, t), 7.58 (2H, t), 7.55 (2H, d), 7.50 (2H, d), 7.45 (1H, t), 7.33 (1H, t), 7.25 (1H, t) | 619.75 | 619.23 |
| 249 | δ = 8.55 (1H, d), 8.42 (3H, d), 8.16 (2H, d), 8.10 (2H, d), 8.06 (2H, d), 7.67 (4H, d), 7.61 (1H, t), 7.55 (2H, d), 7.26 (1H, d), 7.21 (2H, t), 7.18 (1H, d), 6.58 (1H, d), 6.39 (1H, d), 4.74 (1H, d) | 492.61 | 492.19 |
| 253 | δ = 7.57 (2H, s), 7.45 (2H, d), 7.23 (2H, d), 2.34 (6H, s) | 203.30 | 203.11 |
| 258 | δ = 8.93 (4H, d), 8.12 (4H, d), 7.93 (2H, s), 7.88 (4H, t), 7.82 (4H, t), 7.57 (2H, s), 7.45 (2H, d), 7.23 (2H, d), 2.34 (6H, s) | 582.73 | 582.23 |
| 260 | δ = 8.18 (2H, d), 8.12 (2H, d), 8.04 (2H, d), 7.88 (2H, d), 7.82 (2H, t), 7.71 (8H, s), 7.57 (2H, s), 7.45 (2H, d), 7.23 (2H, d), 2.34 (6H, s) | 630.77 | 630.23 |
| 265 | δ = 7.83 (2H, s), 7.57 (2H, s), 7.45 (2H, d), 7.24 (2H, d), 7.23 (2H, d), 7.21 (2H, d), 6.58 (2H, d), 6.39 (2H, t), 3.22 (2H, s), 2.34 (6H, s) | 458.59 | 458.20 |
| 269 | δ = 7.52 (4H, d), 7.51 (4H, t), 7.45 (4H, d), 7.41 (2H, t), 2.34 (12H, s) | 410.55 | 410.20 |
| 273 | δ = 8.93 (4H, d), 8.12 (4H, d), 7.93 (2H, s), 7.88 (4H, t), 7.82 (4H, t), 7.45 (4H, d), 2.34 (12H, s) | 610.78 | 610.27 |
| 277 | δ = 8.55 (2H, d), 8.12 (2H, d), 7.94 (2H, d), 7.63 (2H, d)0, 7.50 (2H, d), 7.45 (4H, d), 7.33 (2H, t), 7.29 (2H, t), 7.25 (2H, t), 2.34 (12H, s) | 588.74 | 588.26 |
| 281 | δ = 7.45 (4H, d), 7.26 (2H, d), 7.21 (4H, dd), 7.18 (2H, d), 6.58 (2H, t), 6.39 (2H, t), 4.74 (2H, d), 2.34 (12H, s) | 486.64 | 486.23 |
| 285 | δ = 8.93 (6H, ds), 8.12 (6H, ds), 7.88 (4H, t), 7.82 (4H, t), 7.52 (4H, d), 7.51 (4H, t), 7.41 (2H, t) | 654.79 | 654.23 |

As the verification of Compound 5 of the following Chemical Formula, the following data were verified.

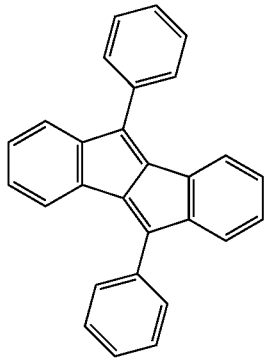 [SMILES: c1ccc(C2=C3C(=C(c4ccccc4)c4ccccc43)c3ccccc32)cc1]

UV: 261, 285 nm
PL: 365 nm
HOMO: −5.7 Ev
LUMO: −3.3 ev
Bg: 2.4 eV

EXPERIMENTAL EXAMPLE

Manufacture of OLED Device

A transparent ITO thin film obtained from an OLED glass (manufactured by Samsung Corning Co. Ltd.) was ultrasonic cleaned using trichloroethylene, acetone, ethanol and distilled water in consecutive order. An ITO substrate was placed on the substrate folder of a vacuum deposition apparatus, and was exhausted until the degree of vacuum within the chamber reaches $10^{-6}$ torr, and then a hole injection layer having a thickness of 200 Å was deposited on the ITO substrate by applying current to the cells within the vacuum deposition apparatus and thereby evaporating 2-TNATA. A hole transfer layer having a thickness of 600 Å was deposited on the hole injection layer by applying current to another cell and thereby evaporating the following N,N'-bis(α-naphthyl)-N,N'-diphenyl-4,4'-diamine (NPB). In one cell of the vacuum deposition apparatus, the compound prepared in the synthesis examples described in Table 2, or H1 was placed as a host material, and in another cell, the following dopant material D1 was placed and evaporated by applying current to the cell.

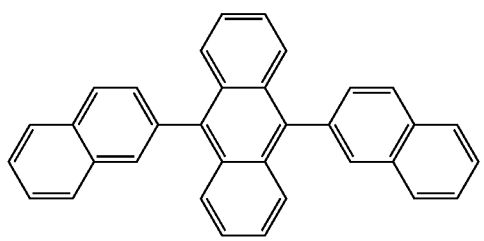
H1

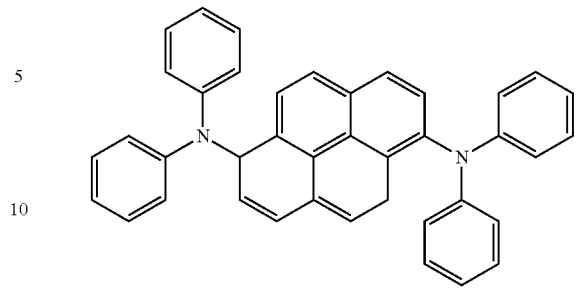
D1

Subsequently, a light emitting layer was deposited to a thickness of 400 Å on the hole transfer layer by heating and depositing the two cells together with the deposition rate ratio of the dopant to be 5% by weight (host:dopant=95:5). Next, the following tris(8-hydroxyquinoline)aluminum(III) (Alq) was deposited to thickness of 200 Å as an electron transfer layer. After that, the following lithium fluoride (LiF) compound was deposited to a thickness of 10 Å as an electron injection layer. Next, an OLED was manufactured by depositing Al cathode to a thickness of 1000 Å. Meanwhile, the OLED was manufactured by purifying each of all the organic compound materials necessary for the manufacture of the OLED device through vacuum sublimation purification under $10^{-6}$ to $10^{-8}$ torr.

TEST EXAMPLE

Evaluation of OLED Device Characteristics

The results of the current density and the life span of the OLED device manufactured in Experimental Examples 1 to 50 and Comparative Example 1, which were measured at 1000 cd/m² and 50% efficiency, are as shown in the following Table 2.

TABLE 2

| No | Compound No. | Cd/A @1000 cd/m² | Life Span (T50) |
|---|---|---|---|
|  | H1 | 4.5 | 250 |
| 1 | 1 | 4.7 | 450 |
| 2 | 3 | 4.6 | 440 |
| 3 | 5 | 4.5 | 410 |
| 4 | 6 | 4.8 | 460 |
| 5 | 10 | 5.1 | 500 |
| 6 | 13 | 5.1 | 400 |
| 7 | 16 | 4.6 | 410 |
| 8 | 19 | 4.8 | 450 |
| 9 | 21 | 4.8 | 460 |
| 10 | 24 | 4.6 | 430 |
| 11 | 27 | 4.6 | 430 |
| 12 | 30 | 4.5 | 410 |
| 13 | 32 | 4.8 | 450 |
| 14 | 35 | 4.9 | 400 |
| 15 | 41 | 4.9 | 470 |
| 16 | 45 | 4.7 | 450 |
| 17 | 47 | 4.9 | 430 |
| 18 | 50 | 4.6 | 440 |
| 19 | 52 | 4.8 | 450 |
| 20 | 57 | 4.9 | 460 |
| 21 | 59 | 4.8 | 440 |
| 22 | 66 | 5.0 | 400 |
| 23 | 69 | 4.9 | 410 |
| 24 | 71 | 5.1 | 410 |
| 25 | 76 | 5.0 | 400 |
| 26 | 79 | 4.8 | 460 |
| 27 | 82 | 4.8 | 450 |
| 28 | 86 | 4.9 | 470 |

TABLE 2-continued

| No | Compound No. | Cd/A @1000 cd/m$^2$ | Life Span (T50) |
| --- | --- | --- | --- |
| 29 | 87 | 4.9 | 490 |
| 30 | 90 | 5.1 | 430 |
| 31 | 93 | 5.0 | 450 |
| 32 | 96 | 4.7 | 440 |
| 33 | 100 | 4.7 | 430 |
| 34 | 105 | 4.7 | 400 |
| 35 | 107 | 4.8 | 460 |
| 36 | 110 | 4.7 | 440 |
| 37 | 115 | 4.7 | 400 |
| 38 | 116 | 4.9 | 450 |
| 39 | 119 | 4.8 | 440 |
| 40 | 124 | 5.0 | 390 |
| 41 | 126 | 4.9 | 400 |
| 42 | 132 | 4.7 | 450 |
| 43 | 136 | 4.8 | 430 |
| 44 | 139 | 4.9 | 460 |
| 45 | 142 | 4.8 | 460 |
| 46 | 147 | 4.6 | 430 |
| 47 | 150 | 4.9 | 460 |
| 48 | 152 | 4.8 | 450 |
| 49 | 158 | 4.9 | 400 |
| 50 | 162 | 4.7 | 460 |

REFERENCE

100 Substrate
200 Anode
300 Organic Material Layer
301 Hole Injection Layer
302 Hole Transfer Layer
303 Light Emitting Layer
304 Electron Transfer Layer
305 Electron Injection Layer
400 Cathode

What is claimed is:

1. A compound of the following Chemical Formula 1:

[Chemical Formula 1]

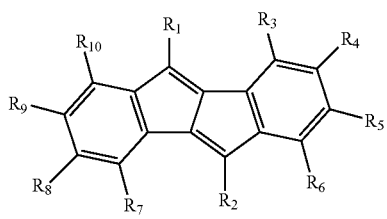

wherein, in Chemical Formula 1,
$R_1$ and $R_2$ are different from each other,
$R_1$ and $R_2$ are each independently anthracenyl; phenanthrenyl; pyrenyl; triphenylenyl; phenyl-or alkyl-substituted fluorenyl; phenyl-substituted or unsubstituted carbazolyl; naphthyl, arylamine or dimethylfluorenyl-substituted or unsubstituted phenyl; biphenyl; alkyl-substituted or unsubstituted indenyl; acenaphthylenyl; fluoranthenyl; phenyl-substituted naphthyl; indolyl; benzoxazolyl; or benzothiazolyl,
at least one of $R_1$ or $R_2$ is a substituent having seven or more carbons in ring members, or a substituent including two or more rings,
$R_3$ to $R_{10}$ are each independently hydrogen or a monovalent organic substituent; and
$R_3$ and $R_4$, $R_4$ and $R_5$, $R_5$ and $R_6$, $R_7$ and $R_8$, $R_8$ and $R_9$ or $R_9$ and $R_{10}$ may form a monocyclic or multicyclic aliphatic ring, or a monocyclic or multicyclic aromatic ring, by being linked through $C_3$-$C_{30}$ alkylene or $C_3$-$C_{30}$ alkenylene that does or does not include a fused ring.

2. The compound of claim 1, wherein $R_3$ to $R_{10}$ are each independently
hydrogen,
halogen,
substituted or unsubstituted $C_1$-$C_{30}$ alkyl,
substituted or unsubstituted $C_6$-$C_{30}$ aryl,
substituted or unsubstituted $C_6$-$C_{30}$ aryl in which one or more of substituted or unsubstituted $C_3$-$C_{30}$ cycloalkyl, substituted or unsubstituted $C_3$-$C_{30}$ heteroaryl and substituted or unsubstituted 5-membered to 7-membered heterocycloalkyl are fused,
substituted or unsubstituted $C_3$-$C_{30}$ heteroaryl,
substituted or unsubstituted $C_3$-$C_{30}$ heteroaryl in which one or more of substituted or unsubstituted $C_3$-$C_{30}$ cycloalkyl, a substituted or unsubstituted $C_6$-$C_{30}$ aromatic ring and substituted or unsubstituted 5-membered to 7-membered heterocycloalkyl are fused,
substituted or unsubstituted 5-membered to 7-membered heterocycloalkyl,
substituted or unsubstituted 5-membered to 7-membered heterocycloalkyl in which one or more of substituted or unsubstituted $C_3$-$C_{30}$ heterocycloalkyl, a substituted or unsubstituted $C_6$-$C_{30}$ aromatic ring and substituted or unsubstituted $C_3$-$C_{30}$ heteroaryl are fused,
substituted or unsubstituted $C_3$-$C_{30}$ cycloalkyl,
substituted or unsubstituted $C_3$-$C_{30}$ cycloalkyl in which one or more of substituted or unsubstituted $C_3$-$C_{30}$ heterocycloalkyl, a substituted or unsubstituted $C_6$-$C_{30}$ aromatic ring and substituted or unsubstituted $C_3$-$C_{30}$ heteroaryl are fused,
cyano,
—$NR_{11}R_{12}$,
—$SiR_{13}R_{14}R_{15}$,
—$OR_{16}$,
—$SR_{17}$,
substituted or unsubstituted ($C_6$-$C_{30}$)ar($C_1$-$C_{30}$)alkyl,
substituted or unsubstituted $C_1$-$C_{30}$ alkylamino, $C_3$-$C_{30}$ heteroaryl in which —$SiR_{18}R_{19}R_{20}$ is substituted,
substituted or unsubstituted $C_6$-$C_{30}$ arylamino,
substituted or unsubstituted $C_2$-$C_{30}$ alkenyl,
substituted or unsubstituted $C_2$-$C_{30}$ alkynyl,
carboxyl,
nitro or
hydroxy,
or form a monocyclic or multicyclic aliphatic ring, or a monocyclic or multicyclic aromatic ring, by being linked to an adjacent substituent through $C_3$-$C_{30}$ alkylene or $C_3$-$C_{30}$ alkenylene that does or does not include a fused ring,
$R_{11}$ to $R_{20}$ are each independently hydrogen; substituted or unsubstituted $C_1$-$C_{30}$ alkyl; substituted or unsubstituted $C_6$-$C_{30}$ aryl; or substituted or unsubstituted $C_3$-$C_{30}$ heteroaryl.

3. The compound of claim 2, wherein, in "substituted or unsubstituted" of $R_1$ to $R_{10}$, substituted means being each independently further substituted with one or more selected from the group consisting of deuterium, halogen, $C_1$-$C_{30}$ alkyl in which halogen is substituted or unsubstituted, $C_6$-$C_{30}$ aryl, $C_3$-$C_{30}$ heteroaryl in which $C_6$-$C_{30}$ aryl is substituted or unsubstituted, 5-membered to 7-membered heterocycloalkyl, 5-membered to 7-membered heterocycloalkyl in which one or more aromatic rings are fused, $C_3$-$C_{30}$ cycloalkyl, $C_3$-$C_{30}$ cycloalkyl in which one or more aromatic rings are fused, tri($C_1$-$C_{30}$)alkylsilyl, di($C_1$-$C_{30}$) alkyl($C_6$-$C_{30}$)arylsilyl, tri($C_6$-$C_{30}$)arylsilyl, $C_2$-$C_{30}$ alkenyl, $C_2$-$C_{30}$ alkynyl, cyano, carbazolyl, —$NR_{31}R_{32}$, —$SiR_{33}R_{34}R_{35}$, —$OR_{36}$, —$SR_{37}$, ($C_6$-$C_{30}$)ar($C_1$-$C_{30}$)alkyl, ($C_1$-$C_{30}$)alkyl($C_6$-$C_{30}$)aryl, $C_1$-$C_{30}$ alkyloxy, $C_1$-$C_{30}$ alkylthio, $C_6$-$C_{30}$ aryloxy, $C_6$-$C_{30}$ arylthio, carboxyl, nitro or hydroxy, and $R_{31}$ to $R_{37}$ are each independently hydrogen, $C_1$-$C_{30}$ alkyl, $C_6$-$C_{30}$ aryl or $C_3$-$C_{30}$ heteroaryl, or form a monocyclic or multicyclic aliphatic ring, or a monocyclic or multicyclic aromatic ring, by being linked to an adjacent substituent through $C_3$-$C_{30}$ alkylene or $C_3$-$C_{30}$ alkenylene that does or does not include a fused ring.

4. The compound of claim 1, wherein $R_3$ to $R_{10}$ are each independently selected from the group consisting of
hydrogen,
halogen,
methyl,
ethyl,
propyl,
butyl,
pentyl,
hexyl,
ethylhexyl,
heptyl,
octyl,
phenyl,
naphthyl,
fluorenyl,
biphenyl,
phenanthryl,
terphenyl,
pyrenyl,
furylenyl,
spirobifluorenyl,
fluoranthenyl,
crycenyl,
triphenylenyl,
1,2-dihydroacenaphthyl,
dibenzothiophenyl,
dibenzofuryl,
carbazolyl,
pyridyl,
furyl,
thienyl,
quinolyl,
triazinyl,
pyrimidinyl,
pyridazinyl,
quinoxalinyl,
phenanthrolinyl,
benzopyrolidino,
benzopiperidino,
dibenzomorpholino,
dibenzoazepino,
amino substituted by phenyl, naphthyl, fluorenyl, biphenyl, phenanthryl, terphenyl, pyrenyl, furylenyl, spirobifluorenyl, fluoranthenyl, crycenyl, triphenylenyl, dibenzothiophenyl, dibenzofuryl, carbazolyl, pyridyl, furyl, thienyl, quinolyl, triazinyl, pyrimidinyl, pyridazinyl, quinoxalinyl or phenanthrolinyl,
biphenyloxy,
biphenylthio,
biphenylmethyl,
triphenylmethyl,
carboxyl,
nitro and
hydroxy.

5. The compound of claim 1, wherein Chemical Formula 1 is represented by any one of Chemical Formulae 2 to 9:

[Chemical Formula 2]

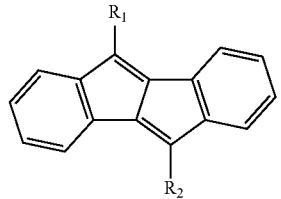

[Chemical Formula 3]

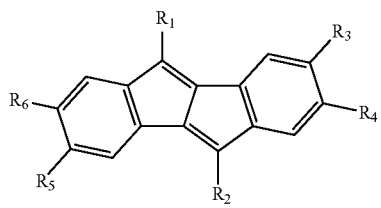

[Chemical Formula 4]

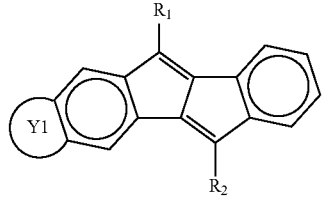

[Chemical Formula 5]

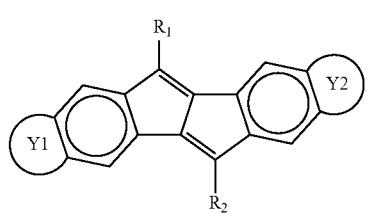

[Chemical Formula 6]

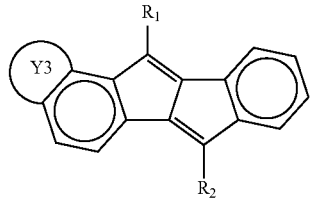

[Chemical Formula 7]

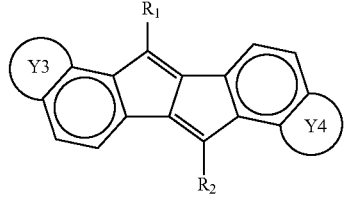

[Chemical Formula 8]

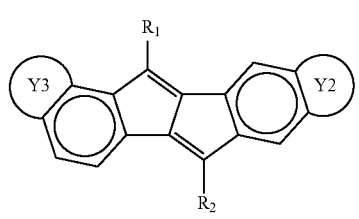

[Chemical Formula 9]

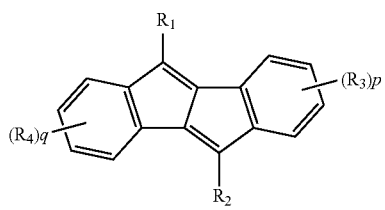

wherein, in Chemical Formulae 2 to 9, $R_1$, $R_2$, $R_3$ and $R_4$ are the same as those defined in claim 1, p and q each independently represent an integer of 1 to 4, Y1 to Y4 represent one of substituted or unsubstituted $C_3$-$C_{30}$ cycloalkyl, substituted or unsubstituted $C_3$-$C_{30}$ heteroaryl, substituted or unsubstituted 5-membered to 7-membered heterocycloalkyl and substituted or unsubstituted $C_6$-$C_{30}$ aryl, or a ring in which two or more of these rings are fused.

6. The compound of claim 1 selected from the group consisting of the following structural formulae:

6

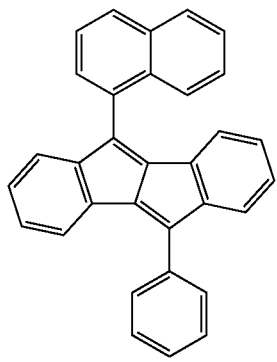

7

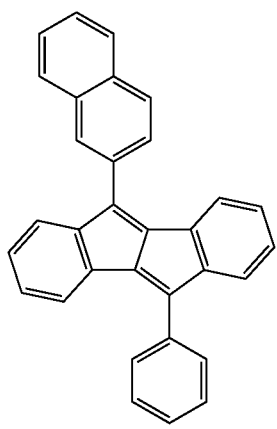

8

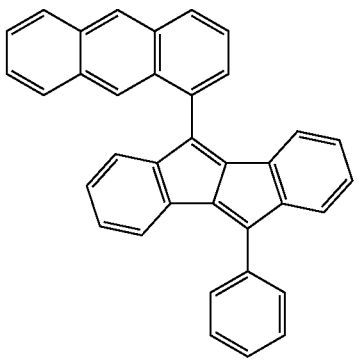

9

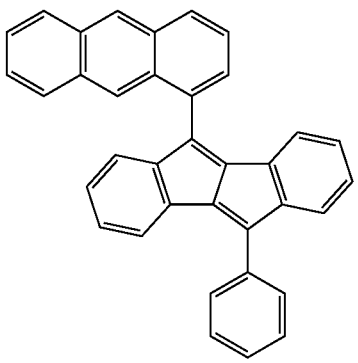

10

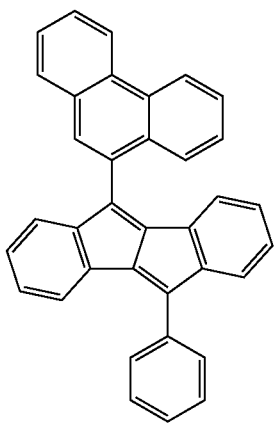

11

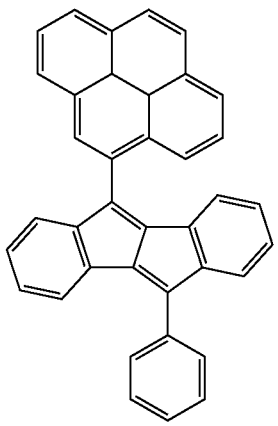

137
-continued
12
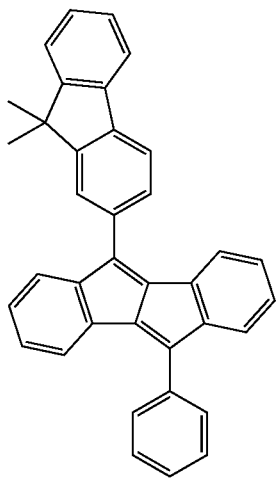
13
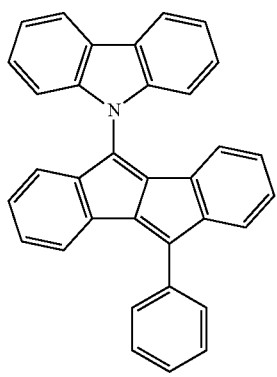
14
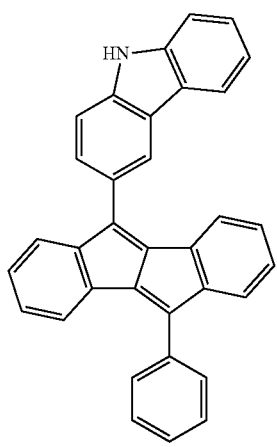
138
-continued
15
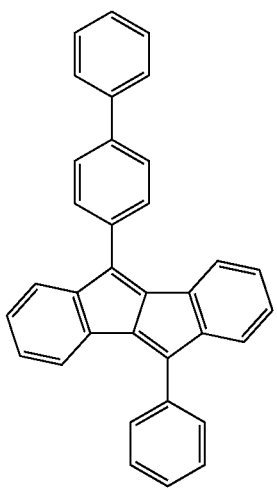
16
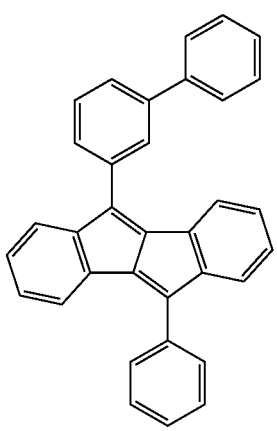
17
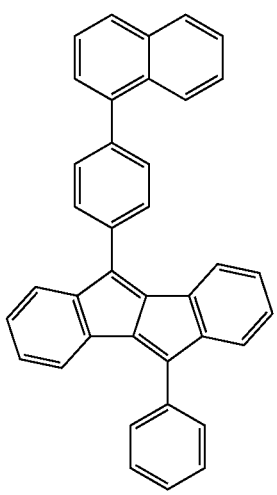

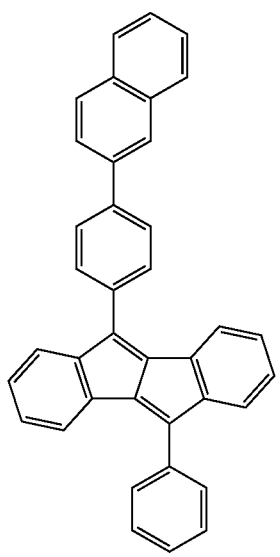
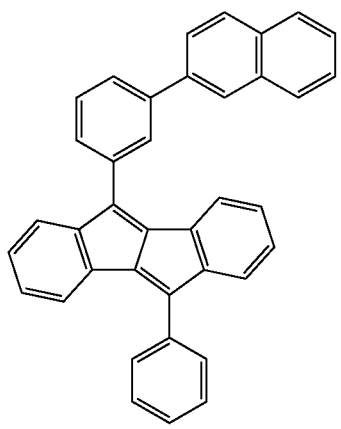
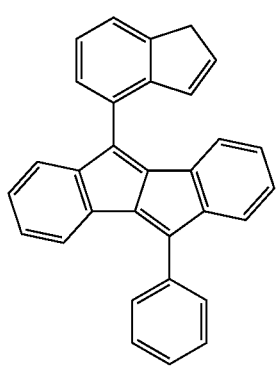
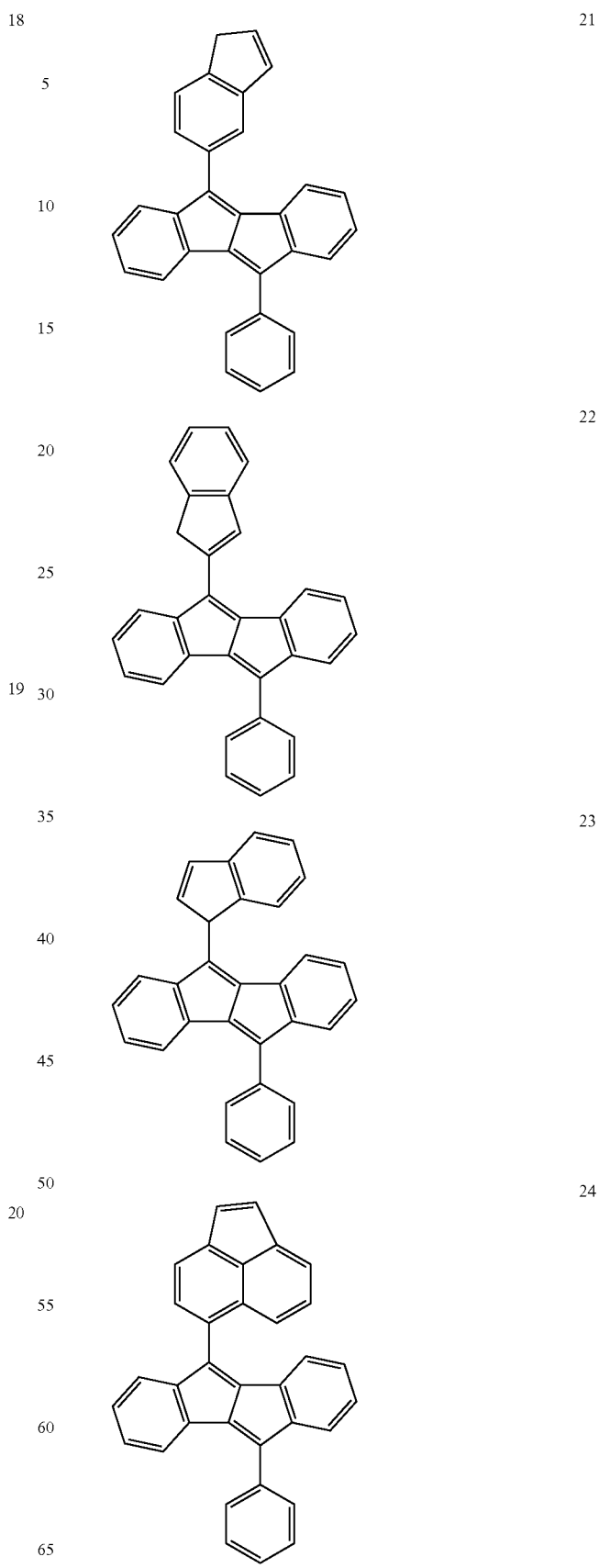

-continued
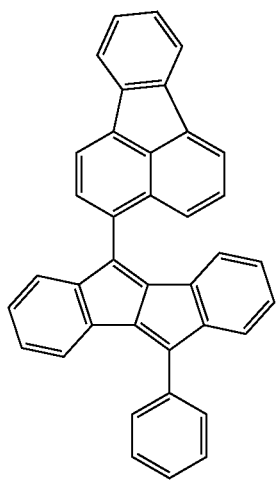
-continued
25
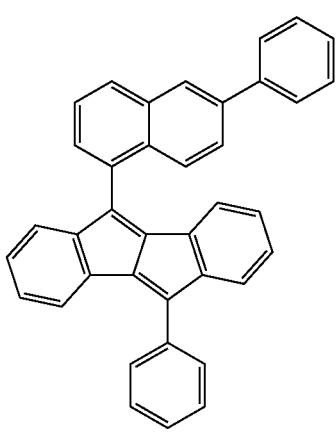
26
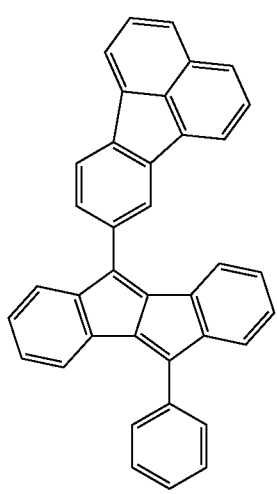
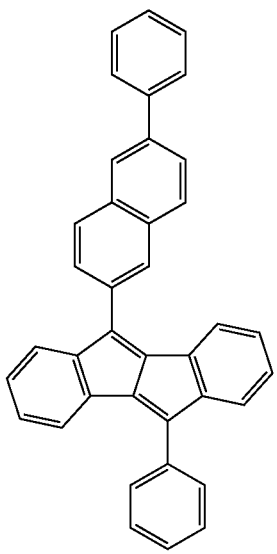
27
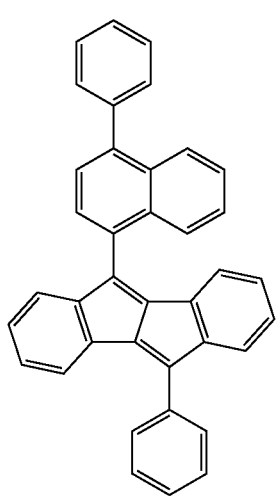
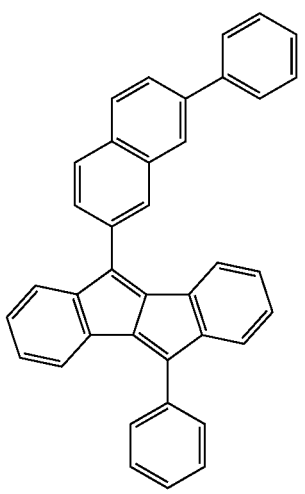
28
29
30

31
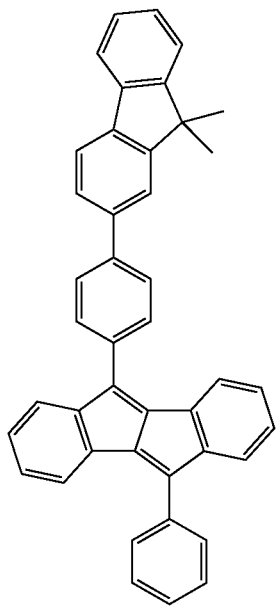
32
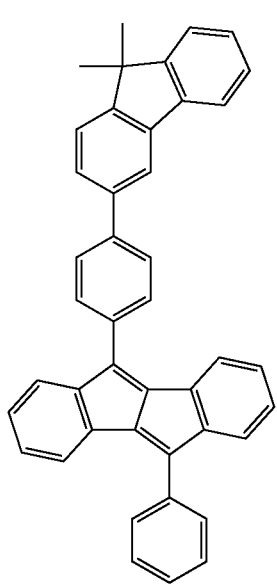
33
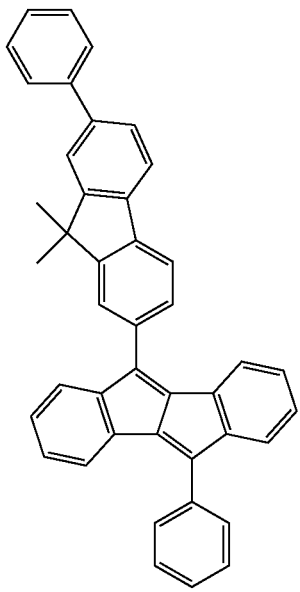
34
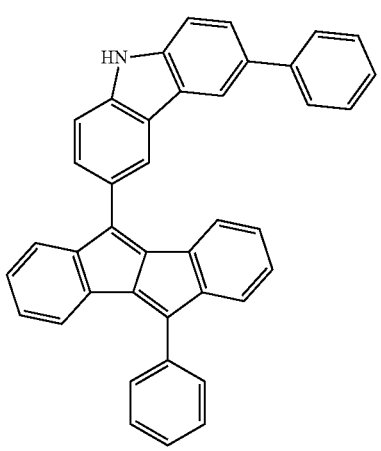
35

145
-continued
36
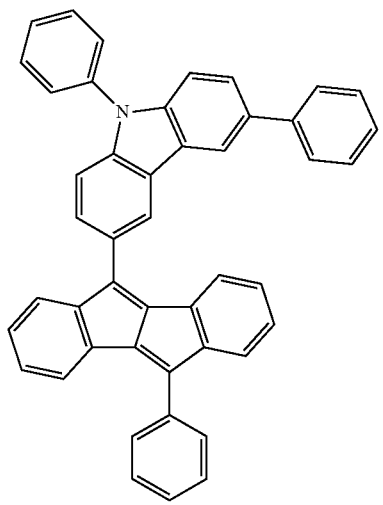
37
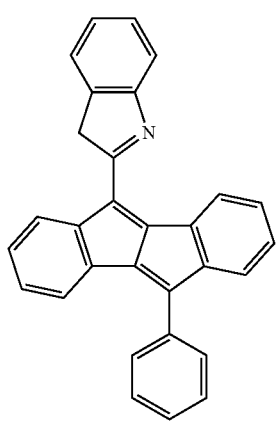
38
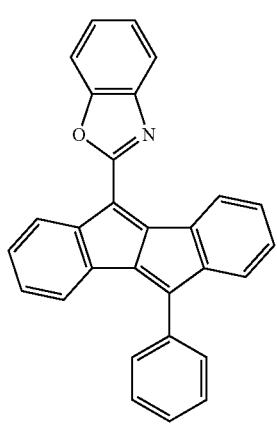
146
-continued
39
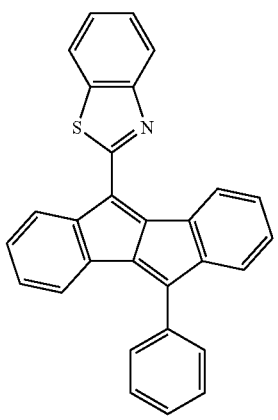
40
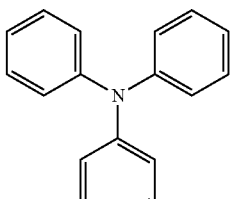
43
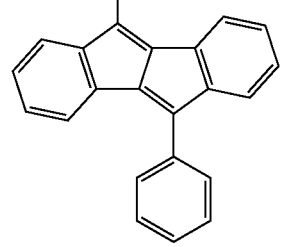
44
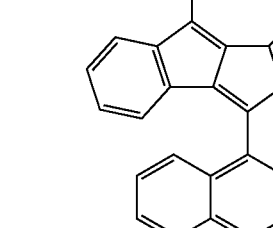

45
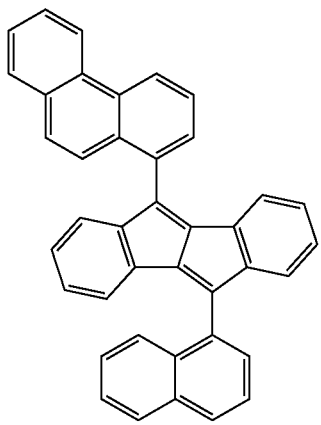
46
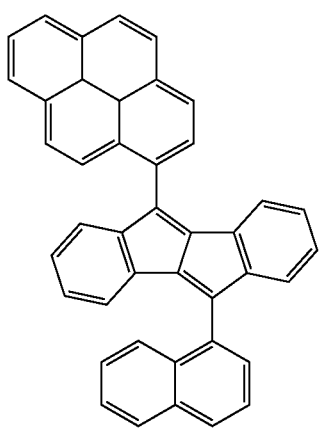
47
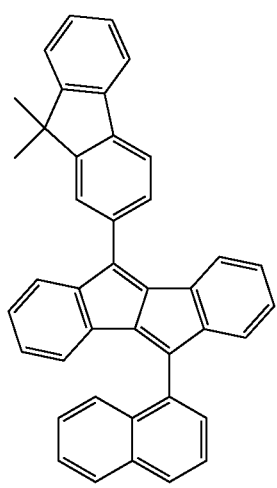
48
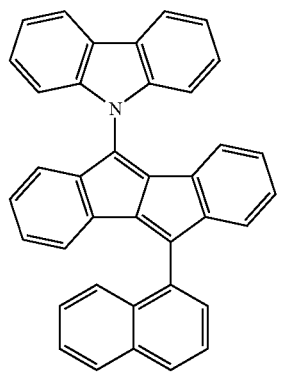
49
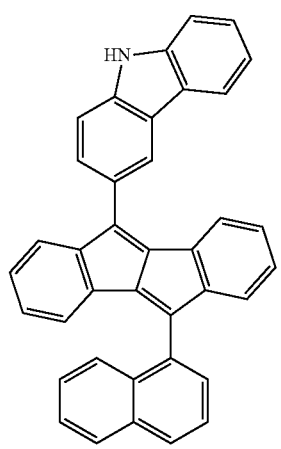
50
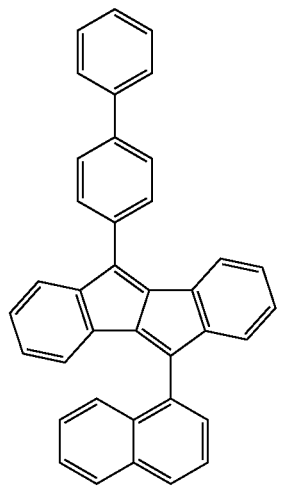

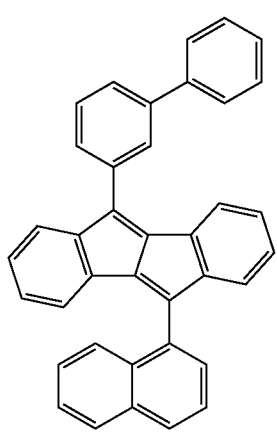
51
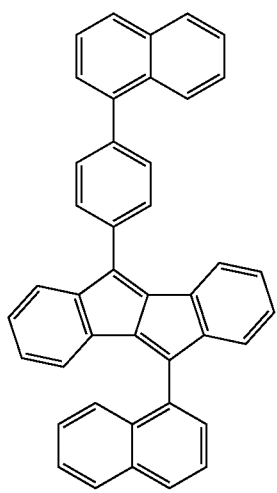
52
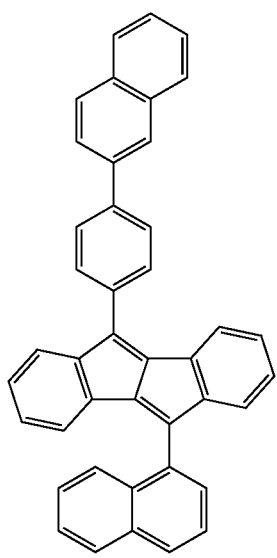
53
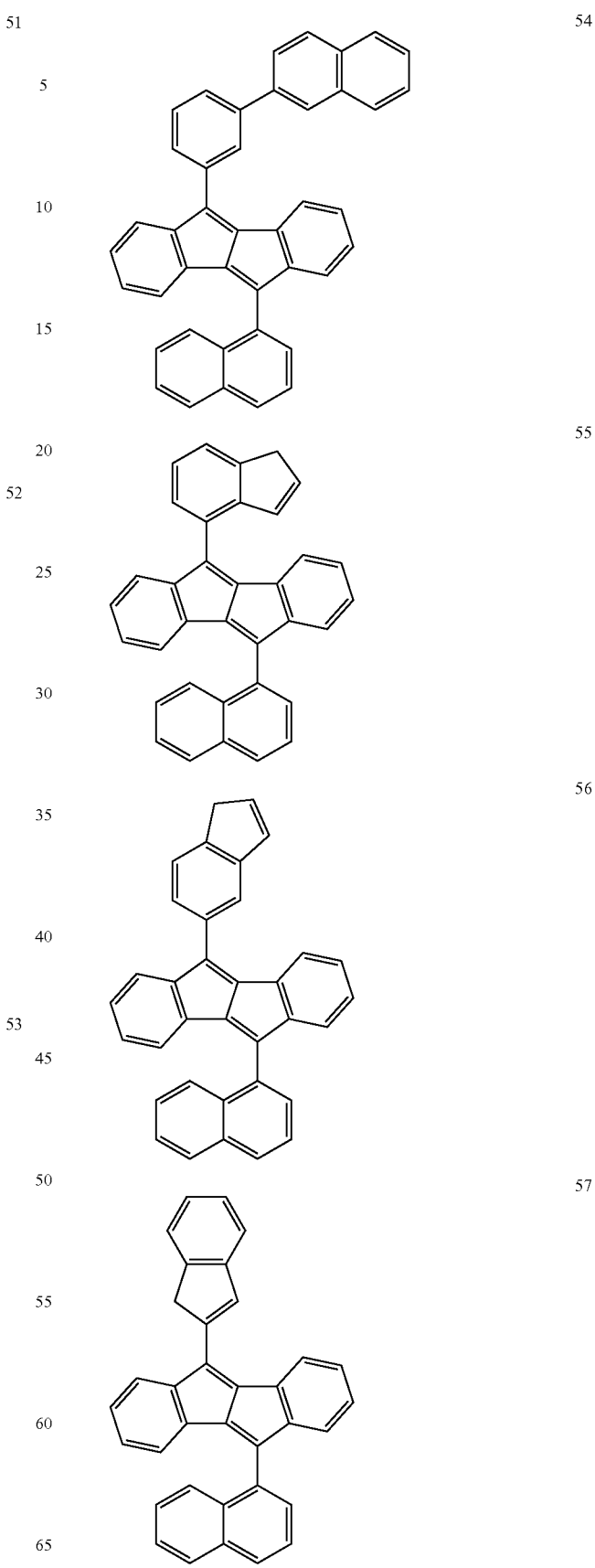

58
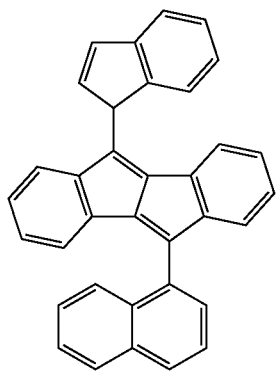
59
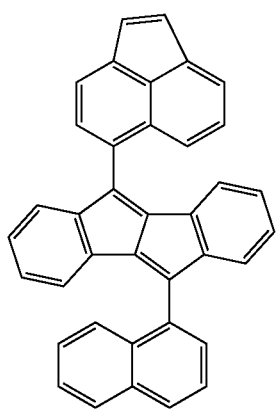
60
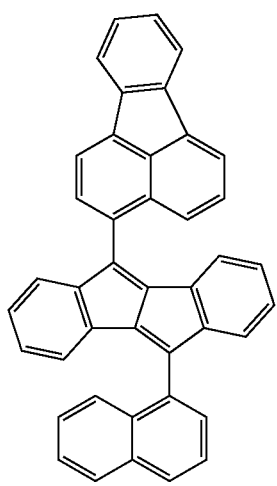
61
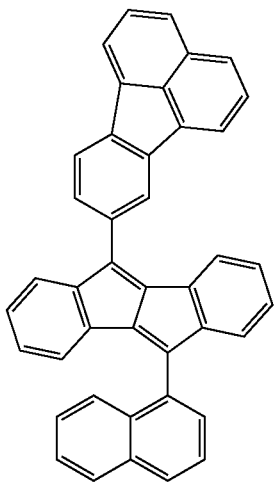
62
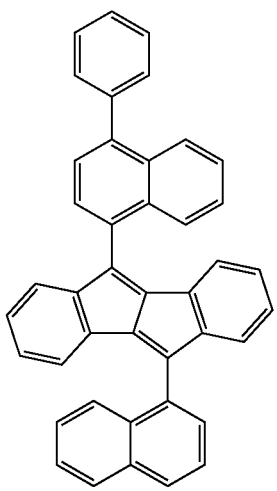
63
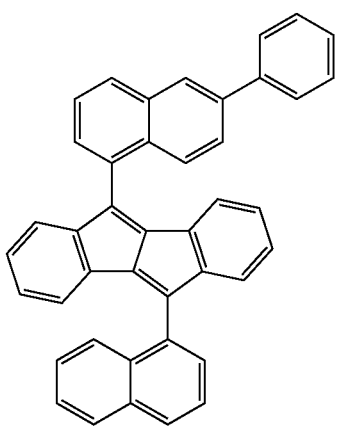

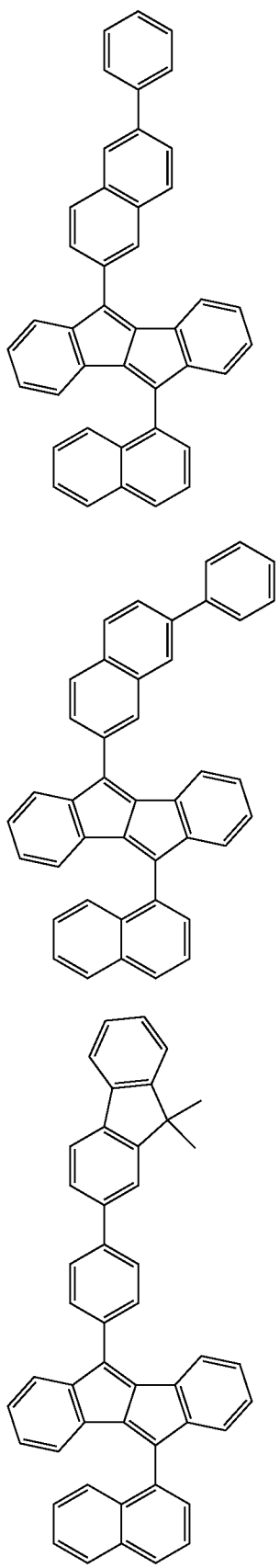
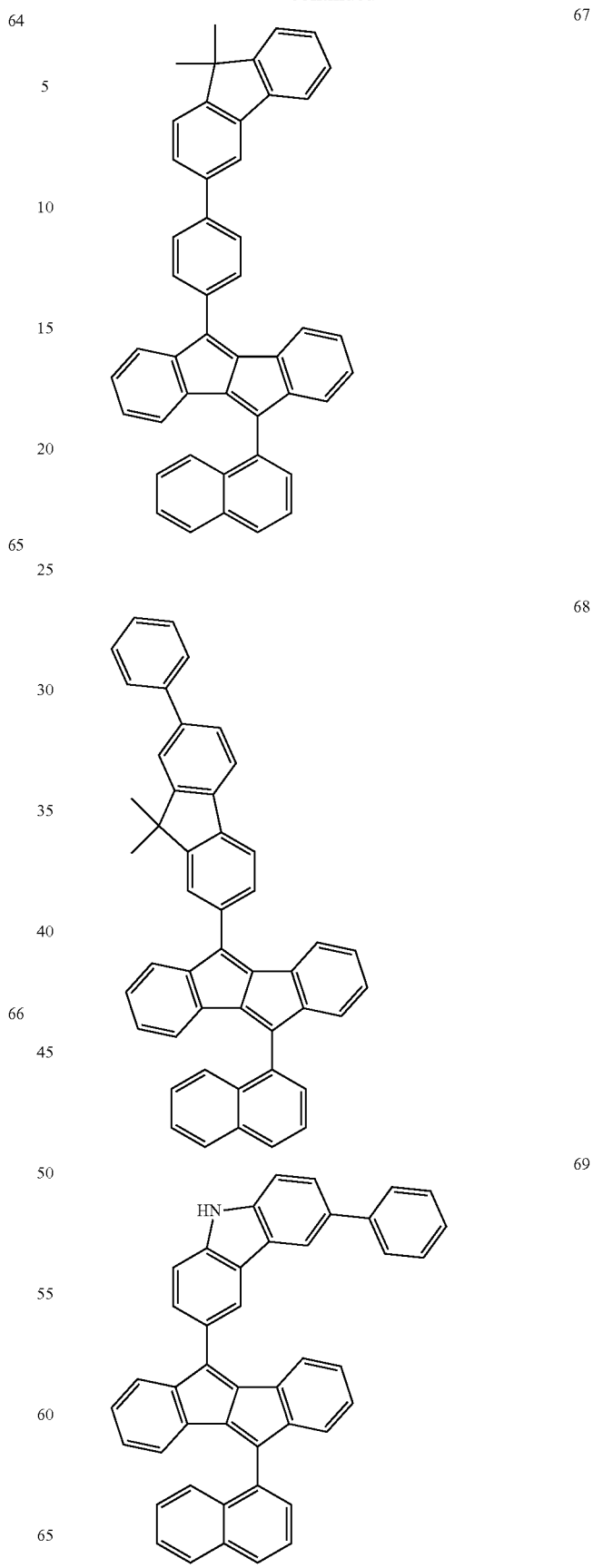

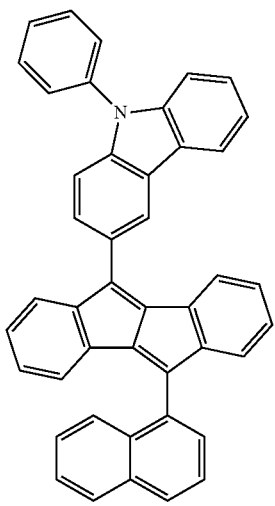
70
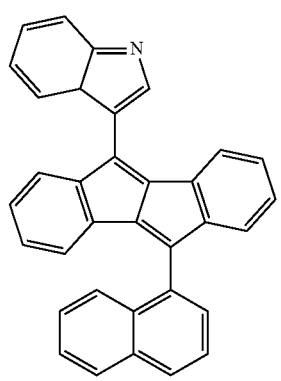
73
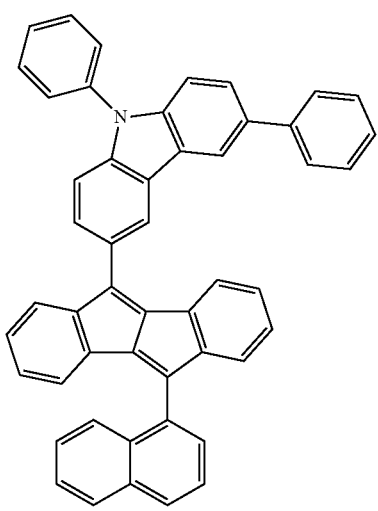
71
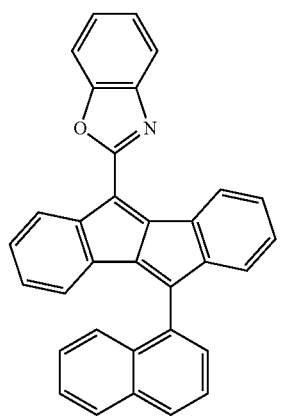
74
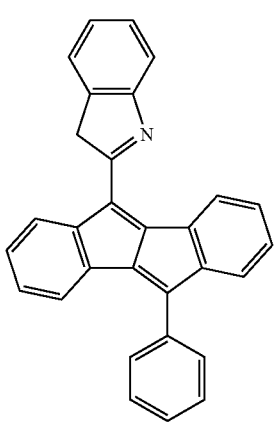
72
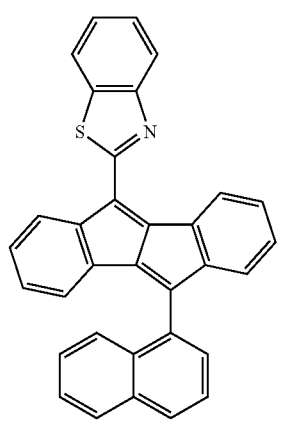
75

-continued
76
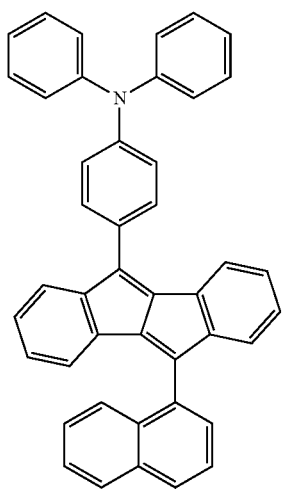
77
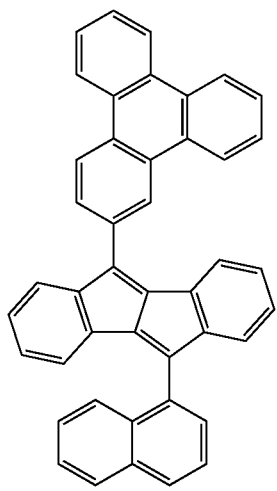
78
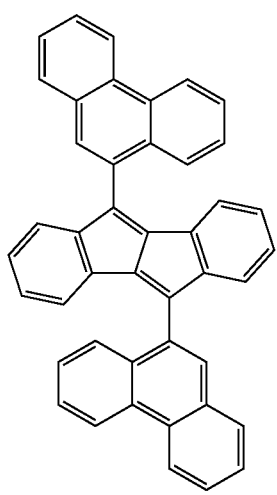
-continued
84
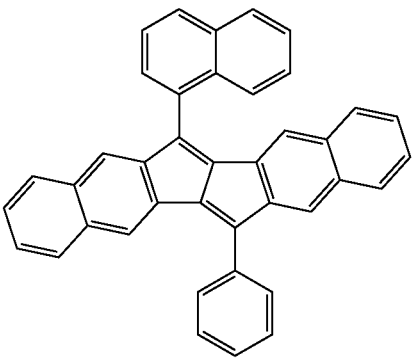
85
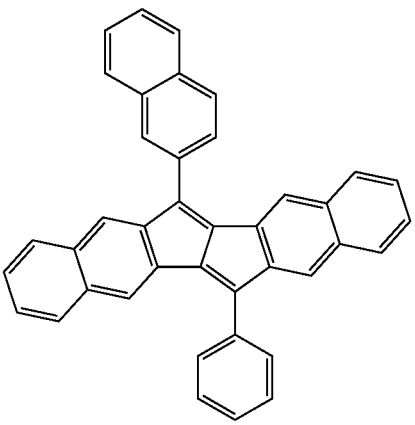
86
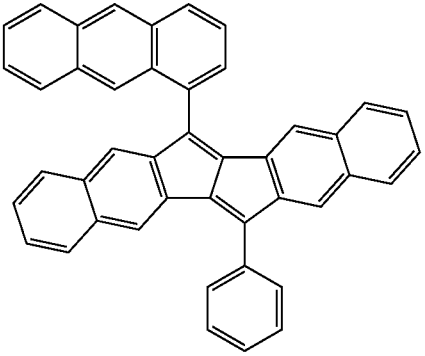
87
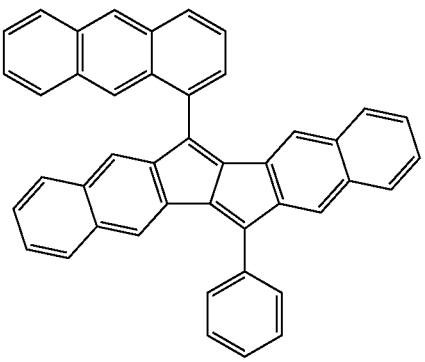

159
-continued
88
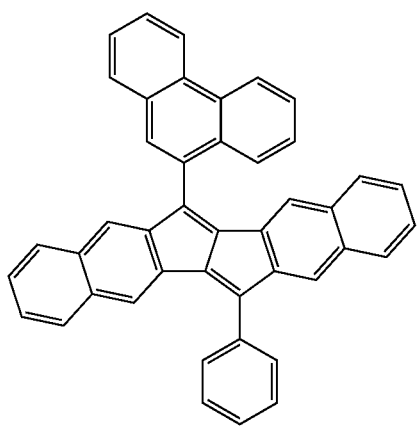
89
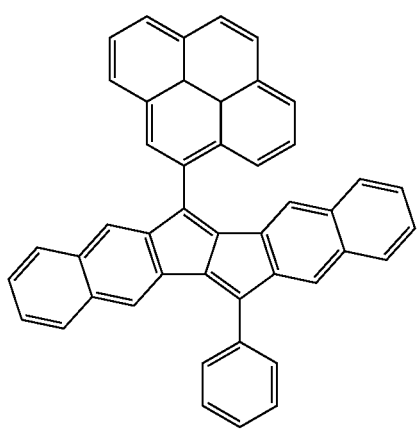
90
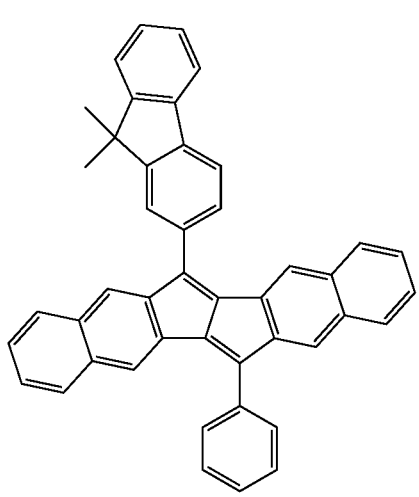
160
-continued
91
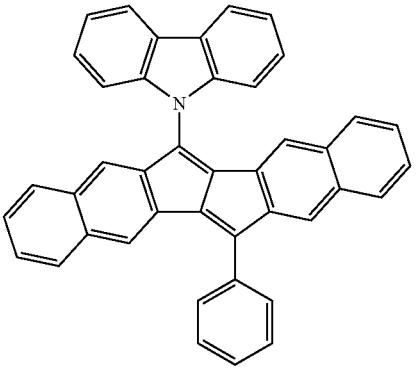
92
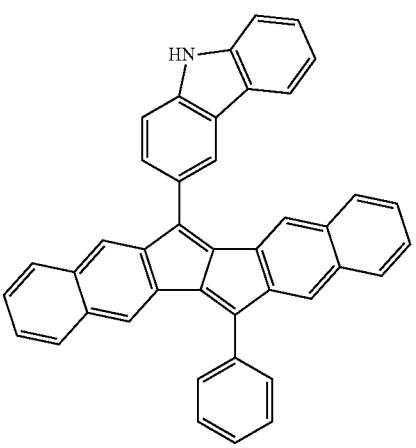
93
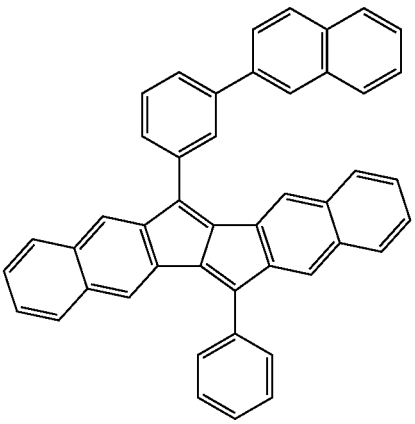
94
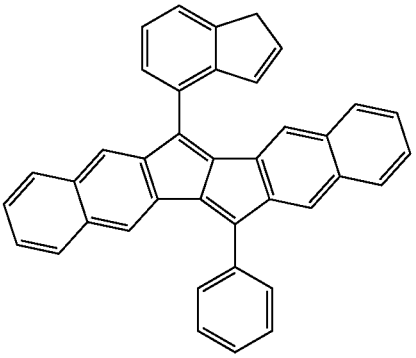

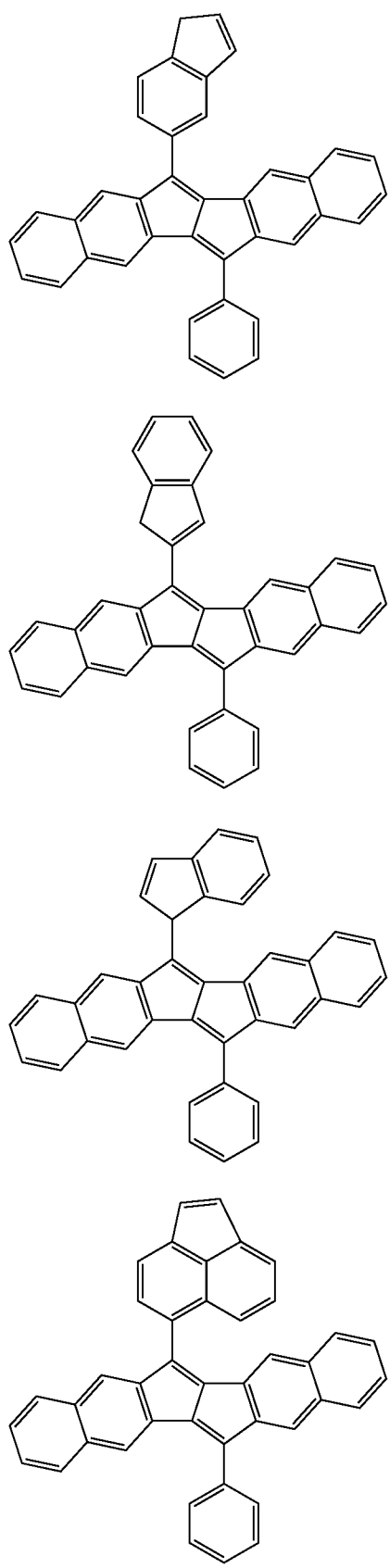
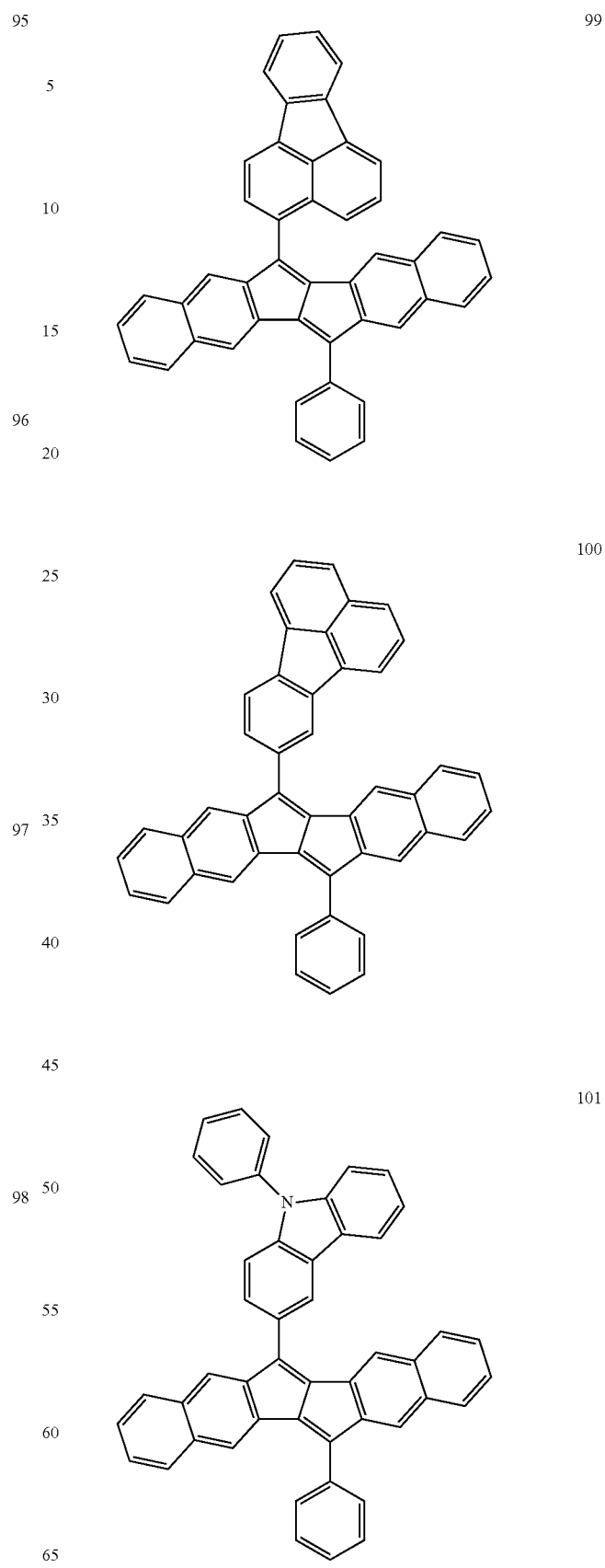

102 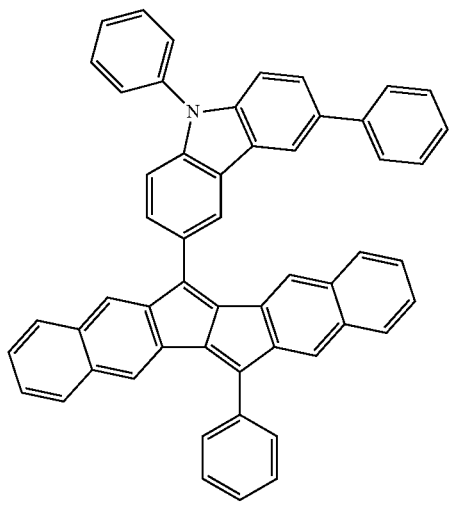
103 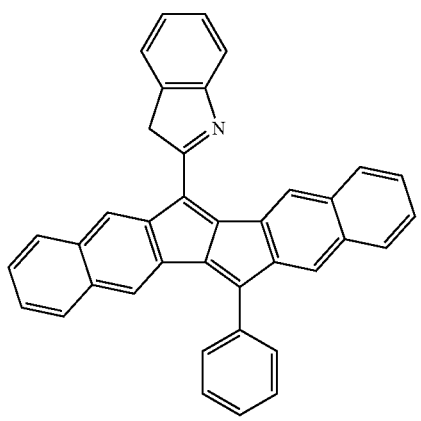
104 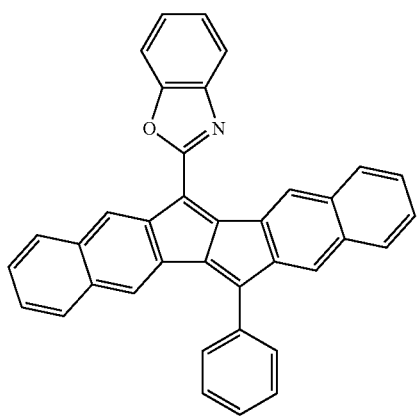
105 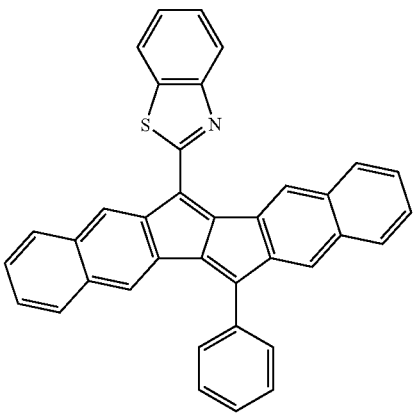
106 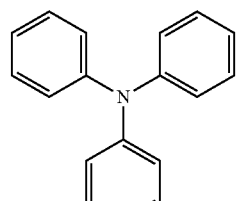 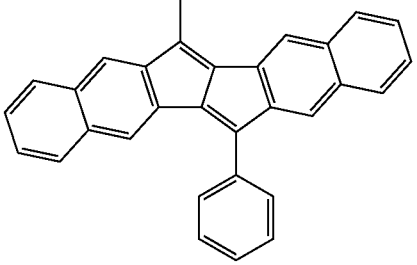
109 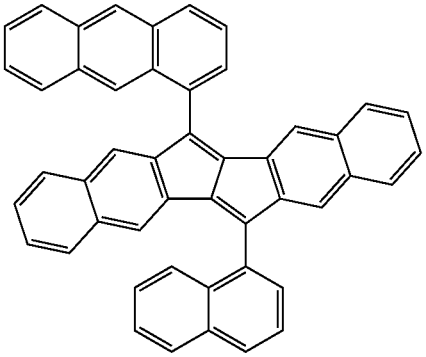
110 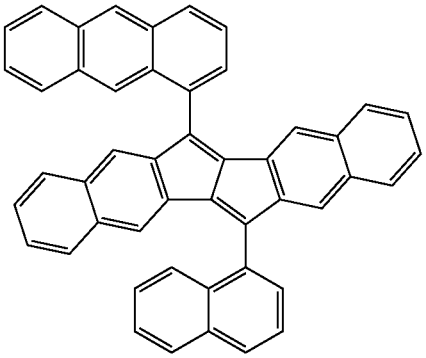

111 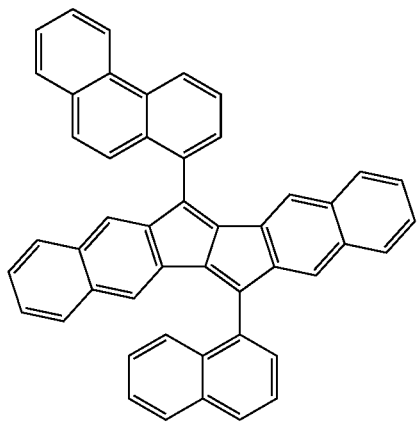
112 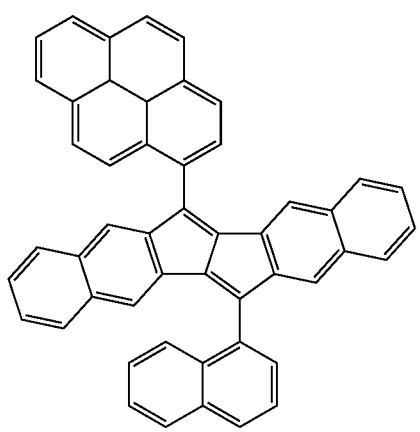
113 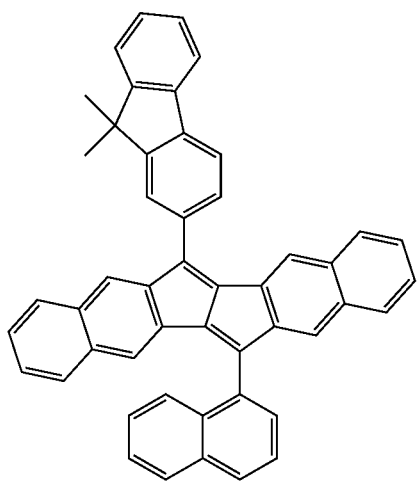
114 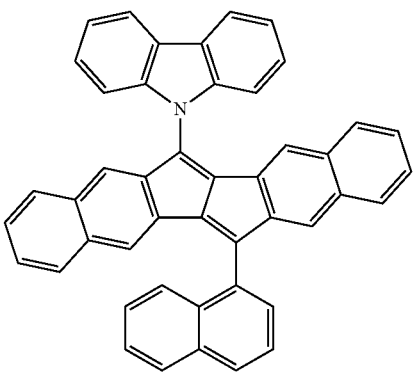
115 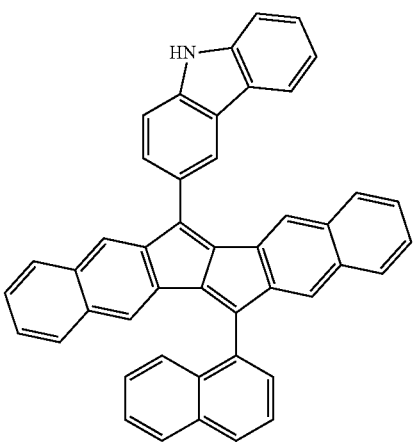
116 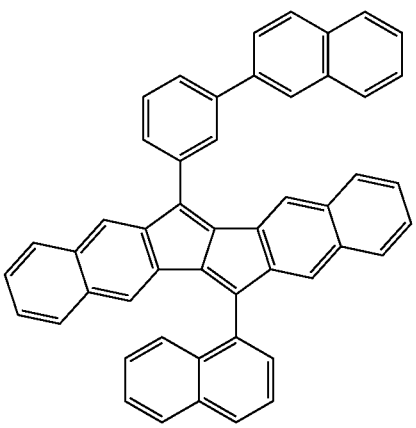
117 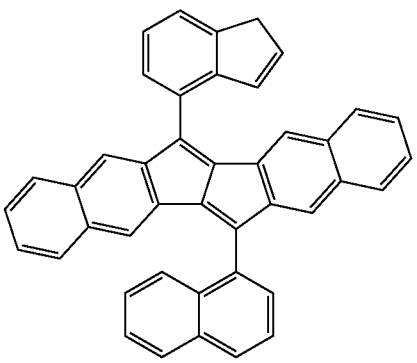

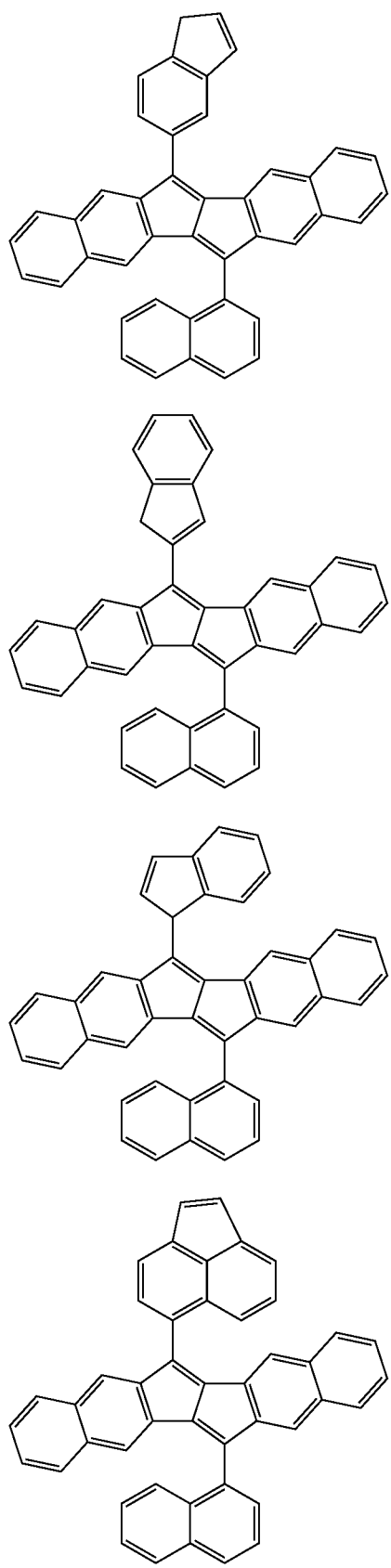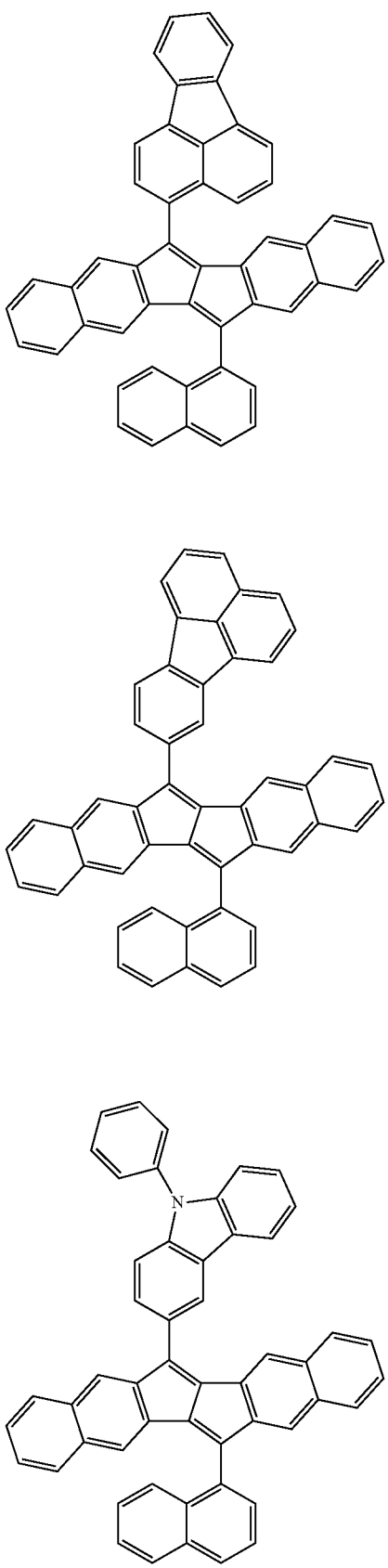

169
-continued
125
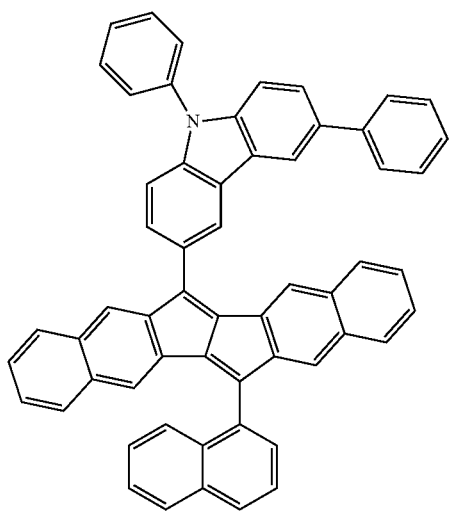
126
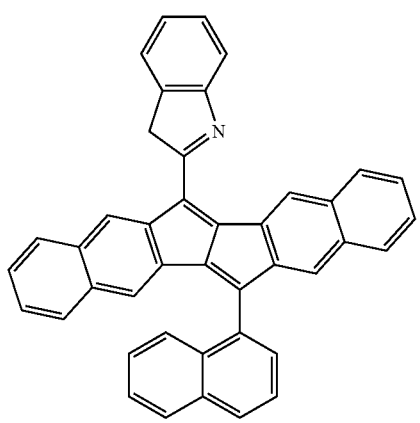
127
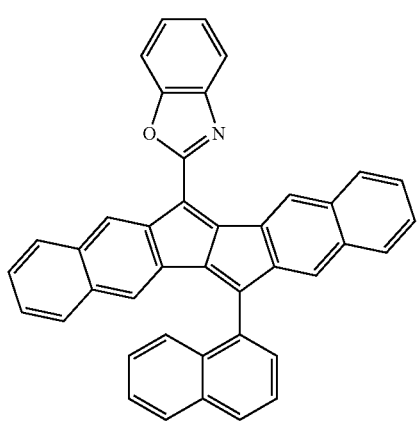
170
-continued
128
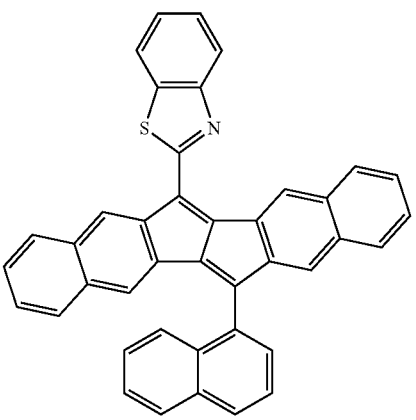
129
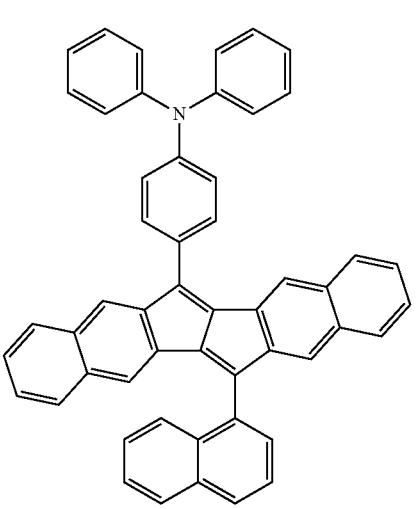
138
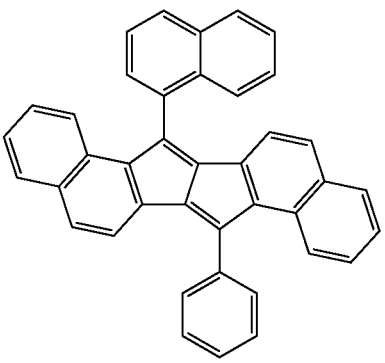

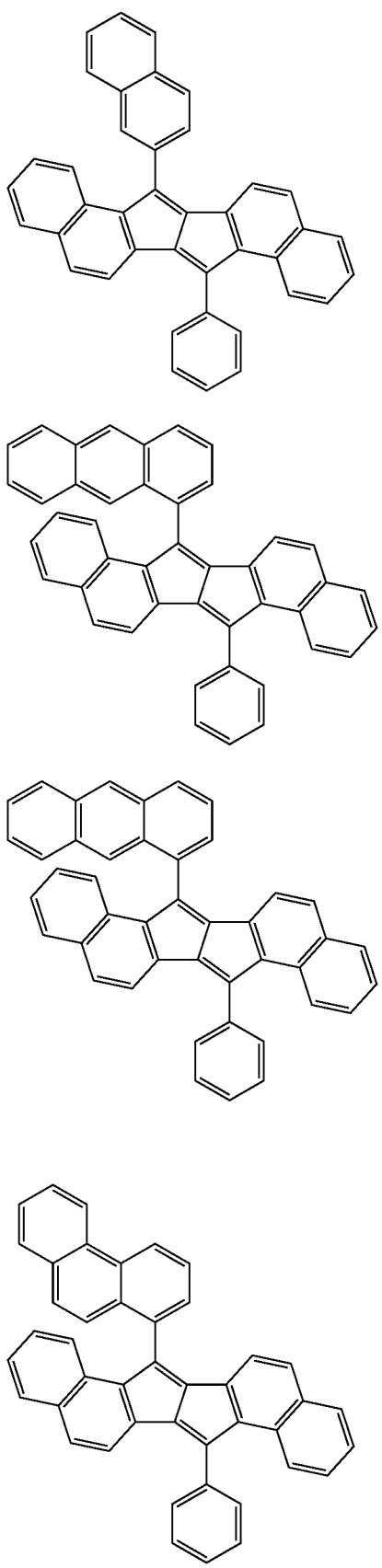
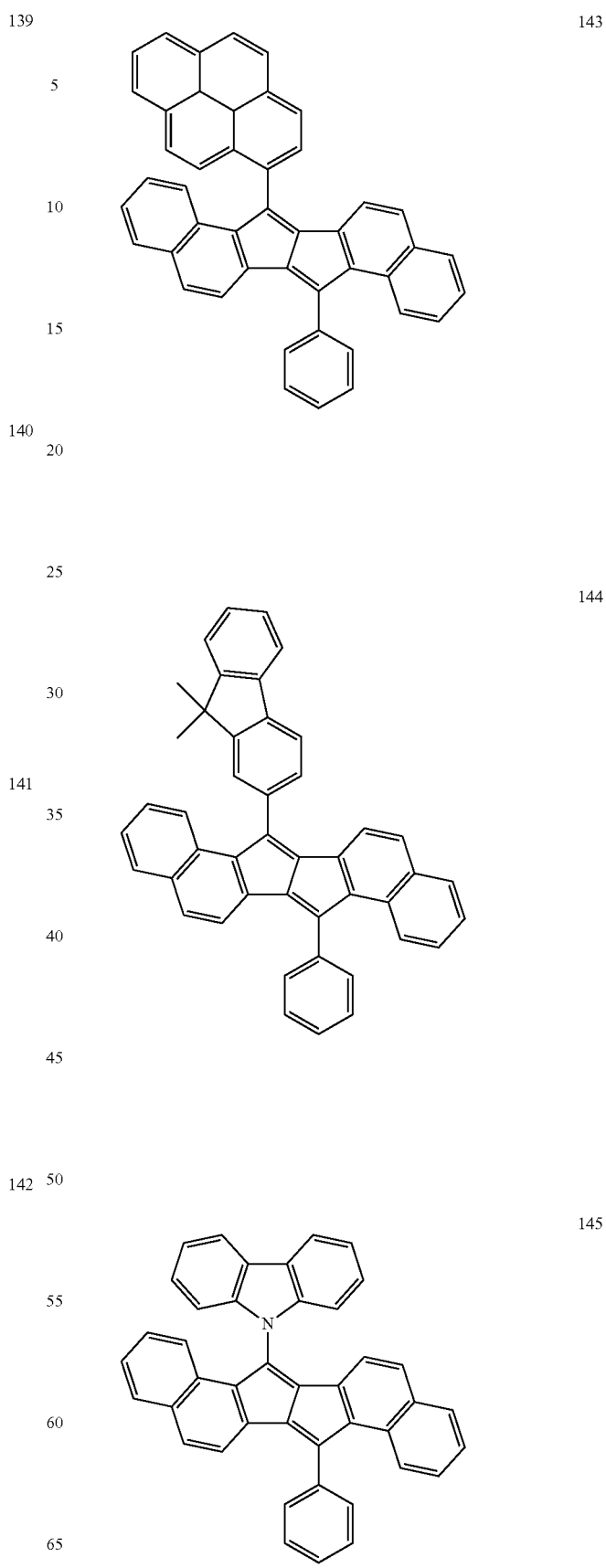

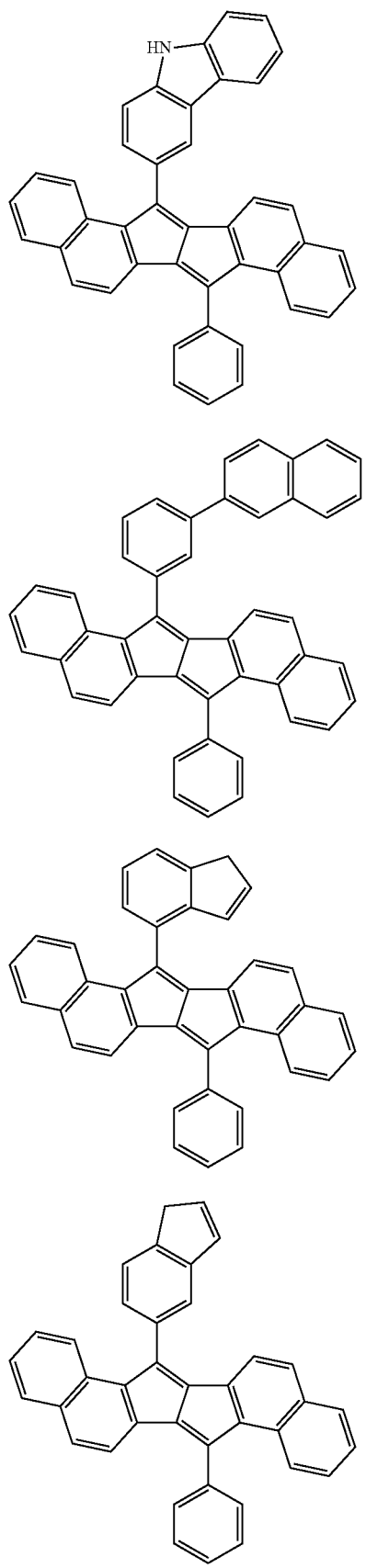
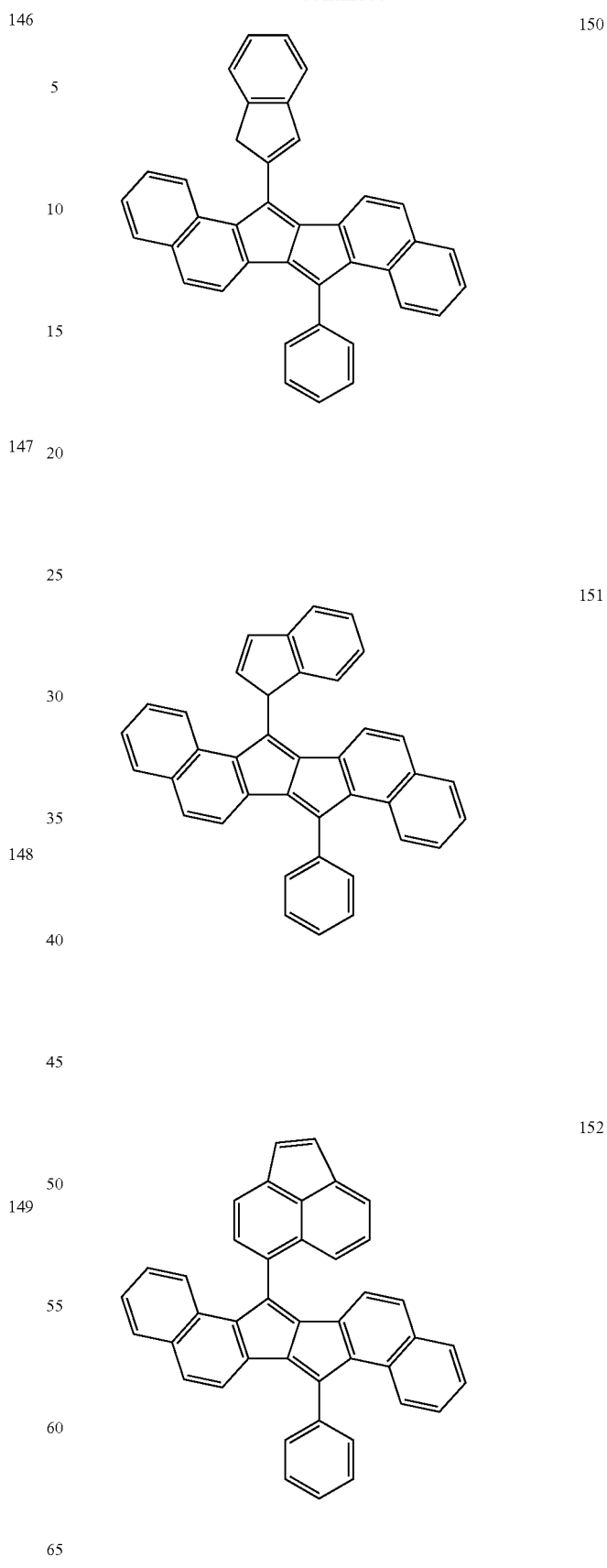

153
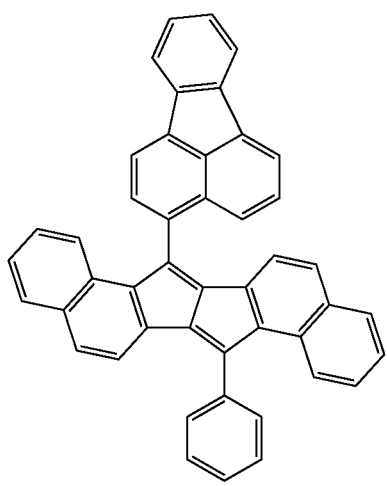
154
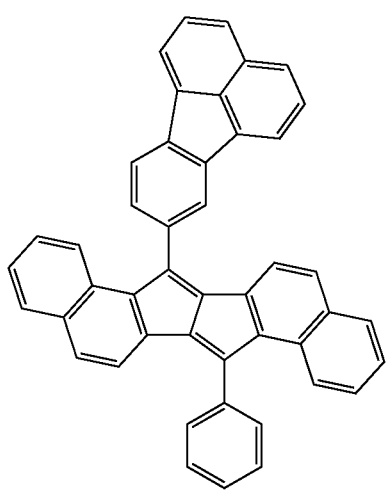
155
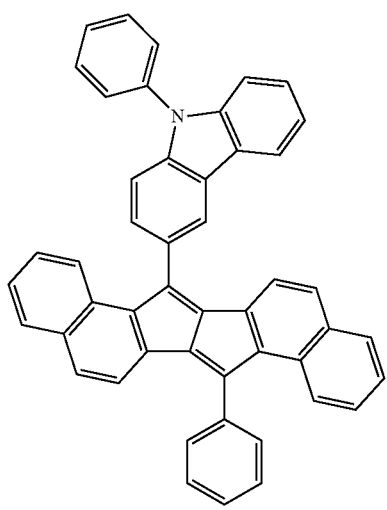
156
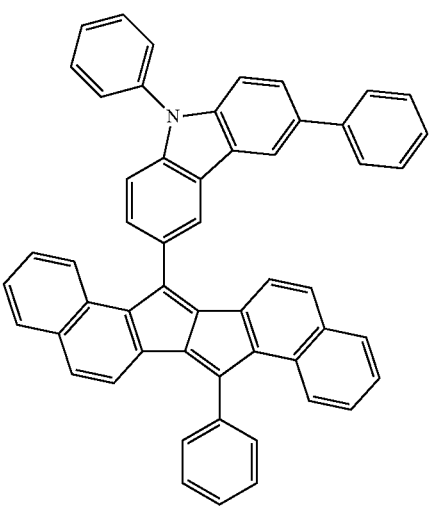
157
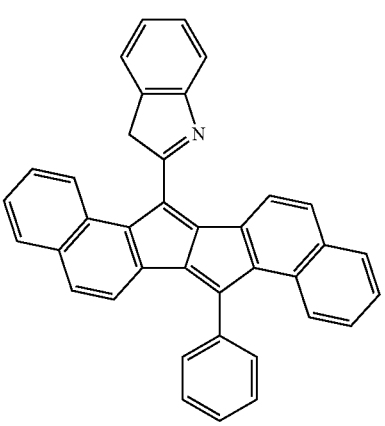
158
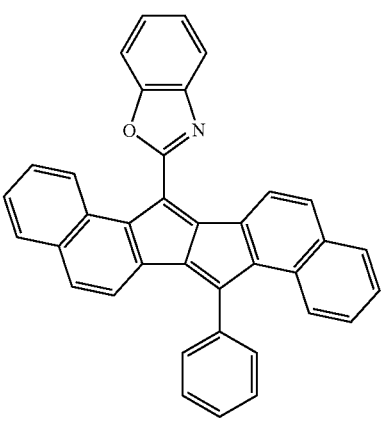

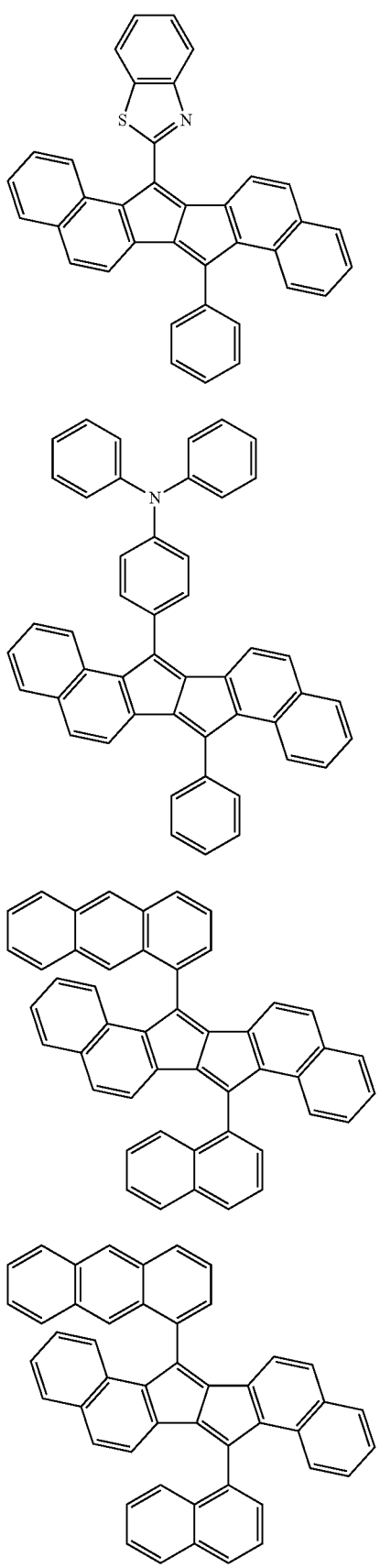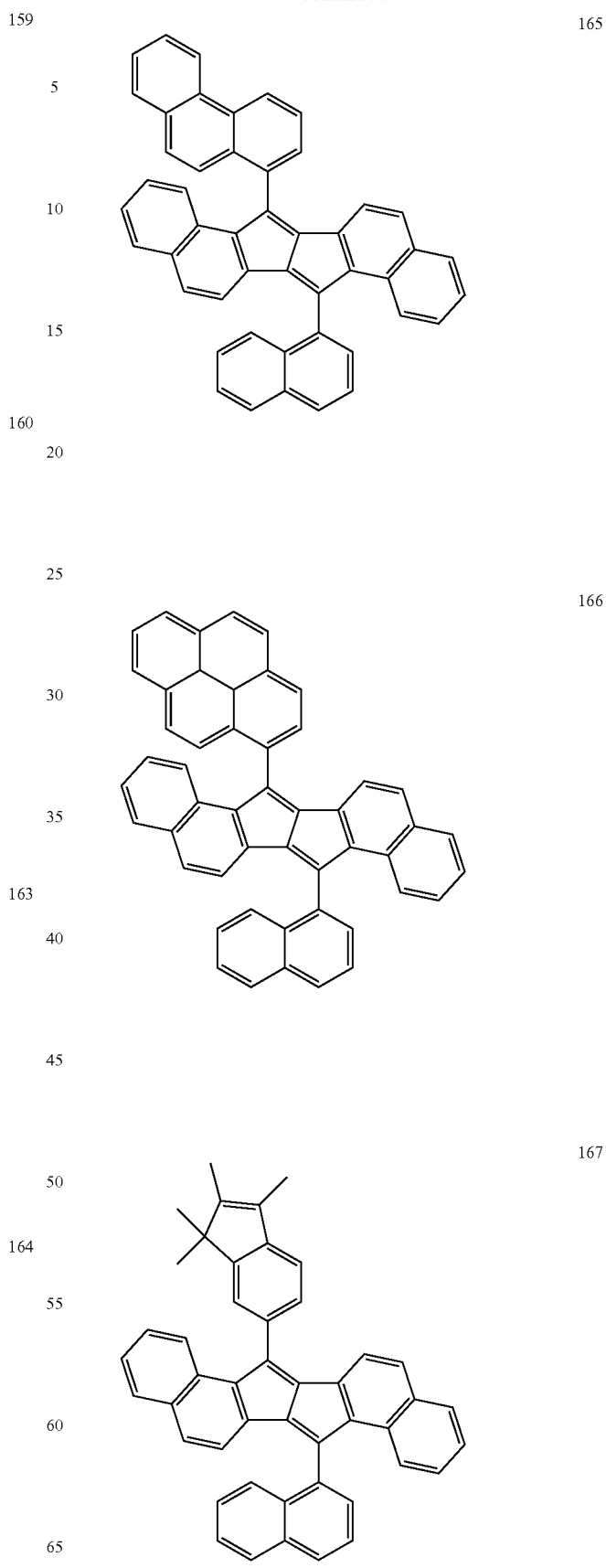

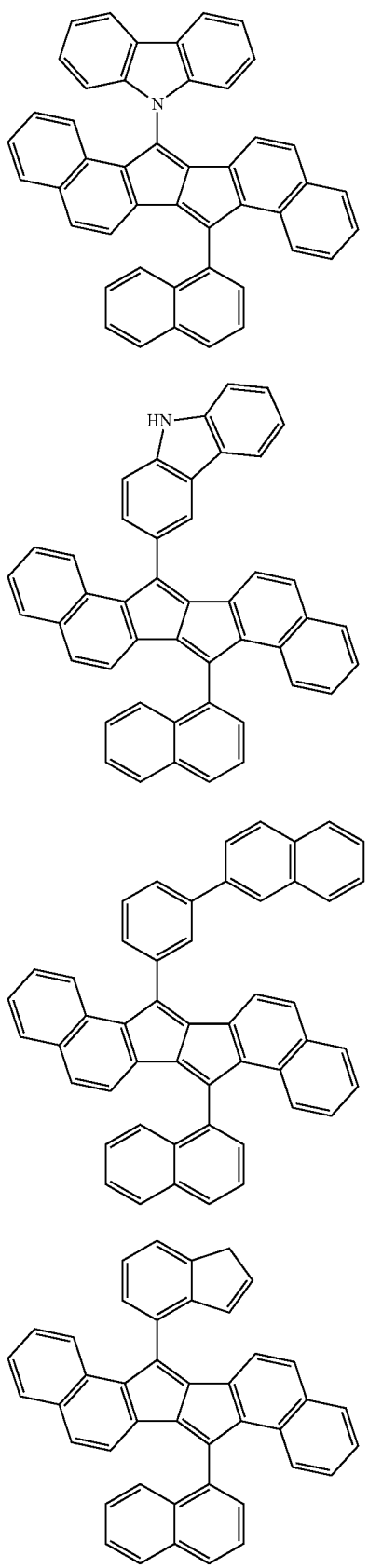
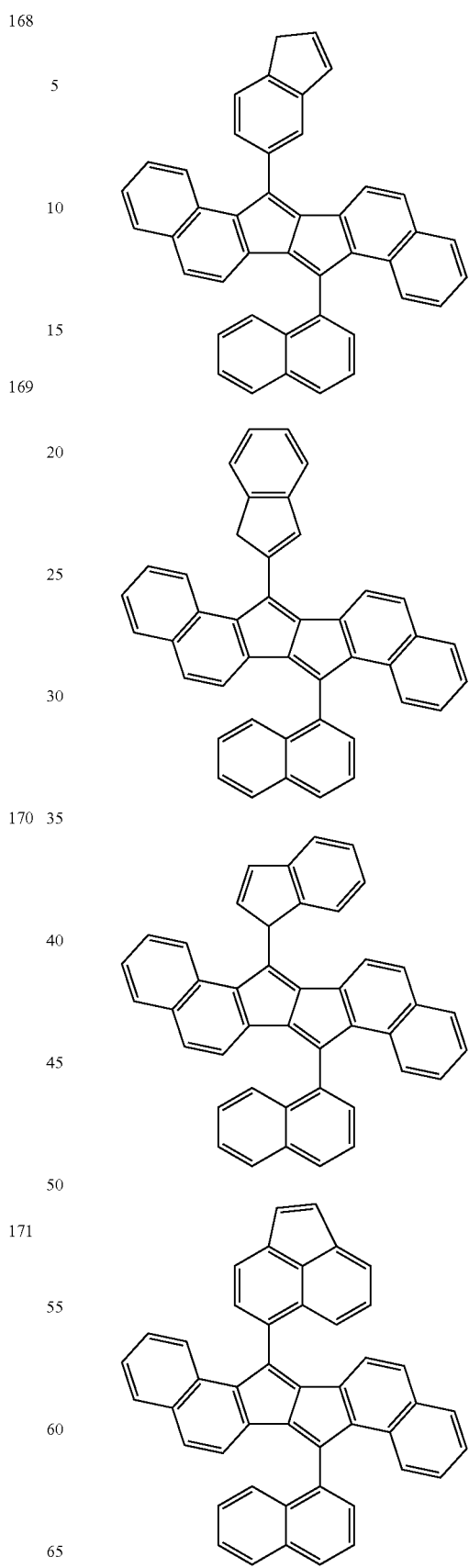

-continued
176
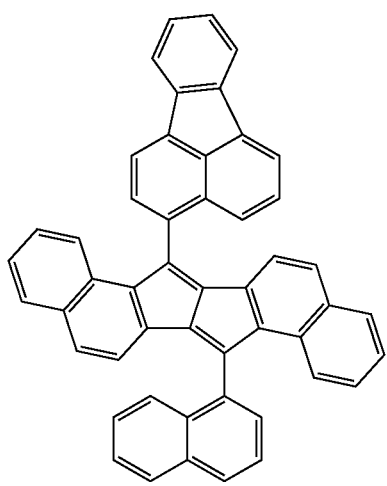
177
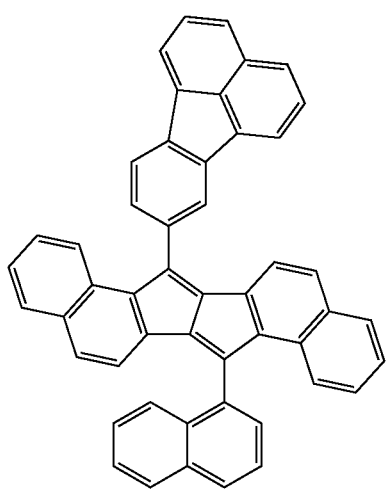
178
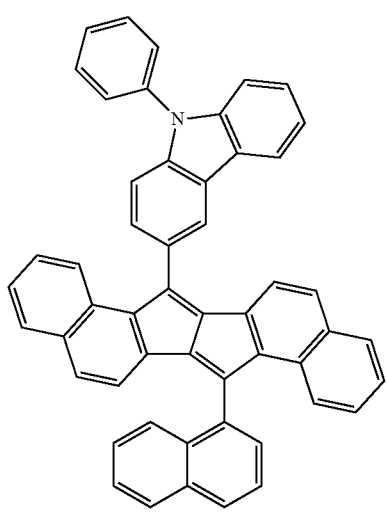
-continued
179
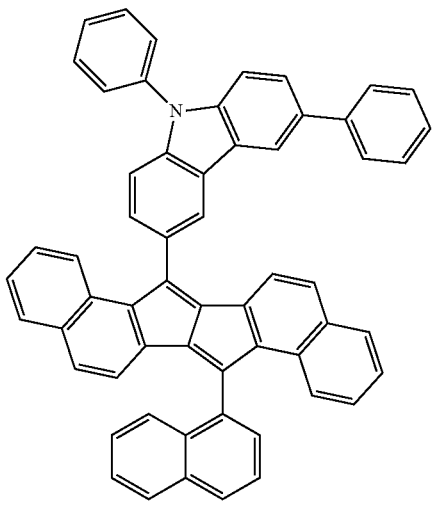
180
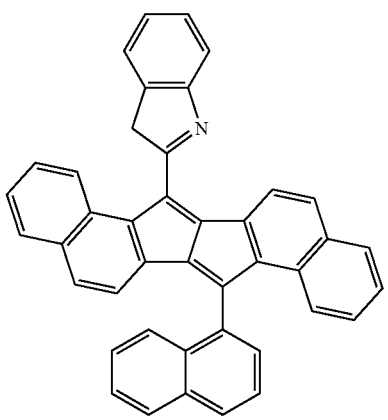
181
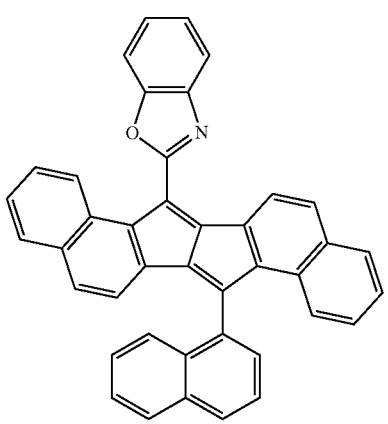

182
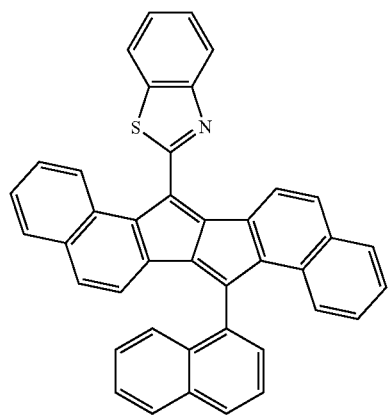
183
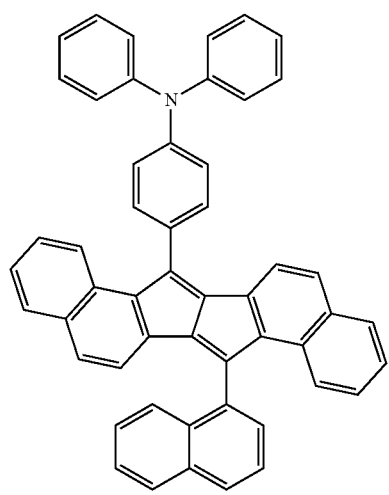
189
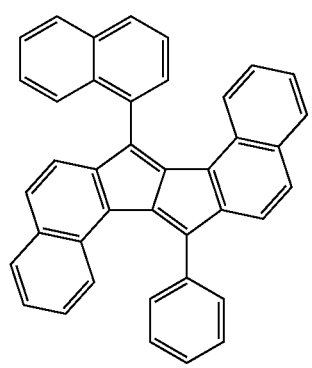
190
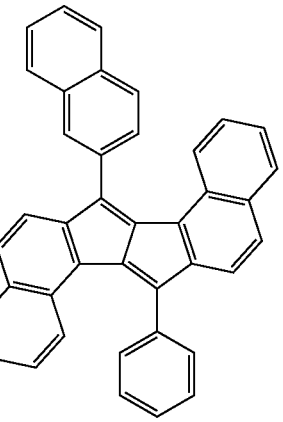
191
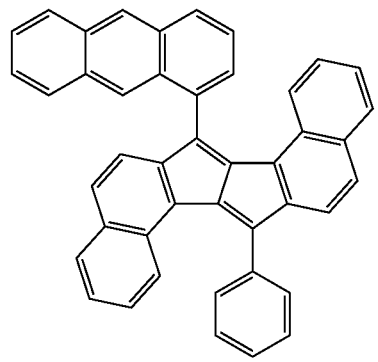
192
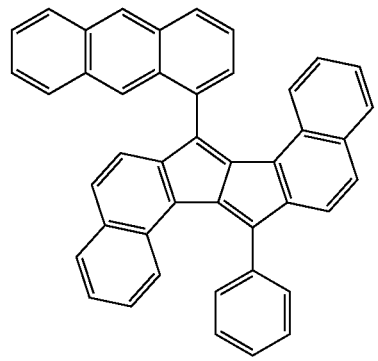
193
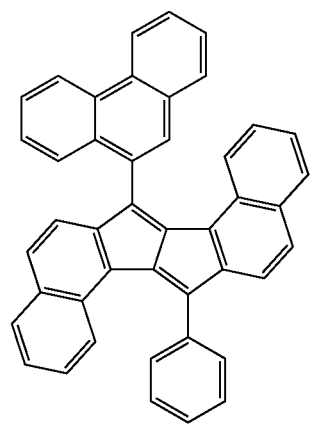

185
-continued
194
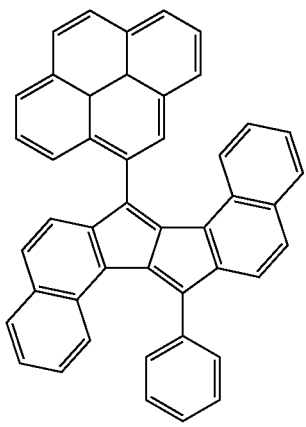
195
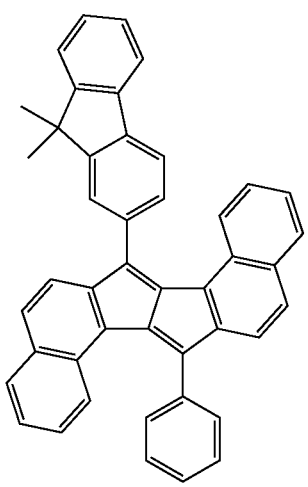
196
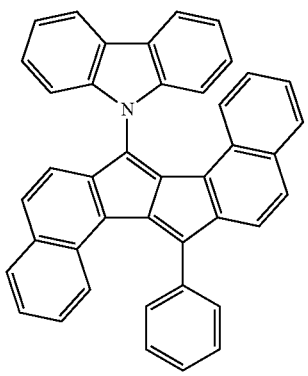
186
-continued
197
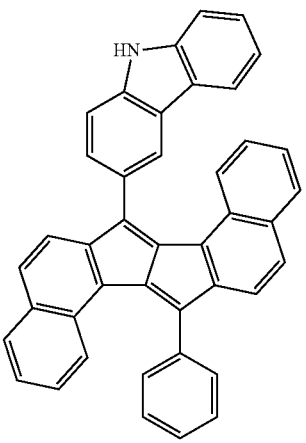
198
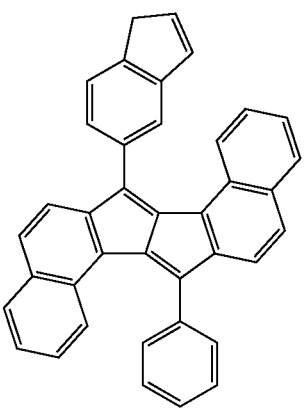
199
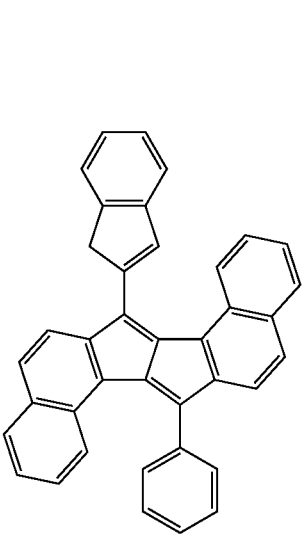

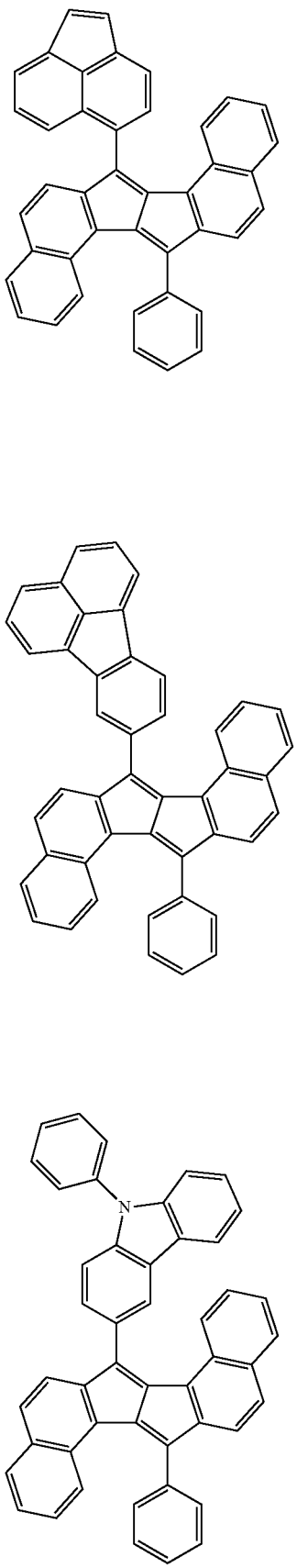
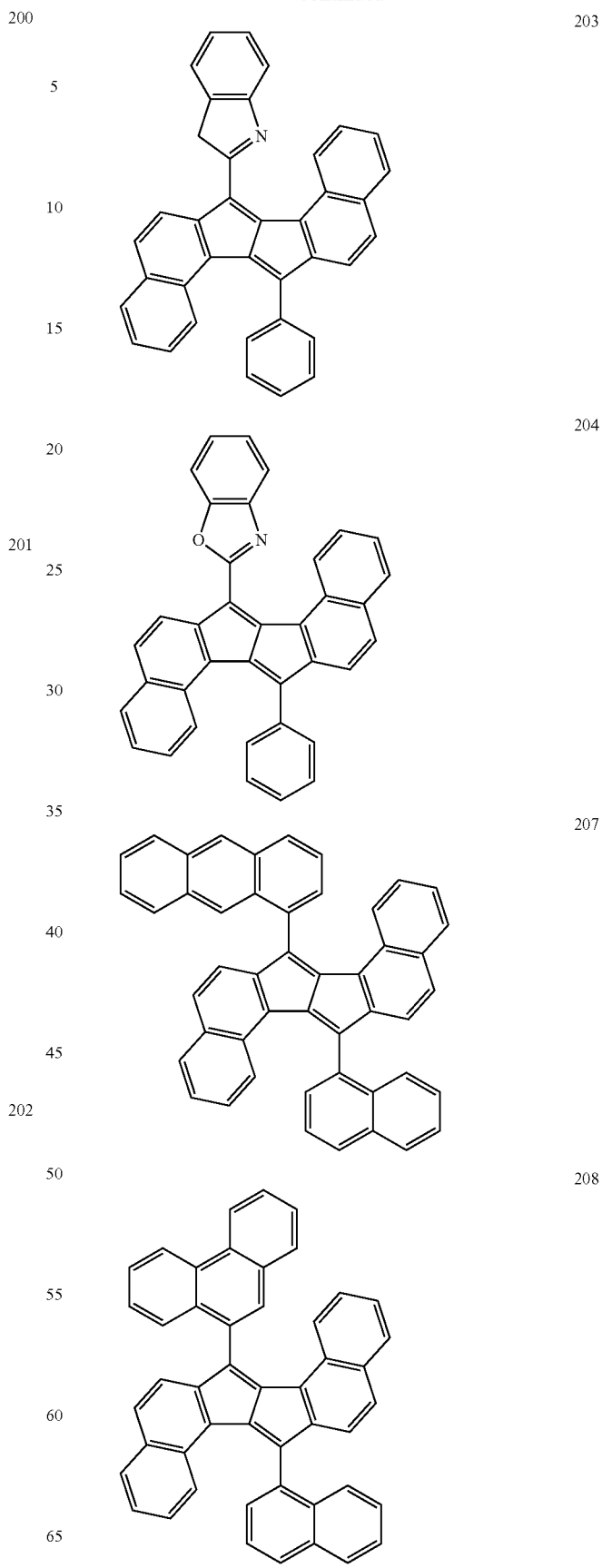

189
-continued
209
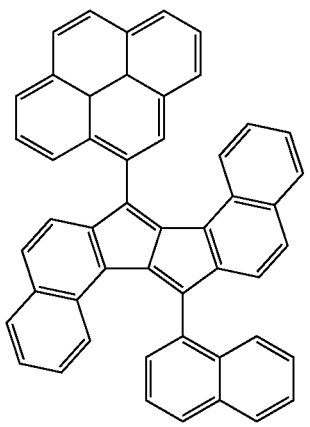
210
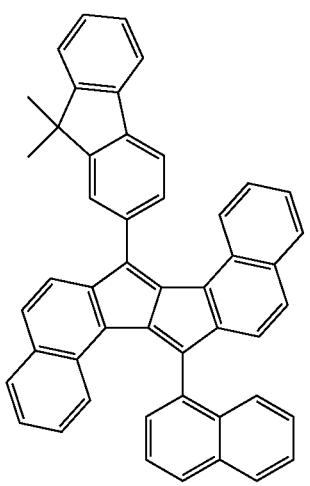
211
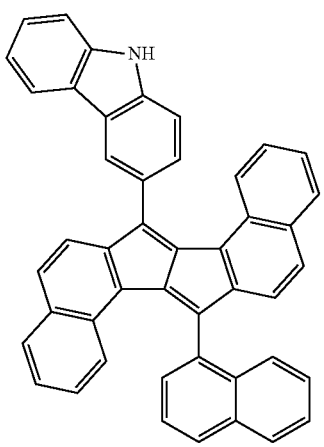
190
-continued
212
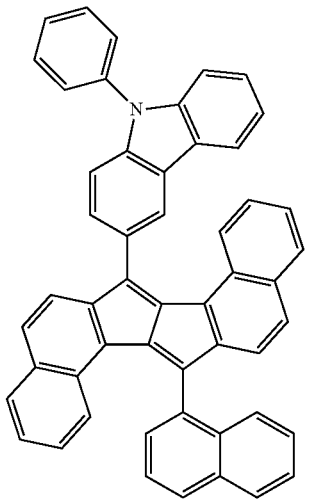
213
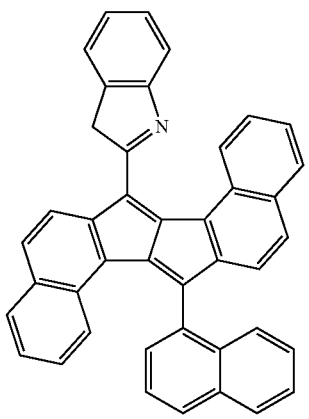
214
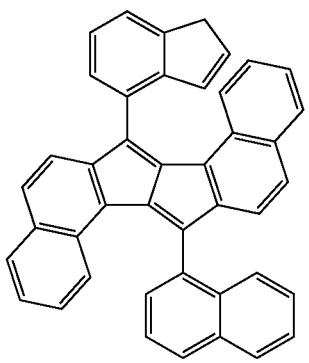
215
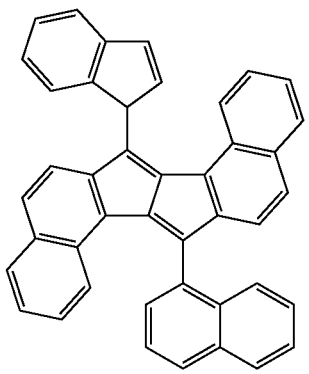

216
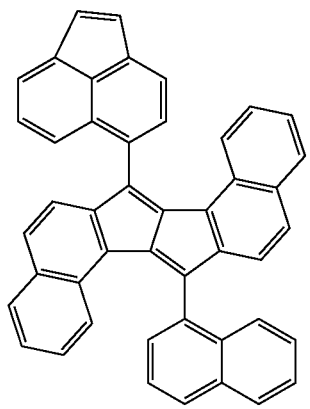
217
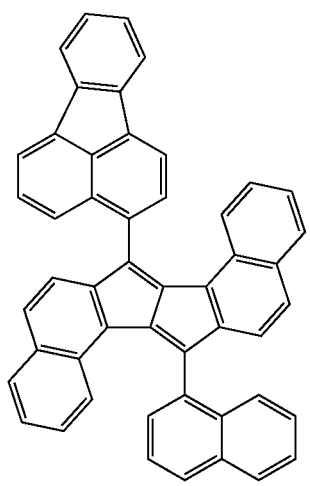
223
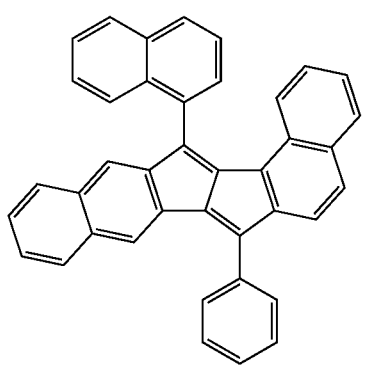
224
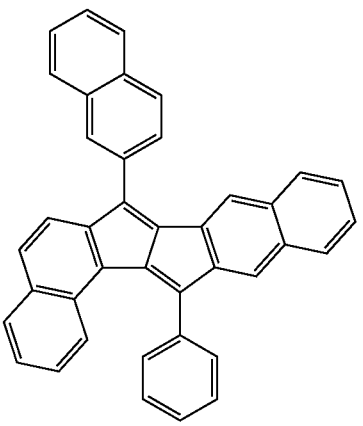
225
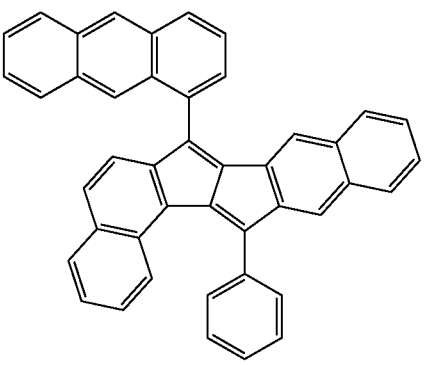
226
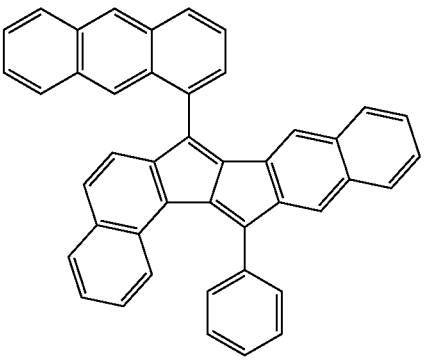
227
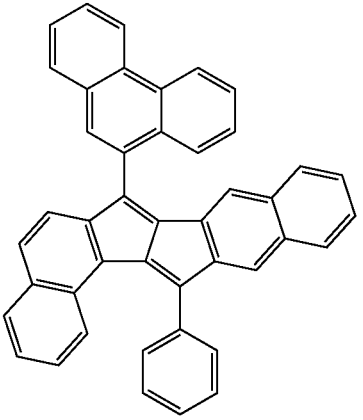

193
-continued
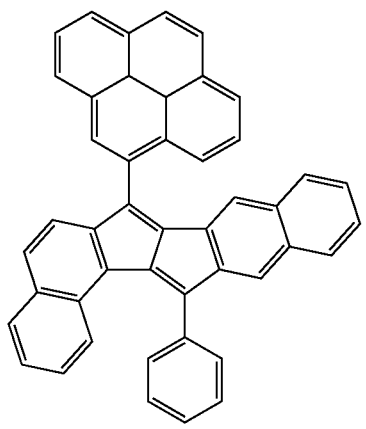
228
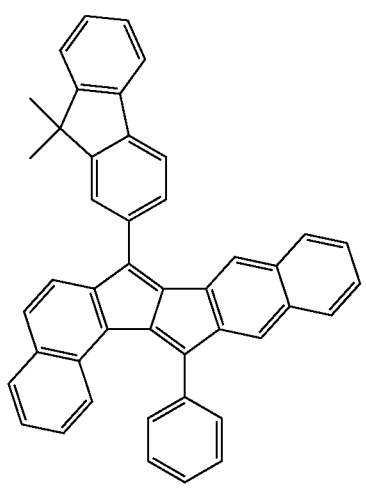
229
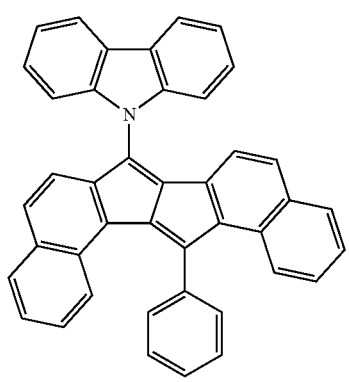
230
194
-continued
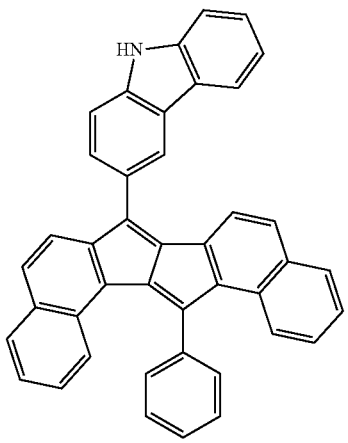
231
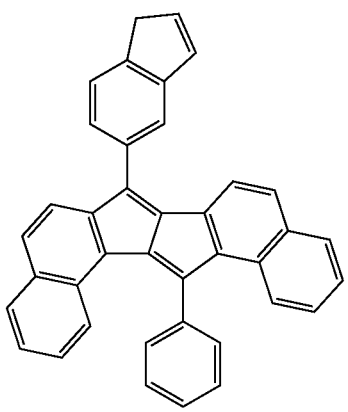
232
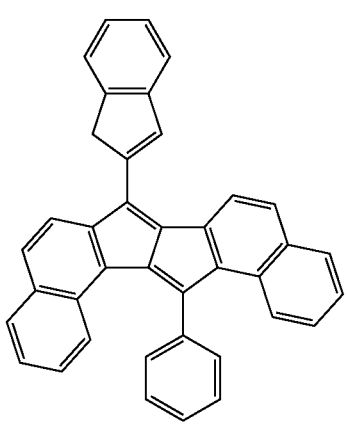
233

234
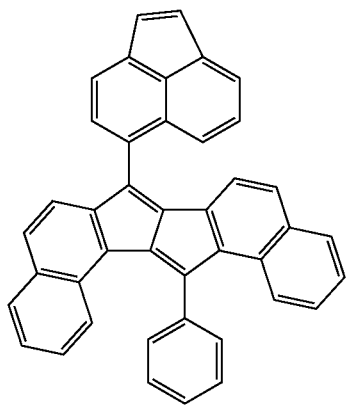
235
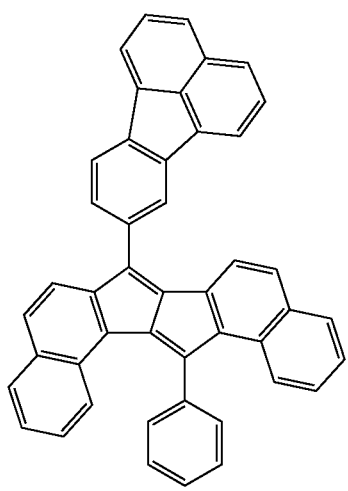
236
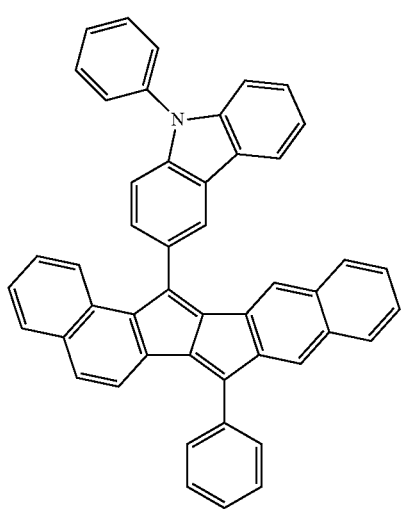
237
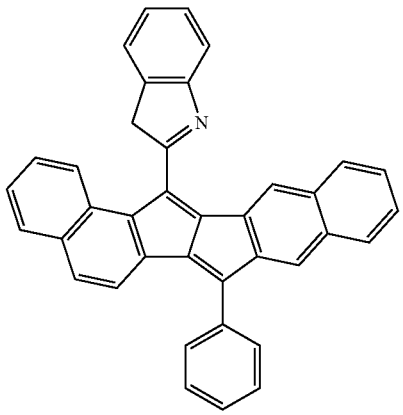
238
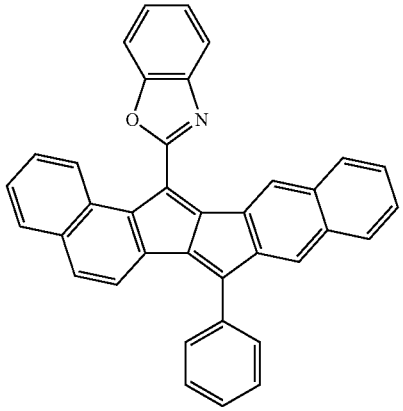
241
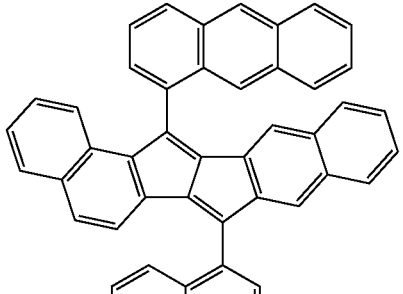
242
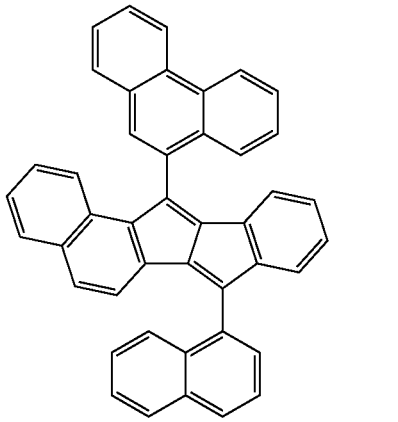

197
-continued
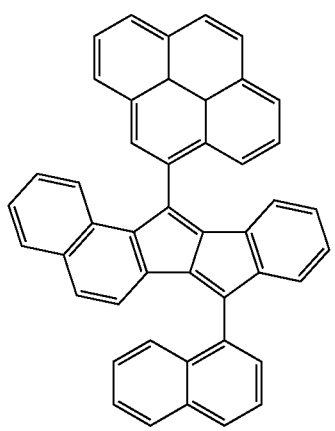
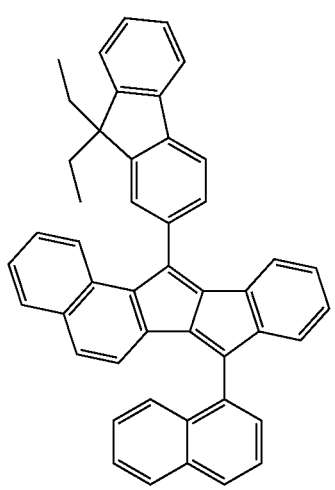
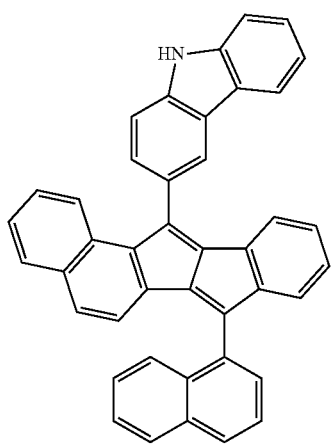
198
-continued
243
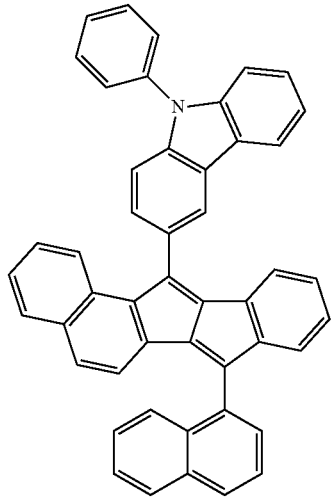
244
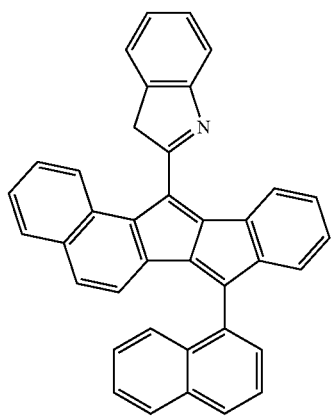
245
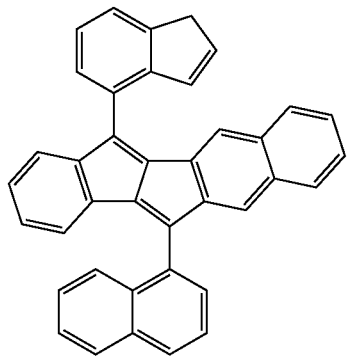
246
247
248
249

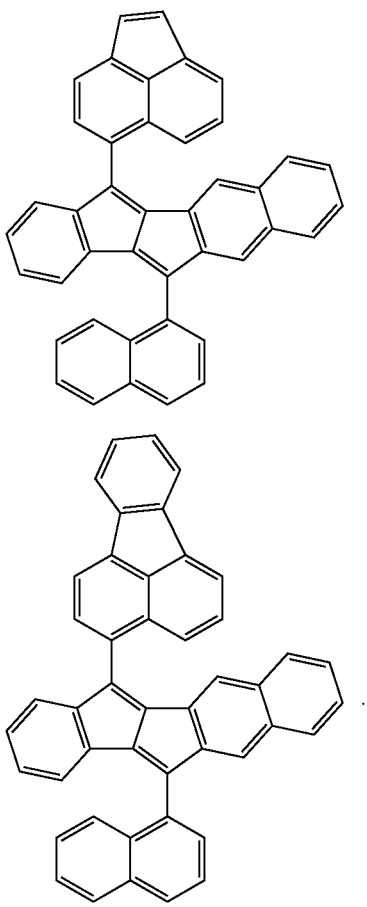

7. An organic light emitting device comprising:
a first electrode;
a second electrode; and
one or more organic material layers provided between the first electrode and the second electrode,
wherein one or more layers of the organic material layers include the compound of Chemical Formula 1 of claim 1.

8. The organic light emitting device of claim 7, wherein the one or more organic material layers that includes the compound of Chemical Formula 1 is a light emitting layer.

9. The organic light emitting device of claim 7, wherein the one or more organic material layers that includes the compound of Chemical Formula 1 further includes a fluorescent dopant.

10. The organic light emitting device of claim 7, wherein the one or more organic material layers that includes the compound of Chemical Formula 1 further includes a blue fluorescent dopant.

11. The organic light emitting device of claim 7, wherein the one or more organic material layers that includes the compound of Chemical Formula 1 further includes a phosphorescent dopant.

12. The organic light emitting device of claim 7, wherein the one or more organic material layers that includes the compound of Chemical Formula 1 further includes one or more compounds selected from the group consisting of arylamine-based compounds or styrylarylamine-based compounds.

13. The organic light emitting device of claim 7, wherein the one or more organic material layers that includes the compound of Chemical Formula 1 further includes one or more metals or complex compounds selected from the group consisting of group 1, group 2, period 4 and period 5 transition metals, lanthanide-series metals, and organic metals of d-transition atoms.

14. The organic light emitting device of claim 7, further comprising:
one or more organic materials emitting blue, red or green light, in addition to the compound of Chemical Formula 1.

15. The organic light emitting device of claim 7, further comprising:
one or more organic material layers emitting blue, red or green light, in addition to the organic material layer including the compound of Chemical Formula 1.

16. The organic light emitting device of claim 7, which emits white light.

* * * * *